United States Patent
Cheloha et al.

(10) Patent No.: US 11,878,063 B2
(45) Date of Patent: Jan. 23, 2024

(54) ENGINEERED LIGANDS AND USES THEREOF

(71) Applicants: Children's Medical Center Corporation, Boston, MA (US); The General Hospital Corporation, Boston, MA (US)

(72) Inventors: Ross Cheloha, Boston, MA (US); Hidde L. Ploegh, Boston, MA (US); Thomas J. Gardella, Boston, MA (US)

(73) Assignees: Children's Medical Center Corporation, Boston, MA (US); The General Hospital Corporation, Boston, MA (US)

( * ) Notice: Subject to any disclaimer, the term of this patent is extended or adjusted under 35 U.S.C. 154(b) by 3 days.

(21) Appl. No.: 16/810,783

(22) Filed: Mar. 5, 2020

(65) Prior Publication Data
US 2020/0316217 A1    Oct. 8, 2020

Related U.S. Application Data

(60) Provisional application No. 62/814,096, filed on Mar. 5, 2019.

(51) Int. Cl.
*A61K 47/68* (2017.01)
*A61K 47/62* (2017.01)

(52) U.S. Cl.
CPC .......... *A61K 47/6849* (2017.08); *A61K 47/62* (2017.08)

(58) Field of Classification Search
None
See application file for complete search history.

(56) References Cited

U.S. PATENT DOCUMENTS

| | | | |
|---|---|---|---|
| 2010/0062004 A1 | 3/2010 | Adams et al. | |
| 2010/0267610 A1* | 10/2010 | Blind | C07K 14/8139 514/1.1 |
| 2014/0099670 A1* | 4/2014 | Kostenuik | A61P 37/06 435/69.6 |
| 2018/0030154 A1* | 2/2018 | Levy | A61P 5/18 |

FOREIGN PATENT DOCUMENTS

WO    WO 2013-155526 A2    10/2013

OTHER PUBLICATIONS

Lloyd et al. Protein Engineering, Design & Selection 22:159-168 (Year: 2009).*
Edwards et al., J Mol Biol. 334(1): 103-118 (Year: 2003).*
Cheloha et al., Improved GPCR ligands from nanobody tethering, published in Nature Communication 2087: 2-11 (Year: 2020).*
Shimizu et al., J Biochemical Chemistry 275: 21836-21843 (Year: 2000).*
Cheloha et al., Nature Communications 11(1): 2087 (Year: 2020).*
Strop et al., Chemistry and Biology 20: 161-167 (Year: 2013).*
[No Author Listed] Description and specifications of BCO-PEG3-MAL from Conju-probe. Accessed Jun. 2020. 2 pages. https://conju-probe.com/product/dbco-peg3-mal/.
Cheloha et al., PTH receptor-1 signalling-mechanistic insights and therapeutic prospects. Nat Rev Endocrinol. Dec. 2015;11(12):712-24.
Farrants et al., SNAP-Tagged Nanobodies Enable Reversible Optical Control of a G Protein-Coupled Receptor via a Remotely Tethered Photoswitchable Ligand. ACS Chem Biol. 2018;13(9):2682-2688.
Shimizu et al., Parathyroid hormone (PTH)-(1-14) and -(1-11) analogs conformationally constrained by alpha-aminoisobutyric acid mediate full agonist responses via the juxtamembrane region of the PTH-1 receptor. J Biol Chem. 2001;276(52):49003-49012.
Shimizu et al., Minimization of parathyroid hormone. Novel amino-terminal parathyroid hormone fragments with enhanced potency in activating the type-1 parathyroid hormone receptor. J Biol Chem. 2000;275(29):21836-21843.

* cited by examiner

*Primary Examiner* — Phuong Huynh
(74) *Attorney, Agent, or Firm* — Wolf, Greenfield & Sacks, P.C.

(57) ABSTRACT

Described herein are engineered ligand that binds a cell surface receptor (e.g., GPCR), with improved affinity, potency, and specificity. By conjugating a sub-optimal ligand for a cell surface receptor (e.g., GPCR) to a targeting molecule that binds an epitope (natural or exogenous epitope) in the extracellular portion of the cell surface receptor (e.g., GPCR), the affinity, potency, and/or specificity of the sub-optimal ligand is enhanced.

14 Claims, 42 Drawing Sheets
Specification includes a Sequence Listing.

| | VHH name | Target |
|---|---|---|
| VHH | Enhancer | GFP, YFP |
| VHH | VHH05 | Peptide from intracellular protein (Ubc6e), sequence QADQEAKELARQIS (SEQ ID NO: 53) |

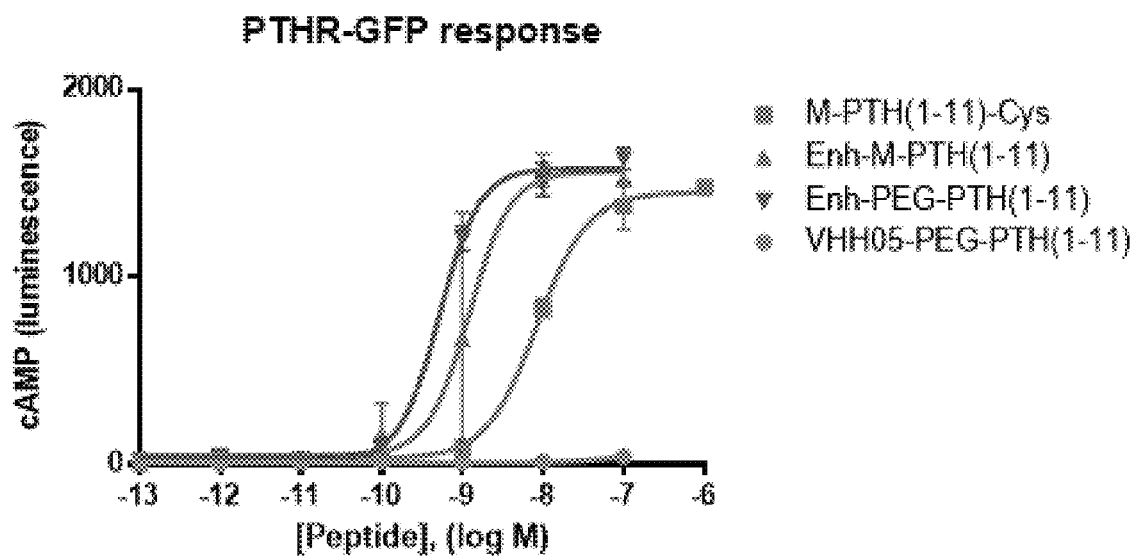
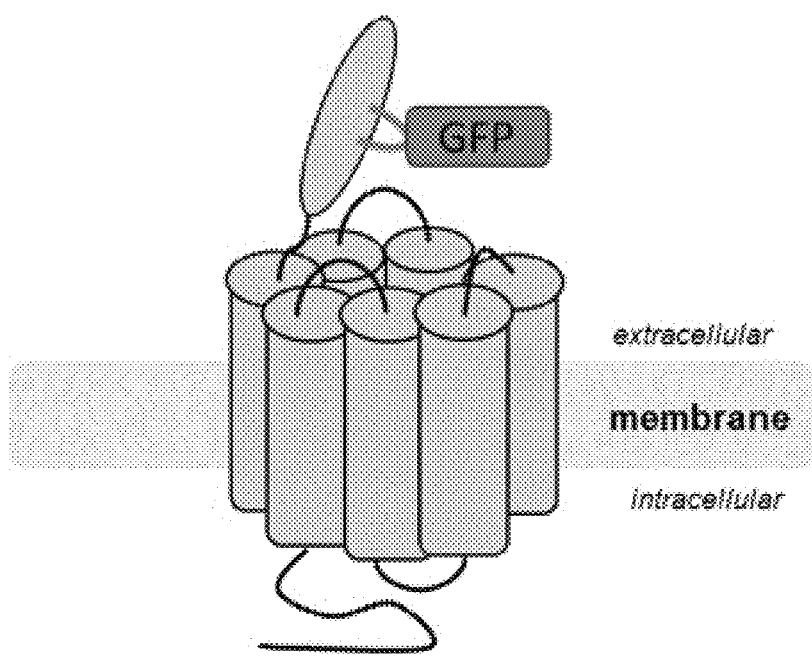
FIG. 7A

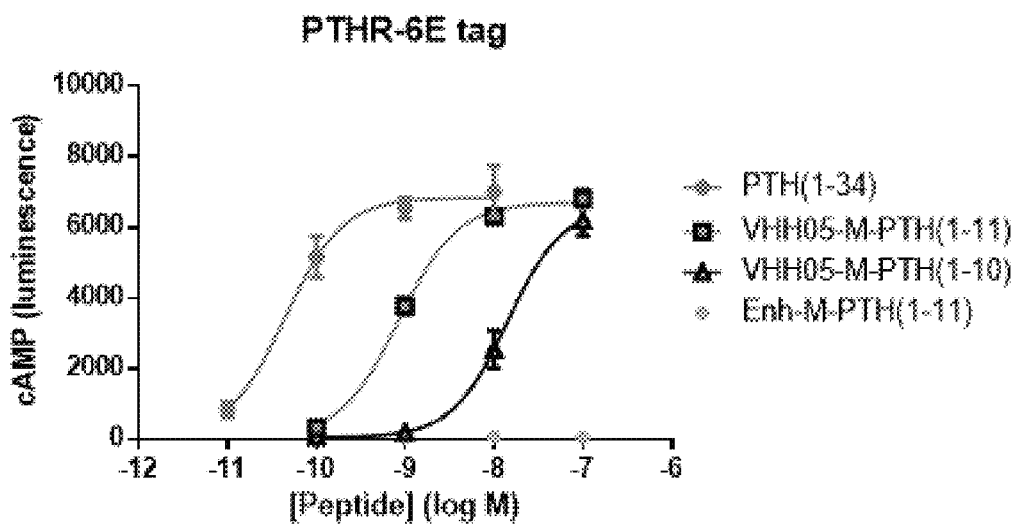
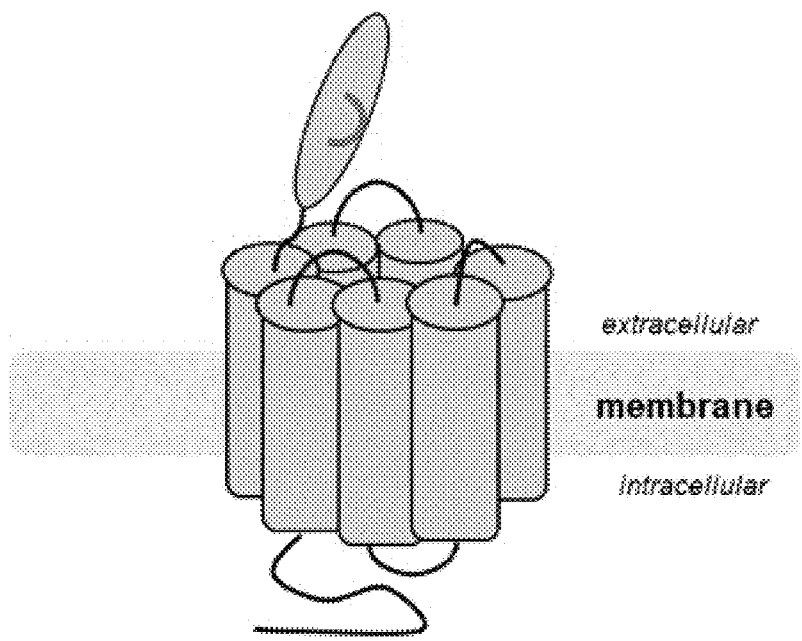
FIG. 7B

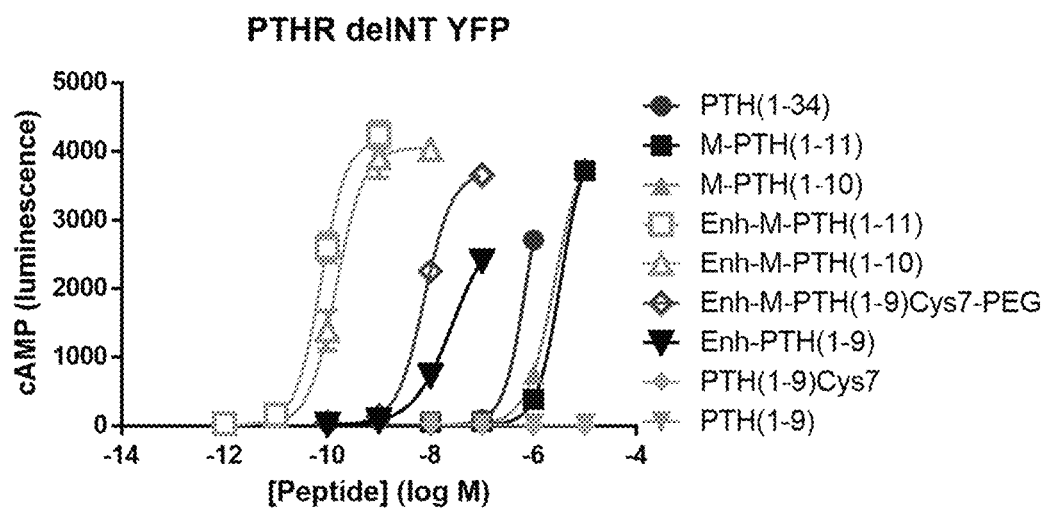
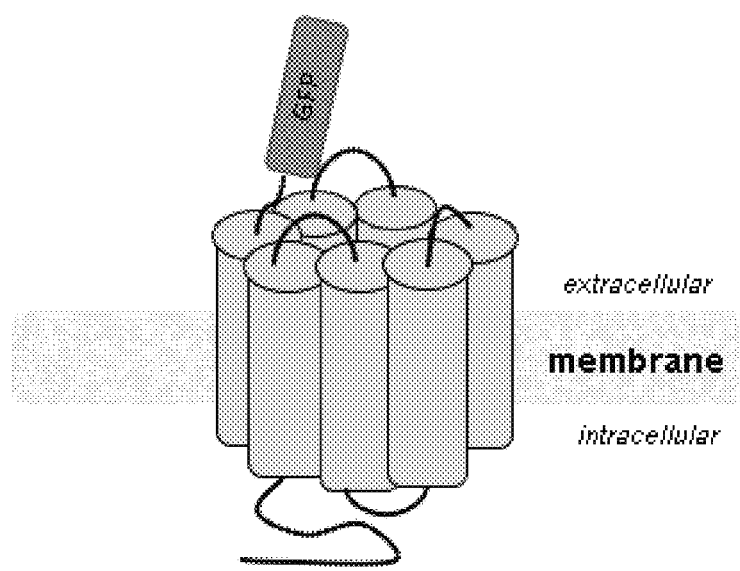
FIG. 8

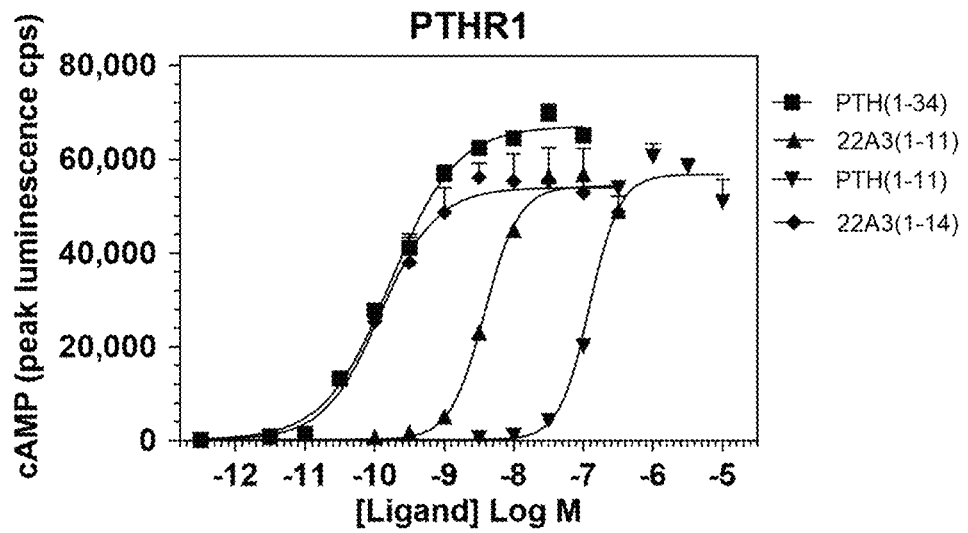
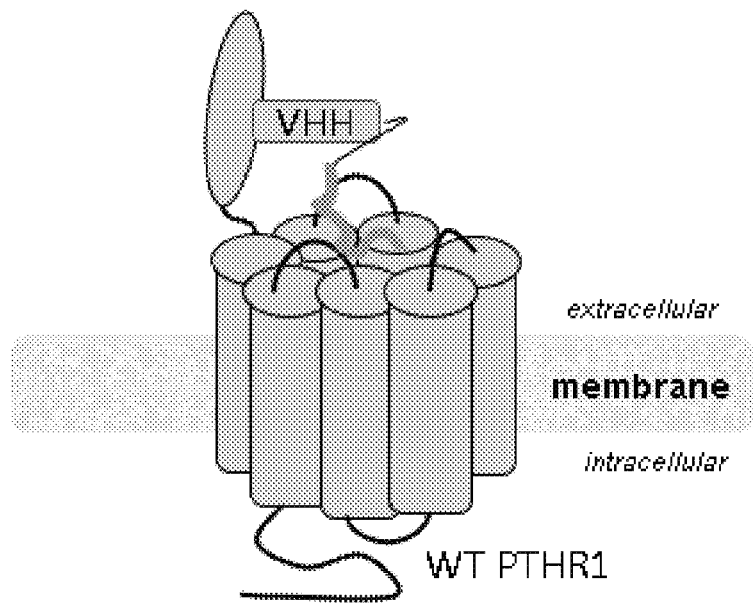
FIG. 9

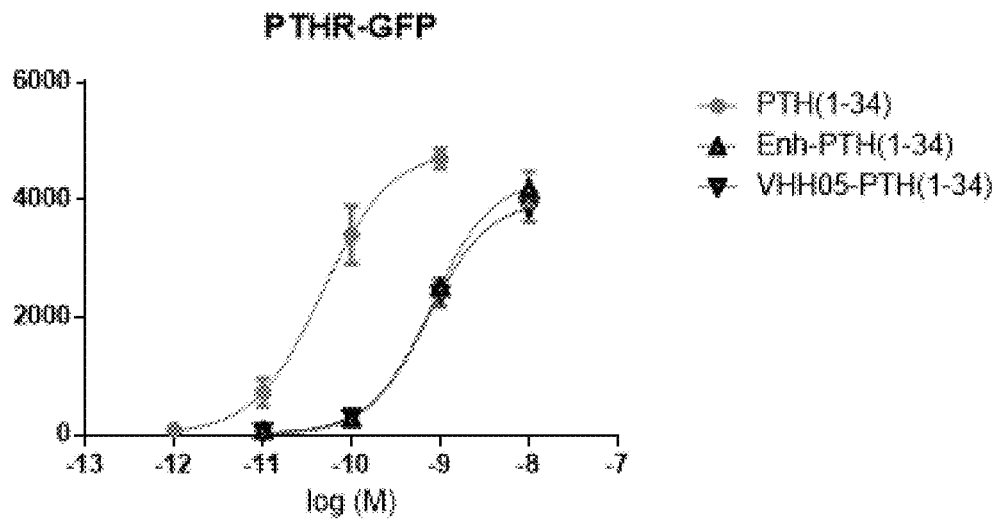
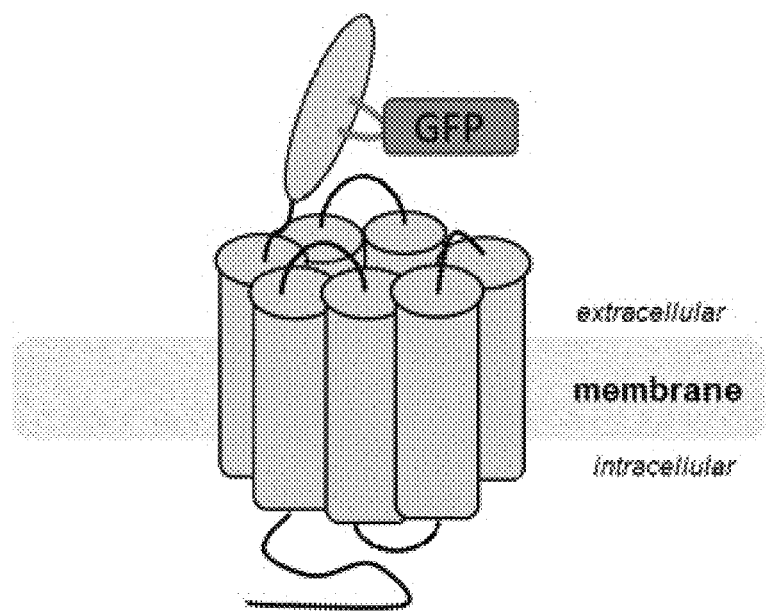
FIG. 10

PTH(1-9)  : AVUEIQLMHC (SEQ ID NO: 92)
PTH(1-10) : AVUEIQLMHQC (SEQ ID NO: 93)
PTH(1-11) : AVUEIQLMHQRC (SEQ ID NO: 94)
PTH(1-14) : AVUEIQLMHQRAKWC (SEQ ID NO: 95)
PTH(1-34) : SVSEIQLMHNLGKH(15-34)C (SEQ ID NO: 96)

| Ligand | hPTHR1 (EC$_{50}$, nM) | hPTHR2 |
|---|---|---|
| PTH(1-34) | 0.31 ± 0.16 | 1.45 ± 2.42 |
| PTH(1-14) | 3.5 ± 1.3 | 924 ± 328 |
| VHH$_{PTHR}$-PTH(1-14) | 0.071 ± 0.044 | Inactive at 330 nM |
| VHH$_{6E}$-PTH(1-14) | Inactive at 330 nM | Inactive at 330 nM |

| Peptide or conjugate | PTHR1$_{GFP}$ |
|---|---|
| PTH(1-34) | 0.4 ± 0.8 |
| PTH(1-14) | 2.3 ± 1.2 |
| PTH(1-11) | 79 ± 45 |
| PTH(1-10) | 2552 ± 653 |
| PTH(1-9) | Inactive at 10,000 nM |
| VHH$_{PTHR}$-PTH(1-14) | 0.5 ± 0.2 |
| VHH$_{PTHR}$-PTH(1-11) | 0.5 ± 0.1 |
| VHH$_{PTHR}$-PTH(1-10) | ND |
| VHH$_{6E}$-PTH(1-14) | ND |
| VHH$_{6E}$-PTH(1-11) | Inactive at 100 nM |
| VHH$_{6E}$-PTH(1-10) | Inactive at 100 nM |
| VHH$_{6E}$-PTH(1-9) | ND |
| VHH$_{GFP}$-PTH(1-14) | 1.8 ± 0.6 |
| VHH$_{GFP}$-PTH(1-11) | 8.0 ± 3.4 |
| VHH$_{GFP}$-PTH(1-10) | Inactive at 100 nM |
| VHH$_{GFP}$-PTH(1-10) | Inactive at 100 nM |

FIG. 17C

| Peptide | [M+H]$_{calc}$ | [M+H]$_{obs}$ |
|---|---|---|
| PTH(1-9) | 1127.6 | 1127.1 |
| PTH(1-10) | 1255.6 | 1255.1 |
| PTH(1-11) | 1411.7 | 1411.2 |
| PTH(1-14) | 1796.9 | 1796.3 |
| PTH(1-34) | 4218.2 | 4217.5 |
| PTH(1-9)-dbco | 1554.8 | 1554.2 |
| PTH(1-10)-dbco | 1682.8 | 1682.2 |
| PTH(1-11)-dbco | 1838.9 | 1839 |
| PTH(1-14)-dbco | 2224.1 | 2223.5 |
| PTH(1-34)-dbco | 4645.4 | 4644.6 |
| PTH(1-11)-PEG3-dbco | 2042 | 2041.4 |
| PTH(1-34)-PEG3-dbco | 4848.5 | 4847.7 |
| G$_3$-PTH(1-14) | 1865 | 1864.2 |

FIG. 18

| Conjugate | MW$_{calc}$ | MW$_{obs}$ |
|---|---|---|
| VHH$_{GFP}$-G3-Lys(biotin)AhxLys(azide) | n/a | 14080 |
| VHH$_{GFP}$-PTH(1-9) | 15635 | 15635 |
| VHH$_{GFP}$-PTH(1-10) | 15763 | 15765 |
| VHH$_{GFP}$-PTH(1-11) | 15919 | 15920 |
| VHH$_{GFP}$-PTH(1-14) | 16304 | 16305 |
| VHH$_{GFP}$-G3-PTH(1-14) | 15135 | 15135 |
| VHH$_{GFP}$-PTH(1-34)-PEG | 18929 | 18930 |
| VHH$_{6E}$-G3-Lys(biotin)AhxLys(azide) | n/a | 13325 |
| VHH$_{6E}$-PTH(1-9) | 14880 | 14895 |
| VHH$_{6E}$-PTH(1-10) | 15008 | 15010 |
| VHH$_{6E}$-PTH(1-11) | 15164 | 15165 |
| VHH$_{6E}$-PTH(1-11)-PEG | 15367 | 15375 |
| VHH$_{6E}$-PTH(1-14) | 15549 | 15550 |
| VHH$_{6E}$-PTH(1-34)-PEG | 18174 | 18175 |
| VHH$_{6E}$-G3-PTH(1-14) | 14380 | 14380 |
| VHH$_{PTHR}$-PTH(1-9) | 16505 | 16505 |
| VHH$_{PTHR}$-PTH(1-10) | 16633 | 16635 |
| VHH$_{PTHR}$-PTH(1-11) | 16789 | 16790 |
| VHH$_{PTHR}$-PTH(1-14) | 17174 | 17175 |
| VHH$_{PTHR}$-G3-Lys(biotin)AhxLys(azide) | n/a | 14950 |
| VHH$_{PTHR}$-G3-PTH(1-14) | 16005 | 16005 |

FIG. 19

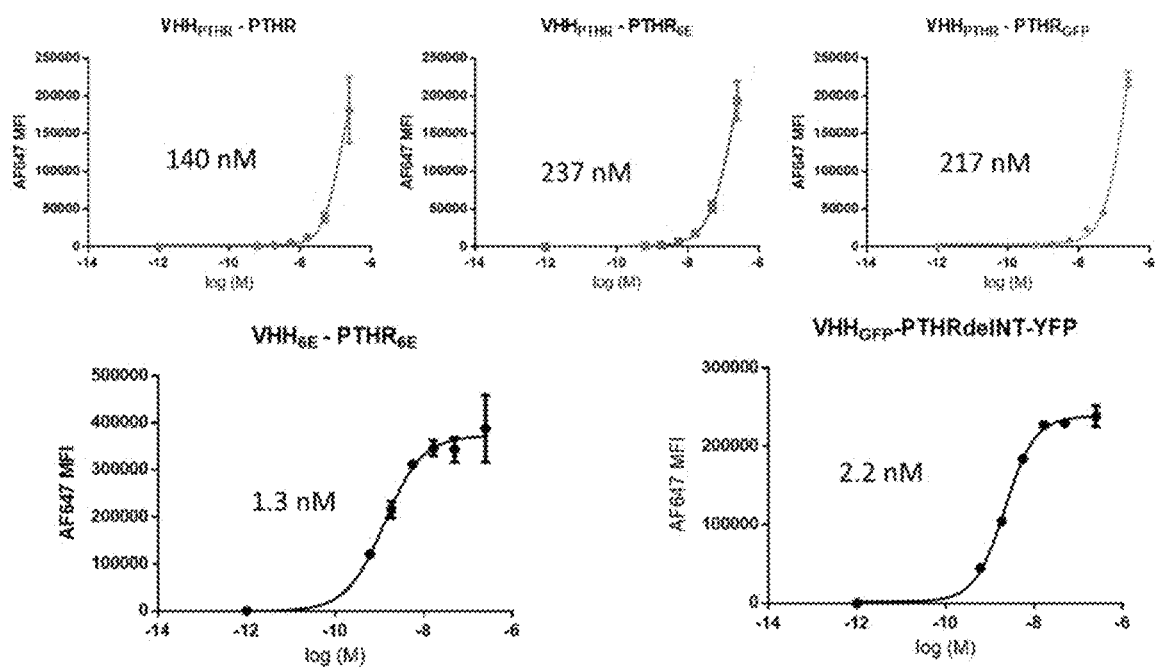

FIG. 20

| Peptide/conjugate | EC$_{50}$, nM (± SD) | | | n |
|---|---|---|---|---|
| PTH(1-34) | 0.38 | ± | 0.23 | 4 |
| PTH(1-14) | 2.8 | ± | 1.5 | 4 |
| G$_3$-PTH(1-14) | 208 | ± | 135 | 4 |
| VHH$_{PTHR}$-G$_3$-PTH(1-14) | No activity at 100 nM | | | 3 |
| VHH$_{6E}$-G$_3$-PTH(1-14) | No activity at 100 nM | | | 3 |

| Peptide/conjugate | EC$_{50}$, nM (± SD) | | | n |
|---|---|---|---|---|
| PTH(1-34) | 0.67 | ± | 0.64 | 6 |
| PTH(1-11) | 336 | ± | 208 | 7 |
| PTH(1-11)-DBCO | 65 | ± | 48 | 4 |
| PTH(1-11)-PEG-DBCO | 145 | ± | 17 | 3 |
| VHH$_{GFP}$-PEG-PTH(1-11) | No activity at 100 nM | | | 3 |
| VHH$_{6E}$-PEG-PTH(1-11) | No activity at 100 nM | | | 2 |

1 PTH(1-34)
2 PTH(1-14)
3 PTH(1-11)
4 VHH$_{6E}$-PTH(1-11)
5 VHH$_{6E}$-PEG-PTH(1-11)
6 VHH$_{6E}$-PTH(1-14)
7 VHH$_{6E}$-PEG-PTH(1-14)

| Peptide/conjugate | EC$_{50}$, nM (± SD) | | | n |
|---|---|---|---|---|
| PTH(1-34) | 1.3 | ± | 0.98 | 3 |
| PTH(1-14) | 3.4 | ± | 2 | 3 |
| PTH(1-11) | 94 | ± | 74 | 3 |
| VHH$_{8E}$-PTH(1-14) | 0.43 | ± | 0.24 | 3 |
| VHH$_{8E}$-PEG-PTH(1-14) | 0.81 | ± | 0.36 | 3 |
| VHH$_{8E}$-PTH(1-11) | 6.9 | ± | 2.6 | 3 |
| VHH$_{8E}$-PEG-PTH(1-11) | 21 | ± | 9.8 | 3 |

| Peptide/conjugate | EC$_{50}$, nM (± SD) | | | n |
|---|---|---|---|---|
| PTH(1-34) | 0.56 | ± | 0.29 | 3 |
| VHH$_{GFP}$-PEG-PTH(1-34) | 0.52 | ± | 0.12 | 3 |
| VHH$_{8E}$-PEG-PTH(1-34) | 0.83 | ± | 0.29 | 3 |

| Peptide/conjugate | EC$_{50}$ (nM ± SD) | | | n |
|---|---|---|---|---|
| PTH(1-34) | 0.28 | ± | 0.12 | 3 |
| PTH(1-11) | 120.3 | ± | 90.3 | 3 |
| PTH(1-10) | 2466 | ± | 23 | 3 |
| VHH$_{PTHR}$-PTH(1-11) | 3.2 | ± | 0.9 | 3 |
| VHH$_{6E}$-PTH(1-11) | >100 nM | | | 2 |
| VHH$_{GFP}$-PTH(1-11) | >100 nM | | | 2 |

US 11,878,063 B2

ENGINEERED LIGANDS AND USES THEREOF

RELATED APPLICATIONS

This Application claims the benefit under 35 U.S.C. § 119(e) of U.S. Provisional Application Ser. No. 62/814,096, entitled "ENGINEERED LIGANDS AND USES THEREOF" filed on Mar. 5, 2019, the entire contents of which is incorporated herein by reference.

GOVERNMENT SUPPORT

This invention was made with government support under grant No. R01-AI087879 and Cancer Research Institute Irvington Postdoctoral fellowship, grant No. P01DK011794, awarded by the National Institutes of Health. The government has certain rights in this invention.

SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jan. 25, 2022, is named C123370158US01-SEQ-ZGE and is 64,140 bytes in size.

BACKGROUND

The family of chemokine receptors and their ligands control trafficking of cells of hematopoietic origin. Each chemokine receptor can usually bind to multiple chemokines, and each individual chemokine can interact with more than one receptor.

SUMMARY

Described herein are engineered ligands that bind a cell surface receptor, e.g., a G-protein coupled receptor (GPCR), with improved affinity, potency, and/or specificity. For example, a sub-optimal ligand for a cell surface receptor (e.g., GPCR) can be conjugated to a targeting molecule such that the sub-optimal ligand binds to a first binding site on the cell surface receptor (e.g., GPCR) and the targeting molecule binds to a second binding site on the cell surface receptor (e.g., GPCR). It was found surprisingly herein that, such engineered ligand has improved binding affinity to the cell surface receptor (e.g., GPCR) and improved potency in modulating (e.g., activating or repressing) the cell surface receptor (e.g., GPCR), compared to the unmodified sub-optimal ligand. Further, the engineered ligand has improved specificity, i.e., binds to a specific cell surface receptor (e.g., GPCR) instead of promiscuous binding, compared to a natural ligand. Complexes comprising the receptor (e.g., GPCR) and the engineered ligand, and methods of using the engineered ligands are also provided.

Accordingly, some aspects of the present disclosure provide engineered ligands that binds a cell surface receptor, the engineered ligand comprising a sub-optimal ligand conjugated to a targeting molecule, and complexes comprising the engineered ligand associated with the cell surface receptor. In some embodiments, the sub-optimal ligand binds a first binding site of the cell surface receptor and the targeting molecule binds a second binding site of the cell surface receptor.

In some aspects, the present disclosure provide engineered ligands that bind a G-protein coupled receptor (GPCR), the engineered ligand comprising a sub-optimal ligand conjugated to a targeting molecule, and complexes comprising the engineered ligand associated with the GPCR. In some embodiments, the sub-optimal ligand binds a first binding site of the GPCR and the targeting molecule binds a second binding site of the GPCR.

In some embodiments, the sub-optimal ligand is a small molecule. In some embodiments, the sub-optimal ligand is a peptide.

In some embodiments, the GPCR is selected from the group consisting of: chemokine receptors, parathyroid hormone receptor type 1 (PTHR1), parathyroid hormone receptor type 2 (PTHR2), adenosine receptor, calcitonin receptor, Pituitary adenylate cyclase-activating polypeptide type 1, Corticotropin-releasing hormone receptor type 1 and 2, Glucose-dependent insulinotropic polypeptide receptor, Gastric inhibitory polypeptide receptor, Glucagon receptor, Glugacon-like peptide receptor type 1 and 2, Growth hormone releasing hormone receptor, Vasoactive intestinal peptide receptor type 1 and 2, and secretin receptor. In some embodiments, the GPCR is PTHR1. In some embodiments, the suboptimal ligand comprises an N-terminal peptide of parathyroid hormone (PTH), or a variant thereof. In some embodiments, the suboptimal ligand comprises the amino acid sequence of any one of SEQ ID NOs: 5-11 and 48. In some embodiments, the suboptimal ligand comprises an unnatural amino acid. In some embodiments, the unnatural amino acid is 2-aminoisobutyric acid (Aib) homoarginine (Homoarg), or 1-aminocyclopentane-1-carboxylic acid (ACPC). In some embodiments, the unnatural amino acid is at one or more of positions 1, 3, 7, 10, 11, 12 of any one of SEQ ID NO: 5-11, 48, and 85. In some embodiments, suboptimal ligand comprises the amino acid sequence of any one of SEQ ID NOs: 12-47, 49-51, 86-91. In some embodiments, the engineered ligand further comprising a cysteine at the C-terminus.

In some embodiments, the GPCR is a chemokine receptor. In some embodiments, the chemokine receptor is selected from the group consisting of: CXCR1, CXCR2, CCR3, CCR4, CCR5, CCR6, CCR7, CCR8, CCR9, CCR10, XCR1, CXCR3, CXCR4, CXCR5, CXCR6, KSHV, E1, UN12, US28, and ECRF3. In some embodiments, the chemokine receptor is CXCR2. In some embodiments, the sub-optimal ligand is an N-terminal peptide of interleukin 8 (IL8). In some embodiments, the sub-optimal ligand comprises the amino acid sequence of SEQ ID NO: 52.

In some embodiments, the GPCR is an adenosine receptor. In some embodiments, the suboptimal ligand is an adenosine analog.

In some embodiments, the GPCR is a natural GPCR. In some embodiments, the second binding site is an epitope in the extracellular portion of the natural GPCR. In some embodiments, the GPCR is an engineered GPCR. In some embodiments, the GPCR is engineered to contain an exogenous epitope in its extracellular portion. In some embodiments, the second binding site is the exogenous epitope. In some embodiments, the exogenous epitope is a fluorescent protein. In some embodiments, the exogenous epitope is a peptide derived from Ubc6e protein. In some embodiments, the peptide derived from Ubc6e protein comprises the amino acid sequence of any one of SEQ ID NOs: 53-55. In some embodiments, the exogenous epitope comprises the amino acid sequence of SEQ ID NO: 56 or SEQ ID NO: 57. In some embodiments, the exogenous epitope is an HA tag. In some embodiments, the exogenous epitope comprises the amino acid sequence of any one of SEQ ID NOs: 64-66.

In some embodiments, the targeting molecule is an antibody or the antigen binding domain of an antibody. In some embodiments, the antibody is a nanobody (VHH). In some embodiments, the nanobody comprises the amino acid sequence of any one of SEQ ID NOs: 71-75 and 80. In some embodiments, the VHH further comprises a peptide GGLPETGG (SEQ ID NO: 81) at the C-terminus.

In some embodiments, the suboptimal ligand is conjugated to the targeting molecule covalently. In some embodiments, the C-terminus of the suboptimal ligand is conjugated to the C-terminus of the targeting molecule.

In some embodiments, the engineered ligand has increased specificity to the GPCR, compared to a natural ligand for the GPCR. In some embodiments, the engineered ligand has increased or comparable affinity to the GPCR, compared to an optimal ligand for the GPCR.

In some embodiments, the engineered ligand comprises a sub-optimal ligand having the amino acid sequence of AV(Aib)EIQLMHQAKWC (SEQ ID NO: 16) conjugated to VHH22A3, wherein the C-terminus of VHH22A3 is conjugated to the cysteine at the C-terminus of the suboptimal ligand via a PEG linker.

Further provided herein are complexes comprising the engineered ligand described herein associated with the GPCR.

Other aspects of the present disclosure provide compositions comprising the engineered ligand described herein. In some embodiments, the composition further comprises a pharmaceutically acceptable carrier.

Also provided herein are methods of modulating a G-protein coupled receptor (GPCR), the method comprising contacting the engineered ligand described herein with the GPCR. In some embodiments, the contacting is in vitro. In some embodiments, the contacting is in vivo. In some embodiments, the contacting is ex vivo.

Other aspects of the present disclosure provide methods of treating a disease, the method comprising administering to a subject in need thereof a therapeutically effective amount of the engineered ligand or the composition described herein. In some embodiments, the engineered ligand is administered subcutaneous, intramuscular, or intravenously. In some embodiments, the disease is selected from: osteoporosis, hypoparathyroidism, inflammatory diseases, pancreatic cancer, malignant melanoma, HIV/AIDS, cancer immunotherapy, and type-2 diabetes.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

(FIG. 2A) Schematics comparing the modes of interaction for PTH(1-34) (left) or PTH(1-11) (right) with PTHR1. (FIG. 2B) PTH(1-34) is 9000 fold more potent that PTH(1-11) in activating PTHR1.

(FIG. 4A) Graphical overview of producing the engineered ligand described herein by linking VHHs and sub-optimal PTHR1 ligands via a sortase-mediated ligation method. Any functionalities of interest or non-natural residues can also be incorporated into the sub-optimal PTHR1 ligands. (FIG. 4B) Summary of VHHs and their binding targets. VHHs can be recombinantly expressed at high yields in E coli.

FIGS. 7A-7B: Selective binding of VHH to target enables selectivity for nanobody-peptide conjugates in activating signaling at engineered receptors. (FIG. 7A) PTH(1-11) conjugated to VHH05 does not activate engineered PTHR1 with GFP incorporated. (FIG. 7B) PTH(1-11) conjugated to enhancer (i.e., VHH targeting GFP) does not activate engineered PTHR1 with Ubc6e epitope incorporated.

FIG. 8: Use of a construct of PTHR1 in which the natural extracellular domain was replaced by GFP allows for realization of large enhancements in activity (>20,000 fold) for PTH(1-11) when it is conjugated to anti-GFP VHH. PTH (1-9) is inactive alone but became active when conjugated to anti-GFP VHH through introduction of cysteine and ethylene glycol trimer linker at position 7.

FIG. 9: The sub-optimal ligand PTH(1-11) is conjugated to a VHH that binds to an natural epitope in the extracellular portion of PTHR1 (the VHH22A3 described in US Patent Application Publication US 2010/0062004, incorporated herein by reference). The resulting engineered ligand has enhanced activity (65-fold enhancement), compared to PTH (1-11). By using a VHH that targets an natural epitope of PTHR1, the need to engineer the PTHR1 is eliminated.

FIG. 10: Conjugation of the optimal PTHR1 ligand, PTH(1-34), to a VHH diminishes activity regardless of whether the target of the VHH is found on the receptor.

(FIG. 13A) Structure of synthetic peptides used in this study. Residues that differ from human PTH and are derived from the M-PTH structural series are shown in light grey[26]. M-PTH refers to a "modified" analogue developed in past structure-activity relationship studies. The residue denoted "U" corresponds to aminoisobutyric acid (Aib), depicted at right. (FIG. 13B) Synthetic scheme used to prepare PTH-VHH C-to-C terminal fusions. (FIG. 13C) Mass spectra from the preparation of VHH$_{PTHR}$-PTH(1-11) conjugates. Complete lists of mass spectral data for peptides and conjugates are found in FIG. 18 and FIG. 19.

(FIG. 14A) Analysis of VHH binding to PTHR1, PTHR2 and variants by flow cytometry. HEK293 cell lines in suspension were incubated on ice with 100 nM VHH sortagged with Alexafluor647, pelleted by centrifugation, washed and analyzed. Data for PTHR1-GFP is found in FIGS. 17A to 17C. (FIG. 14B) Analysis of VHH binding with microscopy. Adherent HEK293 cells expressing human PTHR1 were stained on ice with 50 nM VHH$_{PTHR}$-tetramethylrhodamine (TMR) and 30 nM PTH(1-20)-fluorescein (FAM) for 30 minutes. Following staining, cells were washed and treated with fixative in preparation for image acquisition either immediately after staining (0 m) or following a 15-minute incubation in medium at room temperature (15 m).

(FIG. 15A) Representative dose-response curves for hPTHR1 activation. Data points indicate mean±SD. Curves result from fitting of a sigmoidal dose-response model to data. (FIG. 15B) Representative dose-response curves for hPTHR2 activation. Data points indicate mean±SD. Curves result from fitting of a sigmoidal dose-response model to data. (FIG. 15C) Tabulation of cAMP induction potencies. Data for hPTHR1 are identical to those in Table 4 and are included here for comparison. Values listed represent EC$_{50}$ values (mean±SD). Each value comes from ≥3 independent experiments. Further details, including the number of replicates for each measurement (n), are reported in Table 5. Note that the x-axes in these graphs differ as peptides exhibit weaker activity for PTHR2.

(FIG. 16A) Schematic of the experiment performed in mice. (FIG. 16B) Measurement of blood ionized calcium levels in mice injected with PTH and conjugates. The double line break represents a discontinuity in the Y-axis. Mice (CD1 females, 11 weeks) were injected subcutaneously with the indicated ligand (Dose=35 nmol/kg). Blood was drawn at the indicated time points and analyzed for ionized calcium levels. Data points indicate mean±standard error of the mean (SEM), n=4, * p=0.005 vs. vehicle. #p=0.015 vs. vehicle. *p=0.038 vs. M-PTH(1-14). ° p=0.008 vs. M-PTH(1-14). The sequence of M-PTH(1-14) used here differs from PTH(1-14) in FIGS. 13A to 13C and is UVUEIQLMHQXAKW (SEQ ID NO: 90) where U is Aib and X is homoarginine.

FIGS. 17A-17C: Use of PTHR1-GFP. (FIG. 17A) Hypothetical structure of PTHR1 with GFP engrafted into exon 2 bound to a GFP binding nanobody. (FIG. 17B) Flow cytometry analysis of cells stably expressing PTHR1-GFP. HEK293 cell lines in suspension were incubated on ice with 100 nM VHH sortagged with Alexafluor647, pelleted by centrifugation, washed and analyzed. The VHH$_{GFP}$ used in this study binds both GFP and YFP, at 100 nM it only weakly stained HEK293 cells stably expressing PTHR1$_{GFP}$. This weak staining is likely related to the inability of VHHGFP to tightly bind the pH-sensitive GFP variant known as pHluorin2 engrafted into the receptor (ref. 19, main text). (FIG. 17C) HEK293 cells stably expressing PTHR1-GFP were treated with varied doses of the indicated peptides or conjugates and activation was assessed by measuring luminescence from a cAMP-activated luciferase variant. Values listed represent EC$_{50}$ values (mean±SD). Each value comes from ≥3 independent experiments. Further details, including the number of replicates for each measurement and the normalized maximal responses induced, are reported in Table 5. "ND" indicates that the measurement was not made. "Inactive" indicates that the luminescence response measured at that concentration was less than 5% of the maximal response induced for that cell line.

FIG. 18: Confirmation of peptide identity using mass spectrometry. Peptides were analyzed by LC/MS as described in methods. Calculated masses ([M+H]$_{calc}$) refers to the monoisotopic mass of a singly protonated species. The masses recorded using mass spectrometry are labeled as [M+H]$_{obs}$.

FIG. 19: Confirmation of VHH-peptide conjugate identity using mass spectrometry. VHH-peptide conjugates were analyzed by LC/MS as described in methods. Deconvolution calculations were used to provide the observed values. MW$_{calc}$ refers to the calculated average molecular weight and MW$_{obs}$ refers to the molecular weight recorded by mass spectrometry.

FIG. 20: Assessment of VHH binding to PTHR1 variants expressed on HEK293 cell lines by flow cytometry. Cells dislodged from tissue culture plates using trypsinization were incubated with varied concentrations of VHHs sortagged with AlexaFluor647 on ice for 1 h. Cells were centrifuged, washed, and analyzed by flow cytometry via gating of intact cells based on forward scatter/side scatter profiles. Data points represent median fluorescent intensity values (mean±SD). Connecting curves are the result of fitting a sigmoidal dose-response model to the data points. The plateau for maximum labeling using VHH$_{PTHR}$ was estimated based on maximal labeling with other VHHs.

(FIG. 21A) Adherent HEK293 cells expressing human PTHR1 were stained on ice with 300 nM VHH$_{6E}$-TMR and 30 nM PTH(1-20)-FAM for 30 minutes. Following staining cells were washed and treated with fixative in preparation for image acquisition either immediately after staining (0 m) or following a 15 minute incubation in medium at room temperature (15 m). (FIG. 21B) Adherent HEK293 cells not expressing PTHR1 were stained with VHH$_{6E}$-TMR and VHH$_{PTHR}$-TMR (300 nM each) and imaged as in panel a.

(FIG. 23A) Schematic comparison of the topology of the two types of conjugates tested. (FIG. 23B) Representative dose-response curves for activation of human PTHR1 by indicated peptides or conjugates run as described in methods. Data points indicate mean±SD and connecting lines result from the fit of a four-parameter sigmoidal dose-response model. (FIG. 23C) Tabulation of cAMP induction potencies.

(FIG. 24A) Scheme describing workflow for cAMP kinetics experiments. cAMP responses were recorded every two minutes following addition of peptide and after washout of free peptide. The time needed for medium removal, washing of cells, and resuspension in fresh medium spans approximately 2 minutes. (FIG. 24B) Representative plots of the kinetics of cAMP-induced signal production (left) and signal cessation after removal of medium containing ligand from (right) hPTHR1 expressing HEK293 cells. Ligands were used at the minimal concentration that stimulated near maximal cAMP responses to minimize effects from non-specific adherence. Data points indicate mean±SD from three replicates. Lines connect data points and only serve to guide the eye. The ligand on phase was omitted from panels c-h but each ligand tested induced a similar cAMP response prior to washout. (FIG. 24C) Ligand off phase following stimulation of cells expressing PTHR1$_{6E}$. (FIG. 24D) Ligand off phase following stimulation of cells expressing PTHR1$_{6E}$. (FIG. 24E) Ligand off phase following stimulation of cells expressing PTHR1$_{6E}$. (FIG. 24F) Ligand off phase following stimulation of cells expressing PTHR1$_{YFP\Delta ECD}$. (FIG. 24G) Ligand off phase following stimulation of cells expressing PTHR1$_{YFP\Delta ECD}$. (FIG. 24H) Ligand off phase following stimulation of cells expressing PTHR1$_{YFP\Delta ECD}$. Data from individual cell lines are separated into separate panels for clarity.

(FIG. 26A) Ligand off phase following stimulation of cells expressing PTHR1$_{YFP\Delta ECD}$. Structure of PTH(1-11) fused to either DBCO or PEG$_3$-DBCO to illustrate connectivity. Atoms corresponding to the PEG linker are highlighted in light grey and an arrow. (b-c) Representative dose-response curves for stimulation of human PTHR1. (FIG. 26B) Insertion of a PEG$_3$ linker does not enable activation of receptors not bound by VHHs by VHH-PTH (1-11) conjugates. (FIG. 26C) Attachment of DBCO or PEG-DBCO to PTH(1-11) does not substantially alter receptor activation properties. (FIG. 26D) Tabulation of experimental results for activation of hPTHR1 by PTH and conjugates. These data are distinct from those presented in Table 4. (FIG. 26E) Representative dose-response curve for stimulation of PTHR1$_{6E}$ by DBCO and PEG-DBCO conjugates of PTH fragments. Insertion of a PEG$_3$ linker does not substantially alter receptor activation properties. (FIG. 26F) Tabulation of experimental results for activation of PTHR1-6E by PTH and conjugates. These data are distinct from those presented in Table 4.

(FIG. 27A) The induction of cAMP responses was assessed in cell lines expressing hPTHR1. (FIG. 27B) The induction of cAMP responses was assessed in cell lines expressing PTHR1$_{6E}$. Representative dose-response curves are shown in which data points indicate mean±SD and connecting lines result from the fit of a four-parameter sigmoidal dose-response model. Composite results are tabulated below the dose-response curves.

(FIG. 28A) Schematic of receptor constructs and targeting strategy. (FIG. 28B) Dose-response curves for cells transfected with indicated constructs. Data points represent mean±SD. Each row of graphs represents data from an independent experiment. Indicated VHH-PTH conjugates were mixed with full-size antibodies at a 3:1 molar ratio prior to addition to transfected cells. X-axis concentrations refer to that of VHH-PTH constructs. Lines on the graph are not from the fitting of a model and only serve to guide the eye. PTH(1-11)-Cys is the same sequence as listed in FIGS. 13A to 13C. M-PTH(1-14) is the same sequence listed in FIGS. 16A to 16B. The sequence of M-PTH(1-11) in this assay is YVUELQLMHQX, SEQ ID NO: 91, where Y is 1-aminocyclopentane-1-carboxylic acid, U is Aib, and X is homoarginine. cAMP response assays were performed as described in methods. The difference in activity between M-PTH(1-11) and PTH(1-11) is in line with previously noted structure-activity relationship studies[1].

(FIG. 29A) HEK293/PTHR1 cells were loaded with FURA2-AM, then stimulated with PTH(1-34) at time zero as described in the methods section. (FIG. 29B) HEK293/PTHR1 cells were loaded with FURA2-AM, then stimulated with VHH$_{PTHR}$-PTH(1-11) at time zero as described in the methods section. (FIG. 29C) HEK293/PTHR1 cells were loaded with FURA2-AM, then stimulated with VHH$_{PTHR}$-PTH(1-14) at time zero as described in the methods section. The shapes and numbers used to represent each concentration are held consistent in each panel. Data points indicate mean±SEM from two independent measurements.

(FIG. 30A) The ligands or VHHs (and concentrations) applied to these cells are PTH(1-34)-TMR (30 nM). Panels show the same field of view with signal for β-arrestin2-YFP. (FIG. 30B) The ligands or VHHs (and concentrations) applied to these cells are PTH(1-34)-TMR (30 nM). Panels show the same field of view with signal for PTH(1-34)-TMR. Note that only a portion of the cells appear to be transfected with PTHR1 as indicated by PTH(1-34)-TMR staining. (FIG. 30C) The ligands or VHHs (and concentrations) applied to these cells are PTH(1-34)-TMR (30 nM). Panels show the same field of view with signal for β-arrestin2-YFP and PTH(1-34)-TMR overlay. Signals for β-arrestin2-YFP and PTH(1-34)-TMR colocalize in puncta (inset). Punctate β-arrestin2-YFP signals are not observed in untransfected (PTH(1-34)-TMR negative) cells (inset, left). (FIG. 30D) The ligands or VHHs (and concentrations) applied to these cells are $VHH_{PTHR}$-PTH(1-14) (100 nM). (FIG. 30E) The ligands or VHHs (and concentrations) applied to these cells are $VHH_{PTHR}$ (100 nM). (FIG. 30F) The ligands or VHHs (and concentrations) applied to these cells are Vehicle. Transfected cells were incubated with indicated ligands or VHHs at room temperature for 30 minutes. This solution was aspirated, and the cells were washed twice, fixed with paraformaldehyde, and imaged as described in methods. For each panel the bottom image corresponds to an expanded version of the inset marked by the rectangle in the top image.

(FIG. 32A) Representative dose-response curve for stimulation of rPTHR1 by peptides or VHH-PTH(1-11) conjugates. Data points indicate mean±SD and connecting lines result from the fit of a four-parameter sigmoidal dose-response model. (FIG. 32B) Tabulation of composite results from rPTHR1 cAMP stimulation assays.

DETAILED DESCRIPTION OF CERTAIN EMBODIMENTS

Figure 1:
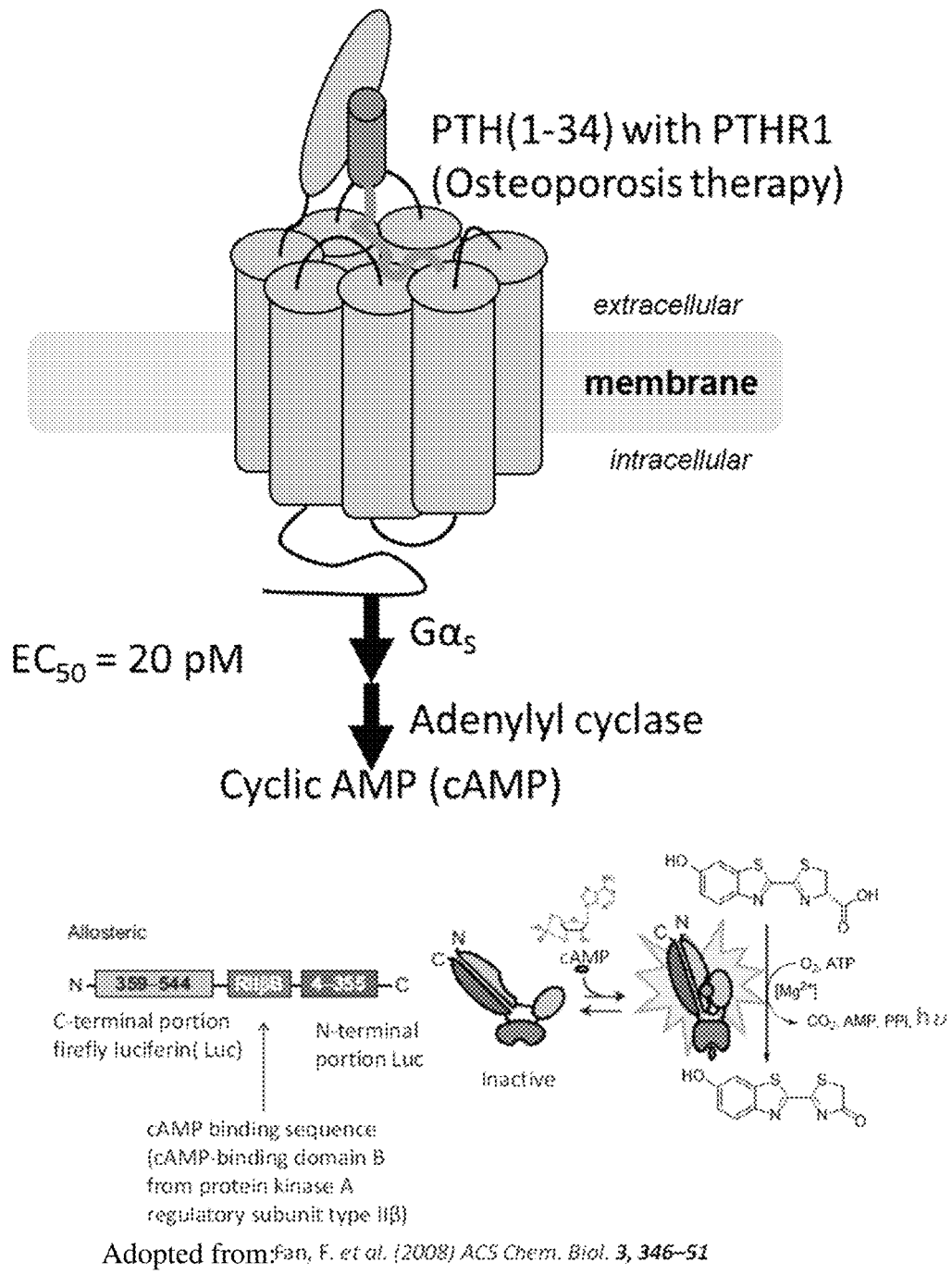
FIG. 1: Activation of PTHR1 signaling pathway. Parathyroid hormone (PTH) residues (1-34) activate PTH-receptor, type 1 (PTHR1) and trigger the downstream signaling cascade.

Described herein are engineered ligands that bind a cell surface receptor, e.g., a G-protein coupled receptor (GPCR), with improved affinity, potency, and/or specificity. For example, a sub-optimal ligand for a cell surface receptor (e.g., GPCR) can be conjugated to a targeting molecule, yielding an engineered ligand that, surprisingly, binds to the cell surface receptor (e.g., GPCR) with enhanced binding affinity and/or potency, compared to the unmodified sub-optimal ligand. Further, the engineered ligand has improved specificity, i.e., binds to a specific cell surface receptor (e.g., GPCR) instead of promiscuous binding, compared to a natural ligand.

Accordingly, some aspects of the present disclosure provide engineered ligands that bind a cell surface receptor, the engineered ligands comprising a sub-optimal ligand conjugated to a targeting molecule.

A "ligand," as used herein, refers to a molecule that specifically binds to and forms a complex with another molecule (e.g., a biomolecule such as a protein). The molecule that is bound by the ligand is herein referred to as a "receptor." In some embodiments, the receptor is a cell surface receptor. The ligand of the present disclosure may be naturally occurring or non-naturally occurring (e.g., obtained by genetic engineering, chemical engineering, or any synthetic methods known to those skilled in the art). The non-naturally occurring ligands are referred to as "engineered ligands" herein. In some embodiments, an engineered ligand is obtained by modifying a naturally occurring ligand. Non-limiting examples of natural occurring ligands include: cytokines, growth factors, hormones, neurotransmitters, and cell recognition molecules.

The binding of a ligand to its receptor may be via intermolecular forces, such as ionic bonds, hydrogen bonds and Van der Waals forces. In some embodiments, binding of a ligand to a receptor protein alters the chemical conformation by affecting the three-dimensional shape orientation. The conformation of a receptor protein composes its functional state. Ligands include substrates, inhibitors, activators, antibodies, and neurotransmitters. The rate of binding is called affinity ($K_D$), and this measurement typifies a tendency or strength of the effect of binding. Binding affinity is actualized not only by host-guest interactions, but also by solvent effects that can play a dominant, steric role which drives non-covalent binding in solution. The solvent provides a chemical environment for the ligand and receptor to adapt, and thus accept or reject each other as partners.

Herein, the ability for a ligand to selectively bind one or a subset of receptors but not all the receptors is termed the "specificity" of the ligand. Ligands that bind to receptors with high specificity bind to one or a selective subgroup of receptors, while ligands that bind to receptors with low specificity (i.e., binding promiscuously) bind to a large number of receptors.

The ability of a ligand to modulate (activate/inhibit) a receptor that it binds to and any downstream signaling pathways is referred to herein as the "potency" of the ligand. In some embodiments, a ligand that binds a receptor with higher affinity may also has higher potency.

The term "bind" refers to the association of two entities (e.g., two proteins). Two entities (e.g., two proteins) are considered to bind to each other when the affinity ($K_D$) between them is $<10^{-3}$ M, $<10^{-4}$ M, $<10^{-5}$ M, $<10^{-6}$ M, $<10^{-7}$ M, $<10^{-8}$ M, $<10^{-9}$ M, $<10^{-10}$ M, $<10^{-11}$ M, or $<10^{-12}$ M. One skilled in the art is familiar with how to assess the affinity of two entities (e.g., two proteins).

A "sub-optimal ligand," as used herein, refers to a ligand that has lower affinity and/or potency with regards to a receptor that it binds to, compared to a known ligand for any given receptor that has high binding affinity and/or potency (also referred to herein as an "optimal ligand"). For example, in some embodiments, the binding affinity of a sub-optimal ligand to its receptor is at least 20%, at least 30%, at least 40%, at least 50%, at least 60%, at least 70%, at least 80%, at least 90%, at least 95%, or at least 99% lower, compared to an optimal ligand for the receptor. In some embodiments, the binding affinity of a sub-optimal ligand to its receptor is 20%, 30%, 40%, 50%, 60%, 70%, 80%, 90%, 95%, or 99% lower, compared to an optimal ligand for the receptor.

In some embodiments, the cell surface receptor of the present disclosure interacts with its ligand at more than one sites (e.g., two sites). The two sites of interaction are referred to herein as a "first target site" and a "second target site." In some embodiments, a ligand (e.g., an optimal ligand) that interacts with the cell surface receptors at both the first target site and the second target site has increased affinity (e.g., increased by at least 20%, at least 30%, at least 30%, at least 40%, at least 50%, at least 60%, at least 70%, at least 80%, at least 90%, at least 100%, at least 2-fold, at least 5-fold, at least 10-fold, at least 100-fold or more) and/or increased potency (e.g., increased by at least 20%, at least 30%, at least 30%, at least 40%, at least 50%, at least 60%, at least 70%, at least 80%, at least 90%, at least 100%, at least 2-fold, at least 5-fold, at least 10-fold, at least 100-fold higher or more), compared to a ligand (e.g., a sub-optimal ligand) that interacts with the cell surface receptors at only one target site. In some embodiments, a ligand (e.g., an optimal ligand) that interacts with the cell surface receptors at both the first target site and the second target site has increased specificity (e.g., increased by at least 20%, at least 30%, at least 30%, at least 40%, at least 50%, at least 60%, at least 70%, at least 80%, at least 90%, at least 100%, at least 2-fold, at least 5-fold, at least 10-fold, at least 100-fold or more), compared to a ligand (e.g., a sub-optimal ligand) that interacts with the cell surface receptors at only one target site.

A "cell surface receptor" refers to a receptor that embedded in the plasma membrane of cells. Cell surface receptors act in cell signaling by receiving (binding to) extracellular molecules (i.e., ligands such as, without limitation, hormones, neurotransmitters, cytokines, growth factors, cell adhesion molecules, or nutrients). They are specialized integral membrane proteins that allow communication between the cell and the extracellular space. Binding of the ligand to a cell surface receptor typically induces changes in the metabolism and activity of a cell.

Cell surface receptors regulate a multitude of biological pathways required for cell growth, differentiation, proliferation, and survival. Non-limiting examples of cell surface receptors include: ion channel-linked receptors, enzyme-linked receptors, and G protein-coupled receptors.

In some embodiments, the cell surface receptor of the present disclosure is an ion channel-linked receptor. An ion channel-linked receptor is a pore-forming protein present in the membranes of all cells. Ions pass through channels down their electrochemical gradient, without the requirement for ATP or metabolic energy. ion channel-linked receptor are especially prominent components of the nervous system, since "transmitter-activated" channels mediate conduction across nerve synapses. ion channel-linked receptor are also key components in the cellular response to toxins and venoms, as well as biological processes that involve rapid changes in cells, such as cardiac, skeletal, and smooth muscle contraction, T-cell activation and hormone release.

In some embodiments, the cell surface receptor of the present disclosure is an enzyme-linked receptor. An enzyme-linked receptor is usually a single-pass transmembrane receptor. This group includes the highly studied receptor tyrosine kinases (RTKs), which bind to polypeptide growth factors that control cell proliferation and differentiation. Also included are receptor serine/threonine kinases, receptor-like tyrosine phosphatases, and receptor guanylyl cyclases that catalyze the production of cyclic GMP in the cytosol.

In some embodiments, the cell surface receptor of the present disclosure is a G-protein-coupled receptor (GPCR). Accordingly, the present disclosure provides engineered ligands that bind a GPCR, the engineered ligands comprising a sub-optimal ligand and a targeting molecule.

A "G-protein-coupled receptors (GPCRs)", also known as 7 transmembrane (7-TM) receptors, are structurally and functionally related proteins characterized by seven membrane-spanning a helices. GPCRs are involved in numerous signaling pathways, including sensory perception (sight, smell, taste, pain). GPCRs are found only in eukaryotes, including yeast, choanoflagellates, and animals. GPCRs are involved in many diseases, and are also the target of approximately 34% of all modern medicinal drugs. According to the classical A-F system (e.g., as described in Attwood et al., Protein Engineering. 7 (2): 195-203, 1994, incorporated herein by reference), GPCRs can be grouped into 6 classes based on sequence homology and functional similarity: Class A (Rhodopsin-like GPCRs), Class B (Secretin receptor family), Class C (Metabotropic glutamate/pheromone receptors), Class D (Fungal mating pheromone receptors), Class (Cyclic AMP receptors), and Class F (Frizzled/Smoothened).

The ligands that bind and activate GPCRs include, without limitation: sensory signal mediators (e.g., light and olfactory stimulatory molecules); adenosine, bombesin, bradykinin, endothelin, γ-aminobutyric acid (GABA), hepatocyte growth factor (HGF), melanocortins, neuropeptide Y, opioid peptides, opsins, somatostatin, GH, tachykinins, members of the vasoactive intestinal peptide family, and vasopressin; biogenic amines (e.g., dopamine, epinephrine, norepinephrine, histamine, serotonin, and melatonin); glutamate (metabotropic effect); glucagon; acetylcholine (muscarinic effect); chemokines; lipid mediators of inflammation (e.g., prostaglandins, prostanoids, platelet-activating factor, and leukotrienes); peptide hormones (e.g., calcitonin, C5a anaphylatoxin, follicle-stimulating hormone (FSH)], gonadotropin-releasing hormone (GnRH), neurokinin, thyrotropin-releasing hormone (TRH), and oxytocin); and endocannabinoids.

None limiting examples of GPCRs that may be used in accordance with the present disclosure include: chemokine receptors, parathyroid hormone receptor type 1 (PTHR1), parathyroid hormone receptor type 2 (PTHR2), adenosine receptor, calcitonin receptor, Pituitary adenylate cyclase-activating polypeptide type 1, Corticotropin-releasing hormone receptor type 1 and 2, Glucose-dependent insulinotropic polypeptide receptor, Gastric inhibitory polypeptide receptor, Glucagon receptor, Glugacon-like peptide receptor type 1 and 2, Growth hormone releasing hormone receptor, Vasoactive intestinal peptide receptor type 1 and 2, and secretin receptor. In some embodiments, the engineered ligand described herein binds parathyroid hormone receptor type 1 (PTHR1). In some embodiments, the engineered ligand described herein binds a chemokine receptor (e.g., CXCR2). In some embodiments, In some embodiments, the engineered ligand described herein binds and adenosine receptor.

In some embodiments, in the engineered ligands of the present disclosure, the sub-optimal ligand binds a first binding site of the cell surface receptor (e.g., a GPCR) and the targeting molecule binds a second binding site of the cell surface receptor (e.g., a GPCR).

In some embodiments, the engineered ligand has increased (e.g., increased by at least 20%, at least 30%, at least 30%, at least 40%, at least 50%, at least 60%, at least 70%, at least 80%, at least 90%, at least 100%, at least 2-fold, at least 5-fold, at least 10-fold, at least 100-fold or more) or comparable (e.g., no more than 30%, no more than 20%, no more than 10%, no more than 5%, no more than 3%, or no more than 1% lower or higher) affinity to the cell surface receptor (e.g., a GPCR), compared to an optimal ligand for the cell surface receptor (e.g., a GPCR).

In some embodiments, the engineered ligand has increased specificity to the cell surface receptor (e.g., a GPCR), compared to a natural ligand for the cell surface receptor (e.g., a GPCR). For example, certain natural GPCR ligands, e.g. chemokines, bind promiscuously. However, the engineered ligands may be engineered such that it binds and activates one specific chemokine receptor, instead of binding and activating multiple chemokine receptors.

Ligands (e.g., optimal ligands or sub-optimal ligand) for cell surface receptors (e.g., GPCRs) may be a small molecule or a peptide. In some embodiments, the engineered ligand of the present disclosure is derived from a natural or synthetic sub-optimal ligand.

A "small molecule," as used herein, refers to a molecule of low molecular weight (e.g., <900 daltons) organic or inorganic compound that may function in regulating a biological process. Non-limiting examples of a small molecule include lipids, monosaccharides, second messengers, other natural products and metabolites, as well as drugs and other xenobiotics.

A "lipid" refers to a group of naturally occurring molecules that include fats, waxes, sterols, fat-soluble vitamins (such as vitamins A, D, E, and K), monoglycerides, diglycerides, triglycerides, phospholipids, and others. A "monosaccharide" refers to a class of sugars (e.g., glucose) that cannot be hydrolyzed to give a simpler sugar. Non-limiting examples of monosaccharides include glucose (dextrose), fructose (levulose) and galactose. A "second messenger" is a molecule that relay signals received at receptors on the cell surface (e.g., from protein hormones, growth factors, etc.) to target molecules in the cytosol and/or nucleus.

Nonlimiting examples of second messenger molecules include cyclic AMP, cyclic GMP, inositol trisphosphate, diacylglycerol, and calcium. A "metabolite" is an molecule that forms as an intermediate produce of metabolism. Non-limiting examples of a metabolite include ethanol, glutamic acid, aspartic acid, 5' guanylic acid, Isoascorbic acid, acetic acid, lactic acid, glycerol, and vitamin B2. A "xenobiotic" is a foreign chemical substance found within an organism that is not normally naturally produced by or expected to be present within. Non-limiting examples of xenobiotics include drugs, antibiotics, carcinogens, environmental pollutants, food additives, hydrocarbons, and pesticides.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

In some embodiments, the engineered ligand described herein binds parathyroid hormone receptor type 1 (PTHR1). A "parathyroid hormone receptor type 1 (PTHR1)" is also referred to herein and in the art as "parathyroid hormone 1 receptor (PTH1R)" and is a protein that in humans is encoded by the PTH1R gene. PTHR1 functions as a receptor for parathyroid hormone (PTH) and is a member of the secretin family of GPCRs. PTHR1 is involved in various biological processes, including regulation of skeletal development, bone turnover, and mineral ion homeostasis.

"Parathyroid hormone (PTH)" is a natural ligand for PTHR1. PTH is a hormone secreted by the parathyroid glands that is important in bone remodeling, which is an ongoing process in which bone tissue is alternately resorbed and rebuilt over time. PTH is secreted in response to low blood serum calcium (Ca2+) levels. Human PTH is secreted by the chief cells of the parathyroid glands as a pre-propeptide containing 115 amino acids (Uniprot Accession No. P01270, SEQ ID NO: 1) and processed into its mature form by removing the signal peptide at the N-terminus. Mature PTH is a polypeptide of 84 amino acids (SEQ ID NO: 2) and the first 34 amino acids of the mature PTH (herein termed PTH(1-34), SEQ ID NO: 3) has been identified as being responsible for interacting with PTHR1. In some embodiments, an optimal PTHR1 ligand used in the present disclosure is PTH(1-34) with a C-terminal cysteine addition (SEQ ID NO: 4).

```
Human PTH precursor (Uniprot accession No. P01270)
                                             (SEQ ID NO: 1)
MIPAKDMAKVMIVMLAICFLTKSDGKSVKKRSVSEIQLMHNLGKHLNSMER

VEWLRKKLQDVHNFVALGAPLAPRDAGSQRPRKKEDNVLVESHEKSLGEAD

KADVNVLTKAKSQ

Mature human PTH
                                             (SEQ ID NO: 2)
SVSEIQLMHNLGKHLNSMERVEWLRKKLQDVHNFVALGAPLAPRDAGSQRP

RKKEDNVLVESHEKSLGEADKADVNVLTKAKSQ

Optimal PTHR1 ligand - PTH(1-34)
                                             (SEQ ID NO: 3)
SVSEIQLMHNLGKHLNSMERVEWLRKKLQDVHNF Optimal PTHR1 ligand with C-terminal cysteine -
PHT(1-34)-Cys
                                             (SEQ ID NO: 4)
SVSEIQLMHNLGKHLNSMERVEWLRKKLQDVHNFC
```

A two-site model of PTH binding to PTHR1 has been shown (e.g., in Bergwitz et al., J. Biol. Chem. 1996; 271: 26469-26472, incorporated herein by reference), where the C-terminal portion of PTH(1-34) (approximately corresponding to residues 15-34) interacts with the amino-terminal extracellular domain of PTHR1, whereas the N-terminal portion (approximately corresponding to residues 1-14) interacts with the transmembrane helices and extracellular connecting loops. The interactions between PTHR1 and PTH residues 15-34 provide the majority of the energetic drive for binding, whereas the interaction between PTHR1 and residues 1-14 of PTH induces the conformational changes in the receptor that initiate intracellular signaling (e.g., as described in Luck et al., Mol. Endocrinol. 1999; 13:670-680, incorporated herein by reference). It has also been shown that PTH(1-11), compared to PTH1-34), has significantly reduced binding affinity to PTHR1 and reduced potency (e.g., as described in Shimizu et al., J Biol Chem. 2000 Jul. 21; 275(29):21836-43, incorporated herein by reference).

The present disclosure, in some embodiments, provide engineered ligands derived from PTH(1-11) by fusing to a targeting molecule. For the purpose of the present disclosure, PTH(1-34) is considered to be an optimal ligand for PTHR1, while N-terminal fragments of PTH that are not the full PTH(1-34) (e.g., PTH(1-9), PTH(1-10), PTH(1-11), and variants thereof) are considered to be sub-optimal ligands for PTHR1.

In some embodiments, the sub-optimal ligand comprises an amino acid sequence that is at least 70%, at least 80%, or at least 90% identical to the amino acid sequence of any one of SEQ ID NOs: 5-11, 48, and 85). In some embodiments, the sub-optimal ligand comprises an amino acid sequence that is 70%, 80%, or 90% identical to the amino acid sequence of any one of SEQ ID NOs: 5-11, 48, and 85). In some embodiments, the sub-optimal ligand comprises the amino acid sequence of any one of SEQ ID NOs: 5-11, 48, and 85. In some embodiments, the sub-optimal ligand consists of the amino acid sequence of any one of SEQ ID NOs: 5-11, 48, and 85.

In some embodiments, the sub-optimal ligand of PTHR1 further comprises an unnatural amino acid. An "unnatural amino acid" is non-proteinogenic amino acids that either occur naturally or are chemically synthesized. In some embodiments, the unnatural amino acid is aminoisobutyric acid (Aib), homoarginine (Homoarg), or 1-aminocyclopentane-1-carboxylic acid (ACPC).

In some embodiments, the unnatural amino acid is incorporated at one or one or more of positions 1, 3, 7, 10, 11, and 12 of any one of SEQ ID NOs: 5-11, 48, and 85. In some embodiments, the unnatural amino acid (e.g., Aib) is incorporated at position 1 of any one of SEQ ID NOs: 5-11, 48, and 85. In some embodiments, the unnatural amino acid (e.g., Aib) is incorporated at position 3 of any one of SEQ ID NOs: 5-11, 48, and 85. In some embodiments, the unnatural amino acid (e.g., Aib) is incorporated at position 7 of any one of SEQ ID NOs: 5-11, 48, and 85. In some embodiments, the unnatural amino acid (e.g., Aib) is incorporated at position 10 of any one of SEQ ID NOs: 5-11, 48, and 85. In some embodiments, the unnatural amino acid (e.g., Aib) is incorporated at position 12 of any one of SEQ ID NOs: 5-11, 48, and 85. In some embodiments, the unnatural amino acid (e.g., Aib) is incorporated at positions 1 and 3 of any one of SEQ ID NOs: 5-11, 48, and 85. In some embodiments, the unnatural amino acid (e.g., Homoarg) is incorporated at position 11 of any one of SEQ ID NOs: 5-11, 48, and 85. In some embodiments, the unnatural amino acid (e.g., ACPC) is incorporated at position 1 of any one of SEQ ID NOs: 5-11, 48, and 85.

In some embodiments, the sub-optimal ligand comprises the amino acid sequence of any one of SEQ ID NOs: 12-47, 49-51, and 86-91. In some embodiments, the sub-optimal ligand consists of the amino acid sequence of any one of SEQ ID NOs: 12-47, 49-51, and 86-91.

In some embodiments, the sub-optimal PTHR1 ligand described herein further comprises a cysteine at the C-terminus. In some embodiments, the sub-optimal PTHR1 ligand comprises the amino acid sequence of any one of SEQ ID NOs: 5-51 and 85-91 and further comprises a cysteine at the C-terminal end. In some embodiments, the sub-optimal ligand consists of the amino acid sequence of any one of SEQ ID NOs: and 85-91 and further comprises a cysteine at the C-terminal end.

In some embodiments, if the sub-optimal ligand already has a cysteine in its sequence, no additional cysteine is added and the already existing cysteine is used for conjugation to the targeting molecule. For example, for the sub-optimal ligand PTH(1-14) Variant—Aib3 (AV(Aib)EIQLMHQAKWC, SEQ ID NO: 16, see Table 1 below), the existing C-terminal cysteine is used for conjugating to the targeting molecule. In another example, for the sub-optimal ligand PTH(1-9) Variant—Aib3 (AV(Aib)EIQCMH, SEQ ID NO: 49, see Table 1 below), position 7 is a cysteine, and the cysteine at position 7 is used for conjugation to the targeting molecule.

Figures 4A, 4B:
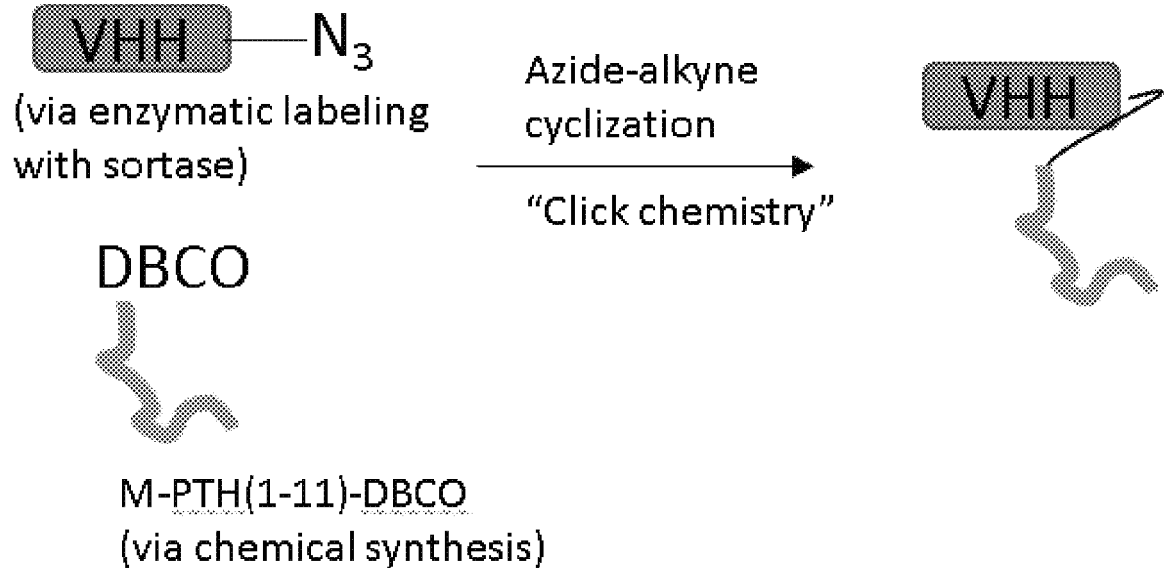
FIG. 4A-4B.
Figure 13A:
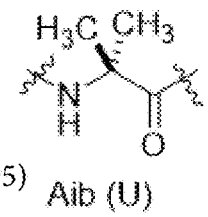
FIGS. 13A-13C: Synthetic peptides and conjugation strategy.
Figure 13B:
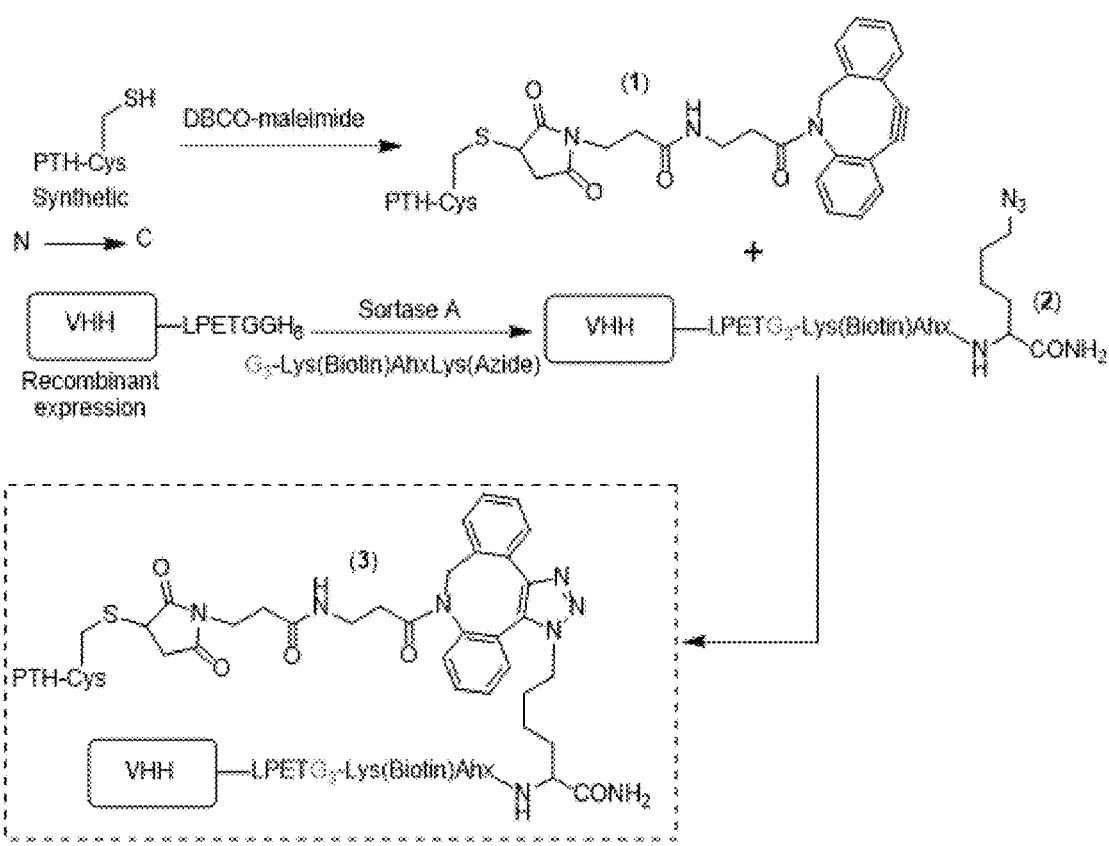

In some embodiments, the C-terminal cysteine or internal cysteine is used for linking the sub-optimal ligand to the targeting molecule, e.g., via a click chemistry handle and/or sortagging (e.g., as illustrated in FIG. 4B and FIG. 13B). It is to be understood that the figure is for illustration purpose only and is not intended to be limiting. One skilled in the art is able to select suitable linking methods or click chemistry handles. In some embodiments, the engineered ligand described herein binds a chemokine receptor. A "chemokine receptor" is a GPCR that specifically bind and respond to cytokines of the CC chemokine family. In some embodiments, the chemokine receptor is selected from the group consisting of: CXCR1, CXCR2, CCR3, CCR4, CCR5, CCR6, CCR7, CCR8, CCR9, CCR10, XCR1, CXCR3, CXCR4, CXCR5, CXCR6, KSHV, E1, UN12, US28, and ECRF3. In some embodiments, the chemokine receptor is C—X—C Motif Chemokine Receptor 2 (CXCR2).

"C—X—C Motif Chemokine Receptor 2 (CXCR2)" is the receptor for interleukin-8 (IL-8). It binds to IL8 with high affinity, and transduces the signal through a G-protein-activated second messenger system and causes the activation of neutrophils. This receptor also binds to chemokine (C—X—C motif) ligand 1 (CXCL1/MGSA), a protein with melanoma growth stimulating activity, and has been shown to be a major component required for serum-dependent melanoma cell growth. In addition, it binds ligands CXCL2, CXCL3, and CXCL5.

In some embodiments, the sub-optimal ligand for a chemokine receptor (e.g., CXCR2) comprises an N-terminal fragment of IL-8. In some embodiments, the sub-optimal ligand comprises an amino acid sequences that is at least 70%, at least 80%, or at least 90% identical to the amino acid sequence of SEQ ID NO: 52. In some embodiments, the sub-optimal ligand comprises the amino acid sequences of SEQ ID NO: 52. In some embodiments, the sub-optimal ligand consists of the amino acid sequences of SEQ ID NO: 52. In some embodiments, the sub-optimal ligand for CXCR2 further comprises an unnatural amino acid and/or a C-terminal cysteine.

In some embodiments, the engineered ligand described herein binds an adenosine receptor. A "adenosine receptor" is a purinergic GPCR with adenosine as endogenous ligand. There are four known types of adenosine receptors in humans: A1, A2A, A2B and A3; each is encoded by a different gene. In some embodiments, the sub-optimal ligand is an adenosine analog that has decreased binding affinity and/or potency, compared to adenosine. In some embodiments, the adenosine analog comprises a functional group for conjugating it to a targeting molecule. For example, a propargyl group to the N6 amine of adenosine for conjugation with a targeting molecule.

Non-limiting, exemplary sub-optimal ligands and their amino acid sequences (if a peptide) are provided in Table 1.

TABLE 1

Non-limiting, exemplary sub-optimal ligands

| Sub-optimal ligand | Amino Acid Sequence | SEQ ID NO | Corresponding cell surface receptor |
|---|---|---|---|
| PTH(1-14) | SVSEIQLMHNLGKH | 5 | PTHR1 |
| PTH(1-11) | SVSEIQLMHNL | 6 | PTHR1 |
| PTH(1-10) | SVSEIQLMHN | 7 | PTHR1 |
| PTH(1-9) | SVSEIQLMH | 8 | PTHR1 |
| PTH(1-14) Variant | AVSEIQLMHQAKWC | 9 | PTHR1 |
| PTH(1-11) Variant | AVSEIQLMHQR | 10 | PTHR1 |
| PTH(1-10) Variant | AVSEIQLMHQ | 11 | PTHR1 |
| PTH(1-9) Variant | AVSEIQCMH | 48 | PTHR1 |
| PTH(1-14) - Aib3 | SV(Aib)EIQLMHNLGKH | 12 | PTHR1 |
| PTH(1-11) - Aib3 | SV(Aib)EIQLMHNL | 13 | PTHR1 |
| PTH(1-10) - Aib3 | SV(Aib)EIQLMHN | 14 | PTHR1 |
| PTH(1-9) - Aib3 | SV(Aib)EIQLMH | 15 | PTHR1 |
| PTH(1-14) Variant - Aib3 | AV(Aib)EIQLMHQAKWC | 16 | PTHR1 |
| PTH(1-11) Variant - Aib3 | AV(Aib)EIQLMHQR | 17 | PTHR1 |
| PTH(1-10) Variant - Aib3 | AV(Aib)EIQLMHQ | 18 | PTHR1 |
| PTH(1-9) Variant - Aib3 | AV(Aib)EIQCMH | 49 | PTHR1 |
| PTH(1-14) - Aib1 | (Aib)VSEIQLMHNLGKH | 19 | PTHR1 |
| PTH(1-11) - Aib1 | (Aib)VSEIQLMHNL | 20 | PTHR1 |
| PTH(1-10) - Aib1 | (Aib)VSEIQLMHN | 21 | PTHR1 |
| PTH(1-9) - Aib1 | (Aib)VSEIQLMH | 22 | PTHR1 |
| PTH(1-14) Variant - Aib1 | (Aib)VSEIQLMHQAKWC | 23 | PTHR1 |
| PTH(1-11) Variant - Aib3 | (Aib)VSEIQLMHQR | 24 | PTHR1 |
| PTH(1-10) Variant - Aib1 | (Aib)VSEIQLMHQ | 25 | PTHR1 |
| PTH(1-9) Variant - Aib1 | (Aib)VSEIQCMH | 50 | PTHR1 |
| PTH(1-14) - Aib7 | SVSEIQ(Aib)MHNLGKH | 26 | PTHR1 |
| PTH(1-11) - Aib7 | SVSEIQ(Aib)MHNL | 27 | PTHR1 |
| PTH(1-10) - Aib7 | SVSEIQ(Aib)MHN | 28 | PTHR1 |
| PTH(1-9) - Aib7 | SVSEIQ(Aib)MH | 29 | PTHR1 |
| PTH(1-14) Variant - Aib7 | AVSEIQ(Aib)MHQAKWC | 30 | PTHR1 |
| PTH(1-11) Variant - Aib7 | AVSEIQ(Aib)MHQR | 31 | PTHR1 |
| PTH(1-10) Variant - Aib7 | AVSEIQ(Aib)MHQ | 32 | PTHR1 |
| PTH(1-14)) - Aib10 | SVSEIQLMH(Aib)LGKH | 33 | PTHR1 |
| PTH(1-11)) - Aib10 | SVSEIQLMH(Aib)L | 34 | PTHR1 |
| PTH(1-10) - Aib10 | SVSEIQLMH(Aib) | 35 | PTHR1 |
| PTH(1-14) Variant - Aib10 | AVSEIQLMH(Aib)AKWC | 36 | PTHR1 |
| PTH(1-11) Variant- Aib10 | AVSEIQLMH(Aib)R | 37 | PTHR1 |

TABLE 1-continued

Non-limiting, exemplary sub-optimal ligands

| Sub-optimal ligand | Amino Acid Sequence | SEQ ID NO | Corresponding cell surface receptor |
|---|---|---|---|
| PTH(1-10) Variant - Aib10 | AVSEIQLMH(Aib) | 38 | PTHR1 |
| PTH(1-14) - Aib12 | SVSEIQLMHNL(Aib)KH | 39 | PTHR1 |
| PTH(1-14) Variant - Aib12 | AVSEIQLMHQA(Aib)WC | 40 | PTHR1 |
| PTH(1-14) - Aib1/Aib3 | (Aib)V(Aib)EIQLMHNLGKH | 41 | PTHR1 |
| PTH(1-11) - Aib1/Aib3 | (Aib)V(Aib)EIQLMHNL | 42 | PTHR1 |
| PTH(1-10) - Aib3 | (Aib)V(Aib)EIQLMHN | 43 | PTHR1 |
| PTH(1-9) - Aib1/Aib3 | (Aib)V(Aib)EIQLMH | 44 | PTHR1 |
| PTH(1-14) Variant - Aib1/Aib3 | (Aib)V(Aib)EIQLMHQAKWC | 45 | PTHR1 |
| PTH(1-11) Variant - Aib1/Aib3 | (Aib)V(Aib)EIQLMHQR | 46 | PTHR1 |
| PTH(1-10) Variant - Aib1/Aib3 | (Aib)V(Aib)EIQLMHQ | 47 | PTHR1 |
| PTH(1-9) Variant - Aib1/Aib3 | (Aib)V(Aib)EIQCMH | 51 | PTHR1 |
| IL-8(1-7) | SAKELRC | 52 | CXCR2 |
| PTH(1-11) Variant 2 | AVSELQLMHQR | 85 | PTHR1 |
| PTH(1-9) Aib3 | AV(Aib)EIQLMH | 86 | PTHR1 |
| PTH(1-10) Aib3 | AV(Aib)EIQLMHQ | 87 | PTHR1 |
| PTH(1-11) Aib3 | AV(Aib)EIQLMHQR | 88 | PTHR1 |
| PTH(1-14) Aib3 | AV(Aib)EIQLMHQRAKW | 89 | PTHR1 |
| PTH(1-14) Variant Aib1/Aib3/homoarg11 | (Aib)V(Aib)EIQLMHQ(Homoarg)AKW | 90 | PTHR1 |
| PTH(1-11) Variant ACPC1/Aib3/Homoarg11 | (ACPC)V(Aib)ELQLMHQ(Homoarg) | 91 | PTHR1 |

The engineered ligands described herein comprises the sub-optimal ligand conjugated to a targeting molecule. A "targeting molecule," as used herein, refers to a molecule that binds a second binding site (a different binding site from the first binding site bound by the sub-optimal ligand) in the cell surface receptor (e.g., a GPCR).

The targeting molecule may be, without limitation, a protein or peptide, a small molecule, or a nucleic acid that binds to an binding site on the cell surface receptor (e.g., a GPCR). Typically, the targeting molecule binds to an epitope in the extracellular domain of the cell surface receptor (e.g., GPCR).

An "antibody" or "immunoglobulin (Ig)" is a large, Y-shaped protein produced mainly by plasma cells that is used by the immune system to neutralize an exogenous substance (e.g., a pathogens such as bacteria and viruses). Antibodies are classified as IgA, IgD, IgE, IgG, and IgM. "Antibodies" and "antibody fragments" include whole antibodies and any antigen binding fragment (i.e., "antigen-binding portion") or single chain thereof. In some embodiments, an antibody is a glycoprotein comprising two or more heavy (H) chains and two or more light (L) chains interconnected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An antibody may be a polyclonal antibody or a monoclonal antibody.

The basic 4-chain antibody unit is a heterotetrameric glycoprotein composed of two identical L chains and two H chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for and F isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, (e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6, incorporated herein by reference).

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ and μ, respectively. The γ and α classes are further divided into subclasses on the basis of relatively minor differences in CH sequence and function, e.g., humans express the following subclasses: IgG1, IgG2, IgG3, IgG4, IgA1, and IgA2.

The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a (3-sheet configuration, connected by three hypervariable regions, which form loops connecting, and in some cases forming part of, the 3-sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest, 5th Ed. Public Health Service, National Institutes of Health, Bethesda, Md. (1991), incorporated herein by reference). The constant domains are not involved directly in binding an antibody to an antigen, but exhibit various effector functions, such as participation of the antibody in antibody dependent cellular cytotoxicity (ADCC).

In some embodiments, the antibody is a monoclonal antibody. A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). Monoclonal antibodies may also be isolated from phage antibody libraries, e.g., using the techniques described in Clackson et al., Nature, 352:624-628 (1991) and Marks et al., J. Mol. Biol., 222:581-597 (1991), incorporated herein by reference.

The monoclonal antibodies described herein encompass "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc.), and human constant region sequences.

In some embodiments, the antibody is a polyclonal antibody. A "polyclonal antibody" is a mixture of different antibody molecules which react with more than one immunogenic determinant of an antigen. Polyclonal antibodies may be isolated or purified from mammalian blood, secretions, or other fluids, or from eggs. Polyclonal antibodies may also be recombinant. A recombinant polyclonal antibody is a polyclonal antibody generated by the use of recombinant technologies. Recombinantly generated polyclonal antibodies usually contain a high concentration of different antibody molecules, all or a majority of (e.g., more than 80%, more than 85%, more than 90%, more than 95%, more than 99%, or more) which are displaying a desired binding activity towards an antigen composed of more than one epitope.

In some embodiments, the antibodies are "humanized" for use in human (e.g., as therapeutics). "Humanized" forms of non-human (e.g., rodent) antibodies are chimeric antibodies that contain minimal sequence derived from the non-human antibody. Humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

In some embodiments, the antibody encompasses an antibody fragment containing the antigen-binding portion of the UBC6e antibody. The antigen-binding portion of an antibody refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (e.g., as described in Ward et al., (1989) Nature 341:544-546, incorporated herein by reference), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883, incorporated herein by reference). Such single chain antibodies are also intended to be encompassed within the term "antigen-binding portion" of an antibody. These antibody fragments are obtained using conventional techniques known to those with skill in the art, and the fragments are screened for utility in the same manner as are full-length antibodies.

In some embodiments, an antibody fragment may be a Fc fragment, a Fv fragment, or a single-change Fv fragment. The Fc fragment comprises the carboxy-terminal portions of both H chains held together by disulfides. The effector functions of antibodies are determined by sequences in the Fc region, which region is also the part recognized by Fc receptors (FcR) found on certain types of cells.

The Fv fragment is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

Single-chain Fv also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding (e.g., as described in Pluckthun in The Pharmacology of Monoclonal Antibodies, vol. 113, Rosenburg and Moore eds., Springer-Verlag, New York, pp. 269-315 (1994); Borrebaeck 1995, incorporated herein by reference).

In some embodiments, the targeting molecule described herein is a heavy chain-only antibody. It is known that Camilids produce heavy chain-only antibodies (e.g., as described in Hamers-Casterman et al., 1992, incorporated herein by reference). The single-domain variable fragments of these heavy chain-only antibodies are termed VHHs or nanobodies. VHHs retain the immunoglobulin fold shared by antibodies, using three hypervariable loops, CDR1, CDR2 and CDR3, to bind to their targets. Many VHHs bind to their targets with affinities similar to conventional full-size antibodies, but possess other properties superior to them. Therefore, VHHs are attractive tools for use in biological research and therapeutics. VHHs are usually between 10 to 15 kDa in size, and can be recombinantly expressed in high yields, both in the cytosol and in the periplasm in *E. coli*. VHHs can bind to their targets in mammalian cytosol.

The targeting molecule binds to a second binding site in the cell surface receptor. In some embodiments, the cell surface receptor (e.g., a GPCR) is a natural cell surface receptor (e.g., natural, unmodified GPCR). In some embodiments, the second binding site is an epitope in the extracellular portion of the natural cell surface receptor (e.g., GPCR). An "extracellular portion" of a cell surface receptor (e.g., GPCR) refers to the portion of the cell surface receptor that are outside of the cytosol and on the surface of the cell (as versus the portion that is inside the cytosol. The extracellular portion of a cell surface receptor (e.g., GPCR) typically contains ligand binding sites. An "epitope" refers to a part of the extracellular portion of the cell surface receptor (e.g., GPCR) that is bound by the targeting molecule. For the purpose of the present disclosure, the targeting molecule can be designed to bind any natural epitope of the extracellular portion of the cell surface receptor (e.g., GPCR) that is accessible.

Targeting molecules (e.g., VHHs) that bind natural epitopes in the extracellular portion of natural cell surface receptors (e.g., GPCRs) are known in the art. For example, US Patent Application US 2010/0062004 (incorporated herein by reference) describes VHHs that bind to epitopes in the extracellular portion of PTHR1, including, e.g., VHH22A3, VHH26F2, VHH33A3, and VHH26A6. In some embodiments, the targeting molecule is VHH22A3 (SEQ ID NO: 74). In another example, VHH that binds to CXCR2 has been described, e.g., the 127D01 VHH described in PCT Application Publication WO2012062713, incorporated herein by reference. In some embodiments, the targeting molecule is 127D01 (SEQ ID NO: 75).

In some embodiments, the cell surface receptor (e.g., GPCR) is an engineered cell surface receptor (e.g., engineered GPCR). For example, the cell surface receptor (e.g., GPCR) may be engineered such that an exogenous epitope is incorporated into the extracellular portion of the cell surface receptor (e.g., GPCR) as the second binding site for binding of the targeting molecule. An "exogenous epitope" refers to a peptide sequence that is not from the natural cell surface receptor (e.g., GPCR) protein but is from an exogenous source.

In some embodiments, the exogenous epitope is a fluorescent protein or a fragment thereof. Non-limiting examples of fluorescent proteins include: GFP, YFP, and CFP. In some embodiments, the targeting molecule is an antibody (e.g., a VHH) that binds to the fluorescent protein (e.g., SEQ ID NO: 73). Antibodies (e.g., Fabs, monoclonal antibodies, ScFvs, and VHHs) that bind to fluorescent proteins are known in to those skilled in art and commercially available.

In some embodiments, the exogenous epitope is a peptide derived from Ubc6e protein. In some embodiments, the targeting molecule is an antibody (e.g., a VHH) that binds to the UBc6e epitope. For example, UBc6e epitopes and VHHs that bind to these epitopes have been described in Ling et al., hdl.handle.net/1721.1/115809, incorporated by reference. In some embodiments, the exogenous epitope is selected from: QADQEAKELARQIS (SEQ ID NO: 53), QADEAKELARQI (SEQ ID NO: 54), and QADEAKELARQ (SEQ ID NO:55). In some embodiments, the targeting molecule in the engineered ligand is VHH05 (SEQ ID NO: 71), as described in Ling et al.

In some embodiments, the exogenous epitope is a peptide that, when bound to a VHH, is clamped in a headlock fashion (thus herein termed a "headlock peptide"). Headlock peptides and their binding VHHs have been described in the art, e.g., in Braun et al., Sci Rep. 2016; 6: 19211, incorporated herein by reference. In some embodiments, the exogenous epitope is selected from PDRKAAVSHWQQ (SEQ ID NO: 56) and PDRVRAVSHWSS (SEQ ID NO: 57). In some embodiments, In some embodiments, the targeting molecule in the engineered ligand is BC2-Nb (SEQ ID NO: 72), as described in Braun et al. Other known protein tags (e.g., affinity tags) may also be used as the exogenous epitope of the present disclosure. Non-limiting, exemplary protein tags that may be used as the exogenous epitope that can be integrated into the extracellular portion of the cell surface receptor (e.g., GPCR) for binding by the targeting molecule are provided in Table 2. In some embodiments, the targeting molecule is a VHH that comprises the amino acid sequence of any one of SEQ ID NOs: 71-75 and 80. In some embodiments, the VHH comprises the amino acid sequence of any one of SEQ ID NOs: 71-75 and 80 and further comprises a peptide at the C-terminus GGLPETGG (SEQ ID NO: 81). In some embodiments, any one of the VHHs provided herein further comprises a peptide tag for affinity purification, e.g., the His6 tag.

TABLE 2

Non-limiting, exemplary exogenous epitopes

| Exogenous epitope | Exogenous epitope amino acid sequence | Targeting molecule (e.g., VHH) that binds the exogenous epitope |
|---|---|---|
| Ubc6e epitope 1 | QADQEAKELARQIS (SEQ ID NO: 53) | VHH005 |
| Ubc6e epitope 2 | QADEAKELARQI (SEQ ID NO: 54) | VHH005 |
| Ubc6e epitope 3 | QADEAKELARQ (SEQ ID NO: 55) | VHH005 |
| Headlock peptide 1 | PDRKAAVSHWQQ (SEQ ID NO: 56) | BC2-Nb |
| Headlock peptide 2 | PDRVRAVSHWSS (SEQ ID NO: 57) | BC2-Nb |
| YFP | TMVSKGEELFTGVVPILVELDGDVNGH KFSVSGEGEGDATYGKLTLKLICTTGKL PVPWPTLVTTLGYGVQCFARYPDHMKQ HDFFKSAMPEGYVQERTIFFKDDGNYKT RAEVKFEGDTLVNRIELKGIDFKEDGNIL GHKLEYNYNSHNVYITADKQKNGIKAN FKIRHNIEDGGVQLADHYQQNTPIGDGP VLLPDNHYLSYQSKLSKDPNEKRDHMV LLEFVTAAGITLGMDELYK (SEQ ID NO: 58) | YFP-VHH |
| 6E tag | QADQEAKELARQIS (SEQ ID NO: 59) | Anti-6E |
| CBP | KRRWKKNFIAVSAANRFKKISSSGAL (SEQ ID NO: 60) | Anti-CBP |
| FLAG | DYKDDDD (SEQ ID NO: 61) or DYKDDDDK (SEQ ID NO: 62) or DYKDDDK (SEQ ID NO: 63) | Anti-Flag |
| HA | YPYDVPDYA (SEQ ID NO: 64) or YAYDVPDYA (SEQ ID NO: 65) or YDVPDYASL (SEQ ID NO: 66) | Anti-HA |
| Myc | EQKLISEEDL (SEQ ID NO: 67) | Anti-Myc |
| His6 | HHHHHH (SEQ ID NO: 68) | Anti-His6 |
| S-tag | KETAAAKFERQHMDS (SEQ ID NO: 69) | Anti-S-tag |
| V5 | GKPIPNPLLGLDST (SEQ ID NO: 70) | Anti-V5 |

VHH05

(SEQ ID NO: 71)
QVQLQESGGGLVQPGGSLRLSCAASGFVFENSAMAWYRQAPGKERELIAVI

GTTFIKLAESVKGRFTISRDNAKSTVYLQMNNLKPEDTAVYYCSKSGAYWG

QGTQVTVSS

VHH Headlock (BC2-Nb)

(SEQ ID NO: 72)
QVQLVESGGGLVQPGGSLTLSCTASGFTLDHYDIGWFRQAPGKEREGVSCI

NNSDDDTYYADSVKGRFTIFMNNAKDTVYLQMNSLKPEDTAIYYCAEARGC

KRGRYEYDFWGQGTQVTVSS

VHH Enhancer (binds GFP and YFP)

(SEQ ID NO: 73)
QVQLQESGGALVQPGGSLRLSCAASGFPVNRYSMRWYRQAPGKEREWVAGM

SSAGDRSSYEDSVKGRFTISRDDARNTVYLQMNSLKPEDTAVYYCNVNVGF

EYWGQGTQVTVSS

VHH22A3 (anti-PTHR1)

(SEQ ID NO: 74)
EVQLVESGGGLVQAGGSLRLSCAASGNIFANNIMGWYRQPPGKEREFVAHV

SHDGDSMYAVSVKGRFAISRKDATNLYLQMNSLKPEDTAIYFCRLLNIPTQ

GRMEGFWGQGTQVTVSS

127D01 (anti CXCR2)

(SEQ ID NO: 75)
EVQLVESGGGLVQAGESLRLSCAASGSTFDFKVMGWYRQPPGKQREGVAAI

RLSGNMHYAESVKGRFAISKANAKNTVYLQMNSLRPEDTAVYYCKVNIRGQ

DYWGQGTQVTVSSVSS

VHH-Kappa (SEQ ID NO: 80)
QVQLVESGGGWVQPGGSLRLSCAASGFTFSDTAMMWVRQAPGKGREWVAAI

DTGGGYTYYADSVKGRFTISRDNAKNTLYLQMNSLKPEDTARYYCAKTYSG

NYYSNYTVANYGTTGRGTLVTVSS

Non-limiting, exemplary cell surface receptors (e.g., GPCRs) that are engineered to contain exogenous epitopes in the extracellular portion are provided in Table 3.

TABLE 3

Non-limiting, exemplary natural/engineered GPCRs

| Receptors | Amino Acid sequence | SEQ ID NO |
|---|---|---|
| Human PTHR1 WT | MGTARIAPGLALLLCCPVLSSAYALVDADDVMTKE EQIFLLHRAQAQCEKRLKEVLQRPASIMESDKGWT SASTSGKPRKDKASGKLYPESEEDKEAPTGSRYRGR PCLPEWDHILCWPLGAPGEVVAVPCPDYIYDFNHK GHAYRRCDRNGSWELVPGHNRTWANYSECVKFLT NETREREVFDRLGMIYTVGYSVSLASLTVAVLILAY FRRLHCTRNYIHMHLFLSFMLRAVSIFVKDAVLYSG ATLDEAERLTEEELRAIAQAPPPPATAAAGYAGCRV AVTFFLYFLATNYYWILVEGLYLHSLIFMAFFSEKK YLWGFTVFGWGLPAVFVAVWVSVRATLANTGCW DLSSGNKKWIIQVPILASIVLNFILFINIVRVLATKLR ETNAGRCDTRQQYRKLLKSTLVLMPLFGVHYIVFM ATPYTEVSGTLWQVQMHYEMLFNSFQGFFVAIIYC FCNGEVQAEIKKSWSRWTLALDFKRKARSGSSSYS YGPMVSHTSVTNVGPRVGLGLPLSPRLLPTATTNG HPQLPGHAKPGTPALETLETTPPAMAAPKDDGFLN GSCSGLDEEASGPERPPALLQEEWETVM | 76 |
| Human PTHR1- delNT-YFP | MGTARIAPGLALLLCCPVLSSAYALATMVSKGEEL FTGVVPILVELDGDVNGHKFSVSGEGEGDATYGKL TLKLICTTGKLPVPWPTLVTTLGYGVQCFARYPDH MKQHDFFKSAMPEGYVQERTIFFKDDGNYKTRAE VKFEGDTLVNRIELKGIDFKEDGNILGHKLEYNYNS HNVYITADKQKNGIKANFKIRHNIEDGGVQLADHY QQNTPIGDGPVLLPDNHYLSYQSKLSKDPNEKRDH MVLLEFVTAAGITLGMDELYKGSGEVFDRLGMIYT VGYSVSLASLTVAVLILAYFRRLHCTRNYIHMHLFL SFMLRAVSIFVKDAVLYSGATLDEAERLTEEELRAI AQAPPPPATAAAGYAGCRVAVTFFLYFLATNYYWI LVEGLYLHSLIFMAFFSEKKYLWGFTVFGWGLPAV FVAVWVSVRATLANTGCWDLSSGNKKWIIQVPILA SIVLNFILFINIVRVLATKLRETNAGRCDTRQQYRKL LKSTLVLMPLFGVHYIVFMATPYTEVSGTLWQVQM HYEMLFNSFQGFFVAIIYCFCNGEVQAEIKKSWSRW TLALDFKRKARSGSSSYSYGPMVSHTSVTNVGPRV GLGLPLSPRLLPTATTNGHPQLPGHAKPGTPALETL ETTPPAMAAPKDDGFLNGSCSGLDEEASGPERPPAL LQEEWETV | 77 |
| Human PTHR1- Ubc6e epitope | MGTARIAPGLALLLCCPVLSSAYALVDADDVMTKE EQIFLLHRAQAQCEKRLKEVLQRPASIMESDKGWT QADQEAKELARQISGKLYPESEEDKEAPTGSRYRG RPCLPEWDHILCWPLGAPGEVVAVPCPDYIYDFNH KGHAYRRCDRNGSWELVPGHNRTWANYSECVKFL TNETREREVFDRLGMIYTVGYSVSLASLTVAVLILA | 78 |

TABLE 3-continued

Non-limiting, exemplary natural/engineered GPCRs

| Receptors | Amino Acid sequence | SEQ ID NO |
|---|---|---|
| | YFRRLHCTRNYIHMHLFLSFMLRAVSIFVKDAVLYS<br>GATLDEAERLTEEELRAIAQAPPPPATAAAGYAGCR<br>VAVTFFLYFLATNYYWILVEGLYLHSLIFMAFFSEK<br>KYLWGFTVFGWGLPAVFVAVWVSVRATLANTGC<br>WDLS S GNKKWIIQVPILASIVLNFILFINIVRVLATKL<br>RETNAGRCDTRQQYRKLLKSTLVLMPLFGVHYIVF<br>MATPYTEVSGTLWQVQMHYEMLFNSFQGFFVAIIY<br>CFCNGEVQAEIKKSWSRWTLALDFKRKARSGSSSY<br>SYGPMVSHTSVTNVGPRVGLGLPLSPRLLPTATTNG<br>HPQLPGHAKPGTPALETLETTPPAMAAPKDDGFLN<br>GSCSGLDEEASGPERPPALLQEEWETVM | |
| hPTHR1-GFP | MGTARIAPGLALLLCCPVLSSAYALVDADDVMTKE<br>EQIFLLHRAQAQCEKRLKEVLQRPASIMESDKGWT<br>SASTSGKPRKDKASGKLYPESEEDKMSKGEELFTG<br>VVPILVELDGDVNGHKFSVSGEGEGDATYGKLTLK<br>FICTTGKLPVPWPTLVTTLSYGVQCFSRYPDHMKQ<br>HDFFKSAMPEGYVQERTIFFKDDGNYKTRAEVKFE<br>GDTLVNRIELKGIDFKEDGNILGHKLEYNYNEHLVY<br>IMADKQKNGTKAIFQVHHNIEDGSVQLADHYQQNT<br>PIGDGPVLLPDNHYLHTQSALSKDPNEKRDHMVLL<br>EFVTAAGITHGMDELYKEAPTGSRYRGRPCLPEWD<br>HILCWPLGAPGEVVAVPCPDYIYDFNHKGHAYRRC<br>DRNGSWELVPGHNRTWANYSECVKFLTNETRERE<br>VFDRLGMIYTVGYSVSLASLTVAVLILAYFRRLHCT<br>RNYIHMHLFLSFMLRAVSIFVKDAVLYSGATLDEA<br>ERLTEEELRAIAQAPPPPATAAAGYAGCRVAVTFFL<br>YFLATNYYWILVEGLYLHSLIFMAFFSEKKYLWGF<br>TVFGWGLPAVFVAVWVSVRATLANTGCWDLSSGN<br>KKWIIQVPILASIVLNFILFINIVRVLATKLRETNAGR<br>CDTRQQYRKLLKSTLVLMPLFGVHYIVFMATPYTE<br>VSGTLWQVQMHYEMLFNSFQGFFVAIIYCFCNGEV<br>QAEIKKSWSRWTLALDFKRKARSGSSSYSYGPMVS<br>HTSVTNVGPRVGLGLPLSPRLLPTATTNGHPQLPGH<br>AKPGTPALETLETTPPAMAAPKDDGFLNGSCSGLD<br>EEASGPERPPALLQEEWETVM | 82 |
| rPTHR1-delNT26-181 | MGAARIAPSLALLLCCPVLSSAYALEVFDRLGMIYT<br>VGYSMSLASLTVAVLILAYFRRLHCTRNYIHMHMF<br>LSFMLRAASIFVKDAVLYSGFTLDEAERLTEEELHII<br>AQVPPPPAAAAVGYAGCRVAVTFFLYFLATNYYWI<br>LVEGLYLHSLIFMAFFSEKKYLWGFTIFGWGLPAVF<br>VAVWVGVRATLANTGCWDLSSGHKKWIIQVPILAS<br>VVLNFILFINIIRVLATKLRETNAGRCDTRQQYRKLL<br>RSTLVLVPLFGVHYTVFMALPYTEVSGTLWQIQMH<br>YEMLFNSFQGFFVAIIYCFCNGEVQAEIRKSWSRWT<br>LALDFKRKARSGSSSYSYGPMVSHTSVTNVGPRAG<br>LSLPLSPRLPPATTNGHSQLPGHAKPGAPATETETLP<br>VTMAVPKDDGFLNGSCSGLDEEASGSARPPPLLQE<br>GWETVM | 83 |
| rPTHR1-delNT-HA | MGAARIAPSLALLLCCPVLSSAYPYDVPDYAGGGG<br>EVFDRLGMIYTVGYSMSLASLTVAVLILAYFRRLHC<br>TRNYIHMHMFLSFMLRAASIFVKDAVLYSGFTLDE<br>AERLTEEELHIIAQVPPPPAAAAVGYAGCRVAVTFF<br>LYFLATNYYWILVEGLYLHSLIFMAFFSEKKYLWG<br>FTIFGWGLPAVFVAVWVGVRATLANTGCWDLSSG<br>HKKWIIQVPILASVVLNFILFINIIRVLATKLRETNAG<br>RCDTRQQYRKLLRSTLVLVPLFGVHYTVFMALPYT<br>EVSGTLWQIQMHYEMLFNSFQGFFVAIIYCFCNGEV<br>QAEIRKSWSRWTLALDFKRKARSGSSSYSYGPMVS<br>HTSVTNVGPRAGLSLPLSPRLPPATTNGHSQLPGHA<br>KPGAPATETETLPVTMAVPKDDGFLNGSCSGLDEE<br>ASGSARPPPLLQEGWETVM | 84 |

In the engineered ligand described herein, the sub-optimal ligand is conjugated to the targeting molecule (e.g., a VHH). In some embodiments, the sub-optimal ligand is conjugated to the targeting molecule covalently. Methods of covalently conjugating two molecules are known to those skilled in the art. For example, two polypeptides may be fused via genetic engineering. A polypeptide may also be conjugated to a peptide or a non-peptide molecule via chemical crosslinking. In some embodiments, reactive chemical groups (e.g., click chemistry handles) may be incorporated into the sub-optimal ligand and/or the targeting molecule for chemical conjugation of the two molecules.

Click chemistry is a chemical approach introduced by Sharpless in 2001 and describes chemistry tailored to generate substances quickly and reliably by joining small units together. See, e.g., Kolb, Finn and Sharpless Angewandte Chemie International Edition (2001) 40: 2004-2021; Evans, Australian Journal of Chemistry (2007) 60: 384-395). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiol-yne addition; imine formation; and Michael additions (e.g., maleimide addition). Non-limiting examples of a click chemistry handle include an azide handle, an alkyne handle, or an aziridine handle. Azide is the anion with the formula N3−. It is the conjugate base of hydrazoic acid (HN3). N3− is a linear anion that is isoelectronic with CO2, NCO−, N2O, NO2+ and NCF. Azide can be described by several resonance structures, an important one being —N=N+=N—. An alkyne is an unsaturated hydrocarbon containing at least one carbon-carbon triple bond. The simplest acyclic alkynes with only one triple bond and no other functional groups form a homologous series with the general chemical formula CnH2n−2. Alkynes are traditionally known as acetylenes, although the name acetylene also refers specifically to C2H2, known formally as ethyne using IUPAC nomenclature. Like other hydrocarbons, alkynes are generally hydrophobic but tend to be more reactive. Aziridines are organic compounds containing the aziridine functional group, a three-membered heterocycle with one amine group (—NH—) and two methylene bridges (—CH2-). The parent compound is aziridine (or ethylene imine), with molecular formula C2H5N.

Other non-limiting, exemplary reactive groups include: acetals, ketals, hemiacetals, and hemiketals, carboxylic acids, strong non-oxidizing acids, strong oxidizing acids, weak acids, acrylates and acrylic acids, acyl halides, sulfonyl halides, chloroformates, alcohols and polyols, aldehydes, alkynes with or without acetylenic hydrogen amides and imides, amines, aromatic, amines, phosphines, pyridines, anhydrides, aryl halides, azo, diazo, azido, hydrazine, and azide compounds, strong bases, weak bases, carbamates, carbonate salts, chlorosilanes, conjugated dienes, cyanides, inorganic, diazonium salts, epoxides, esters, sulfate esters, phosphate esters, thiophosphate esters borate esters, ethers, soluble fluoride salts, fluorinated organic compounds, halogenated organic compounds, halogenating agents, aliphatic saturated hydrocarbons, aliphatic unsaturated hydrocarbons, hydrocarbons, aromatic, insufficient information for classification, isocyanates and isothiocyanates, ketones, metal hydrides, metal alkyls, metal aryls, and silanes, alkali metals, nitrate and nitrite compounds, inorganic, nitrides, phosphides, carbides, and silicides, nitriles, nitro, nitroso, nitrate, nitrite compounds, organic, non-redox-active inorganic compounds, organometallics, oximes, peroxides, organic, phenolic salts, phenols and cresols, polymerizable compounds, quaternary ammonium and phosphonium salts, strong reducing agents, weak reducing agents, acidic salts, basic salts, siloxanes, inorganic sulfides, organic sulfides, sulfite and thiosulfate salts, sulfonates, phosphonates, organic thiophosphonates, thiocarbamate esters and salts, and dithiocarbamate esters and salts. In some embodiments, the reactive group is a carboxylic acid group.

In some embodiments, the click chemistry handle is dibenzocyclooctyne group (DBCO). In some embodiments, the DBCO is attached to a cysteine in the sub-optimal ligand (e.g., the Cys added at the C-terminus of a sub-optimal ligand) using maleimide with an intervening linker of PEG3 (DBCO-PEG3-Mal, Catalog #CP-2030, Conju-Probe, LLC, California). This process is illustrated in FIG. 4A and FIG. 13B. The DBCO-PEG3-Mal linker may be used for conjugating any one of the sub-optimal ligands to any one of the targeting molecules described herein. Conjugation carried out using DBCO-PEG3-Mal results in a PEG linker between the sub-optimal ligand and the targeting molecule.

In some embodiments, the sub-optimal ligand is a peptide, and the targeting molecule is fused to the N-terminus of the sub-optimal ligand. In some embodiments, the sub-optimal ligand is a peptide and an unmodified N-terminus of the peptide is required for binding to its receptor, the targeting molecule is fused to the C-terminus of the sub-optimal ligand. In some embodiments, the sub-optimal ligand is fused at the C-terminus to the C-terminus of the targeting molecule (e.g., as demonstrated in FIG. 4A). Methods of fusing the C-termini of two peptides (e.g., via a sortase-mediated peptide ligation process) have been described in the art, e.g., in PCT Application Publication WO2013155526, incorporated herein by reference).

In some embodiments, the engineered ligand binds PTHR1, and comprises a sub-optimal ligand selected from SEQ ID NOs: 5-51 and 85-91, conjugated to a VHH targeting a natural epitope in the extracellular portion of PTHR1 (e.g., VHH22A3 of SEQ ID NO: 74). In some embodiments, the engineered ligand binds PTHR1, and comprises a sub-optimal ligand selected from SEQ ID NOs: 5-51 and 85-91 and further comprises a cysteine at the C-terminus, conjugated to VHH22A3 (SEQ ID NO: 74) via a PEG linker.

In some embodiments, the engineered ligand binds PTHR1, and comprises a sub-optimal ligand having the amino acid sequence of AV(Aib)EIQLMHQAKWC (SEQ ID NO: 16) conjugated to VHH22A3, wherein the C-terminus of VHH22A3 is conjugated to the cysteine at the C-terminus of the suboptimal ligand via a PEG linker. In some embodiments, the VHH22A3 comprises the amino acid sequence of SEQ ID NO: 74.

In some embodiments, the engineered ligand binds PTHR1, and comprises a sub-optimal ligand of SEQ ID NO: 17 and further comprises a cysteine at the C-terminus, fused to the C-terminus of VHH22A3 via a PEG linker, wherein the VHH22A3 is fused to the cysteine at the C-terminus. In some embodiments, the VHH22A3 comprises the amino acid sequence of SEQ ID NO: 74.

In some embodiments, the engineered ligand binds PTHR1, and comprises a sub-optimal ligand of SEQ ID NO: 49, fused to the C-terminus of VHH22A3 via a PEG linker, wherein the VHH22A3 is fused to the cysteine at position 7 of SEQ ID NO: 49. In some embodiments, the VHH22A3 comprises the amino acid sequence of SEQ ID NO: 74.

In some embodiments, the engineered ligand binds PTHR1, and comprises a sub-optimal ligand selected from SEQ ID NOs: 5-51 and 85-91, fused to a VHH targeting a fluorescent protein (e.g., GFP or YFP). In some embodiments, the VHH comprises and amino acid sequences of SEQ ID NO:73. In some embodiments, the PTHR1 is engineered such that a GFP or YFP is incorporated in the extracellular portion of PTHR1. In some embodiments, the engineered PTHR1 comprises an amino acid sequence that is at least 70%, at least 80%, at least 90%, at least 95%, or at least 99% identical to the amino acid sequence of SEQ ID NO: 77 or 82. In some embodiments, the engineered PTHR1 comprises the amino acid sequence of SEQ ID NO: 77 or 82. In some embodiments, the engineered PTHR1 consists of the amino acid sequence of SEQ ID NO: 77 or 82.

In some embodiments, the engineered ligand binds PTHR1, and comprises a sub-optimal ligand selected from SEQ ID NOs: 5-51 and 85-91, fused to a VHH targeting a Ubc6e (e.g., VHH05). In some embodiments, the VHH comprises and amino acid sequences of SEQ ID NO: 70. In some embodiments, the PTHR1 is engineered such that an Ubc6e epitope (e.g., Ubc6e epitope of SEQ ID NO: 1) is incorporated in the extracellular portion of PTHR1. In some embodiments, the engineered PTHR1 comprises an amino acid sequence that is at least 70%, at least 80%, at least 90%, at least 95%, or at least 99% identical to the amino acid sequence of SEQ ID NO: 78. In some embodiments, the engineered PTHR1 comprises the amino acid sequence of SEQ ID NO: 78. In some embodiments, the engineered PTHR1 consists of the amino acid sequence of SEQ ID NO: 78.

In some embodiments, the engineered ligand binds PTHR1, and comprises a sub-optimal ligand selected from SEQ ID NOs: 5-51 and 85-91, fused to a VHH targeting kappa light chain, which than binds to an anti-HA antibody and indirectly tethers the ligand to en engineered PTHR1 having the ECD replaced by an HA peptide. In some embodiments, the VHH comprises and amino acid sequences of SEQ ID NO: 80. In some embodiments, the PTHR1 is engineered such that an HA epitope (e.g., SEQ ID NOs: 64-66) replaces the extracellular portion of PTHR1. In some embodiments, the engineered PTHR1 comprises an amino acid sequence that is at least 70%, at least 80%, at least 90%, at least 95%, or at least 99% identical to the amino acid sequence of SEQ ID NO: 84. In some embodiments, the engineered PTHR1 comprises the amino acid sequence of SEQ ID NO: 84. In some embodiments, the engineered PTHR1 consists of the amino acid sequence of SEQ ID NO: 84.

Other aspects of the present disclosure provide complexes comprising any one of the engineered ligand described associated with the cell surface receptor (e.g., GPCR) that it binds to. In some embodiments, the complex comprises an engineered PTHR1 ligand and PTHR1. In some embodiments, the complex comprises an engineered chemokine receptor ligand and a chemokine receptor. In some embodiments, the complex comprises an engineered adenosine receptor ligand and an adenosine receptor.

Other aspects of the present disclosure provide methods of modulating (activating or repressing) a cell surface receptor (e.g., GPCR), the method comprising contacting the engineered ligand described herein with the a cell surface receptor (e.g., GPCR). The contacting may be in vitro, in vivo, or ex vivo.

Other aspects of the present disclosure provide methods of treating a disease, the method comprising administering to a subject in need thereof a therapeutically effective amount of any one of the engineered ligand described herein.

In some embodiments, the engineered ligand described herein is formulated in one or more compositions for administration to the subject. In some embodiments, the composition is a pharmaceutical composition. In some embodiments, the composition further comprises a pharmaceutically acceptable carrier. The term "pharmaceutically-acceptable carrier", as used herein, means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the agents described herein from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, the engineered ligand described herein, or composition(s) containing the engineered ligand is administered by injection, by means of a catheter, by means of a suppository, or by means of an implant, the implant being of a porous, non-porous, or gelatinous material, including a membrane, such as a sialastic membrane, or a fiber. Typically, when administering the agents or the composition described herein, materials to which the agents does not absorb are used.

In other embodiments, the engineered ligand described herein, or composition containing the engineered ligand is delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

In some embodiments, the engineered ligand described herein, or composition containing the engineered ligand is formulated in accordance with routine procedures as a pharmaceutical composition adapted for intravenous or subcutaneous administration to a subject, e.g., a human being. Typically, compositions for administration by injection are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

A composition for systemic administration may be a liquid, e.g., sterile saline, lactated Ringer's or Hank's solution. In addition, the composition can be in solid forms and re-dissolved or suspended immediately prior to use. Lyophilized forms are also contemplated.

The engineered ligand described herein, or composition containing the engineered ligand can be contained within a lipid particle or vesicle, such as a liposome or microcrystal, which is also suitable for parenteral administration. The particles can be of any suitable structure, such as unilamellar or plurilamellar, so long as compositions are contained therein. The agents described herein, or composition(s) containing such agents can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N,N-trimethyl-amoniummethyl-sulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757.

The engineered ligand described herein, or composition containing the engineered ligand of the present disclosure may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

Further, the engineered ligand described herein, or composition containing the engineered ligand can be provided as a pharmaceutical kit comprising (a) a container containing an agent of the disclosure in lyophilized form and (b) a second container containing a pharmaceutically acceptable diluent (e.g., sterile water) for injection. The pharmaceutically acceptable diluent can be used for reconstitution or dilution of the lyophilized agents of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration.

In some embodiments, an article of manufacture containing materials useful for the treatment of the diseases described above is included. In some embodiments, the article of manufacture comprises a container and a label. Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is an isolated polypeptide of the disclosure. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

The terms "treatment," "treat," and "treating" refer to reversing, alleviating, delaying the onset of, or inhibiting the progress of a disease described herein (e.g., a disease associated with abnormal GPCR activity). In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence. Prophylactic treatment refers to the treatment of a subject who is not and was not with a disease but is at risk of developing the disease or who was with a disease, is not with the disease, but is at risk of regression of the disease. In some embodiments, the subject is at a higher risk of developing the disease or at a higher risk of regression of the disease than an average healthy member of a population.

An "effective amount" of a composition described herein refers to an amount sufficient to elicit the desired biological response. An effective amount of an agent described herein, or a composition containing such agents may vary depending on such factors as the desired biological endpoint, the pharmacokinetics of the compound, the condition being treated, the mode of administration, and the age and health of the subject. In some embodiments, an effective amount is a therapeutically effective amount. In some embodiments, an effective amount is a prophylactic treatment. In some embodiments, an effective amount is the amount of an agent in a single dose. In some embodiments, an effective amount is the combined amounts of an agent described herein in multiple doses. When an effective amount of a composition is referred herein, it means the amount is prophylactically and/or therapeutically effective, depending on the subject and/or the disease to be treated. Determining the effective amount or dosage is within the abilities of one skilled in the art.

The terms "administer," "administering," or "administration" refers to implanting, absorbing, ingesting, injecting, inhaling, or otherwise introducing a compound described herein, or a composition thereof, in or on a subject. The agents described herein, or composition(s) containing such agents may be administered systemically (e.g., via intravenous injection) or locally (e.g., via local injection). In some embodiments, the composition of the vaccine composition described herein is administered orally, intravenously, topically, intranasally, or sublingually. Parenteral administration is also contemplated. The term "parenteral" as used herein includes subcutaneous, intracutaneous, intravenous, intramuscular, intraarticular, intraarterial, intrasynovial, intrasternal, intrathecal, intralesional, intradermally, and intracranial injection or infusion techniques. In some embodiments, the administering is done intramuscularly, intradermally, orally, intravenously, topically, intranasally, intravaginally, or sublingually.

Empirical considerations, such as the half-life, generally will contribute to the determination of the dosage. For example, therapeutic agents that are compatible with the human immune system, such as polypeptides comprising regions from humanized antibodies or fully human antibodies, may be used to prolong half-life of the polypeptide and to prevent the polypeptide being attacked by the host's immune system. Frequency of administration may be determined and adjusted over the course of therapy, and is generally, but not necessarily, based on treatment and/or suppression and/or amelioration and/or delay of a disease. Alternatively, sustained continuous release formulations of a polypeptide may be appropriate. Various formulations and devices for achieving sustained release are known in the art.

In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the polypeptide used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the polypeptide (such as the half-life of the polypeptide, and other considerations well known in the art).

For the purpose of the present disclosure, the appropriate dosage of will depend on the specific agent (or compositions thereof) employed, the formulation and route of administration, the type and severity of the disease, whether the polypeptide is administered for preventive or therapeutic purposes, previous therapy, the subject's clinical history and response to the antagonist, and the discretion of the attending physician. Typically the clinician will administer a polypeptide until a dosage is reached that achieves the desired result. Administration of one or more polypeptides can be continuous or intermittent, depending, for example, upon the recipient's physiological condition, whether the purpose of the administration is therapeutic or prophylactic, and other factors known to skilled practitioners. The administration of an agent may be essentially continuous over a preselected period of time or may be in a series of spaced dose, e.g., either before, during, or after developing a disease.

"A subject in need thereof", refers to an individual who has a disease, a symptom of the disease, or a predisposition toward the disease, with the purpose to cure, heal, alleviate, relieve, alter, remedy, ameliorate, improve, or affect the disease, the symptom of the disease, or the predisposition toward the disease.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In some embodiments, the non-human animal is a mammal (e.g., rodent (e.g., mouse or rat), primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). The non-human animal may be a male or female at any stage of development. The non-human animal may be a transgenic animal or genetically engineered animal.

In some embodiments, the subject is a companion animal (a pet). "A companion animal," as used herein, refers to pets and other domestic animals. Non-limiting examples of companion animals include dogs and cats; livestock such as horses, cattle, pigs, sheep, goats, and chickens; and other animals such as mice, rats, guinea pigs, and hamsters. In some embodiments, the subject is a research animal. Non-limiting examples of research animals include: rodents (e.g., rats, mice, guinea pigs, and hamsters), rabbits, or non-human primates.

Alleviating a disease includes delaying the development or progression of the disease, or reducing disease severity. Alleviating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease includes initial onset and/or recurrence.

Conventional methods, known to those of ordinary skill in the art of medicine, can be used to administer the isolated polypeptide or pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In some embodiments, the engineered ligand is administered subcutaneous, intramuscular, or intravenously. In addition, it can be administered to the subject via injectable depot routes of administration such as using 1-, 3-, or 6-month depot injectable or biodegradable materials and methods.

In some embodiments, the engineered ligand is used to treat a disease associated with abnormal GPCR activity. GPCRs are the target of 40% of approved drugs. In some embodiments, the disease is selected from: osteoporosis (targeting calcitonin receptor), hypoparathyroidism (targeting PTHR1), inflammatory diseases, pancreatic cancer, malignant melanoma (targeting CXCR2), HIV/AIDS (targeting CXCR4), cancer immunotherapy (targeting CXCR3), and type-2 diabetes (targeting glucagon like peptide 1 receptor).

EXAMPLES

Example 1. Engineered GPCR Ligands

The family of chemokine receptors and their ligands control trafficking of cells of hematopoietic origin. Each chemokine receptor can usually bind to multiple chemokines, and each individual chemokine can interact with more than one receptor. This creates a complex network of possible interactions, resulting in a combinatorial code that allows precise navigation of the responsive cells.

Chemokine receptors belong to the family of G-protein coupled receptors (GPCRs) and bind their respective ligands through interaction with an extended N-terminal segment of the chemokine. This segment penetrates into the central cavity formed by the arrangement of the 7 α-helical segments of the GPCR embedded in the lipid bilayer. Other GPCRs that bind proteinaceous or peptidic ligands in similar manner include the receptor for parathyroid hormone (PTH).

Described herein is an alternative means of activating the receptor for parathyroid hormone through improved targeting of otherwise sub-optimal ligands to the receptor. This approach can be applied with equal probability of success to other GPCRs that recognize proteinaceous ligands, such as the family of chemokine receptors. This is an attractive method of targeting chemokine receptors with less promiscuity than that displayed by their natural ligands, with considerable appeal for in vivo applications.

Figure 2A:
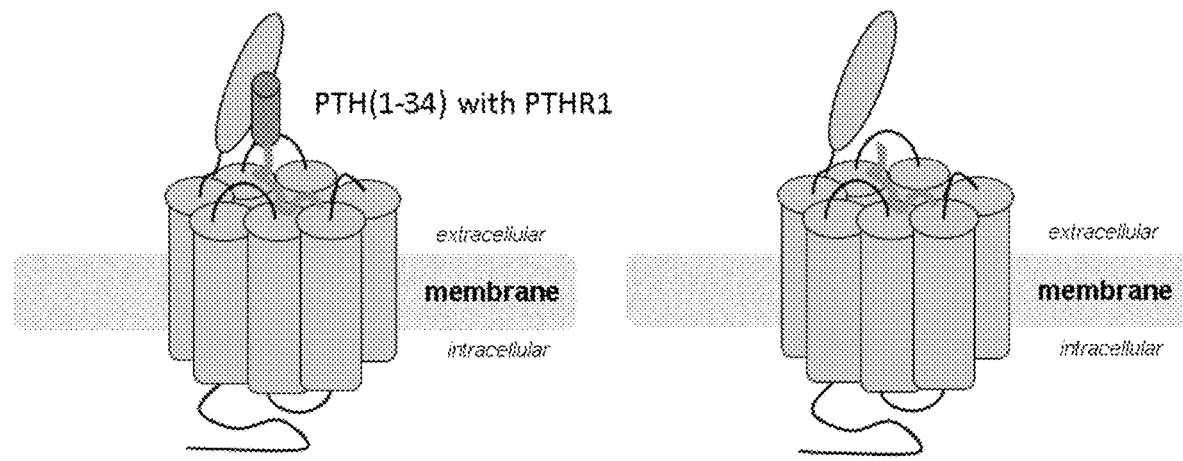
FIGS. 2A-2B: PTH(1-11) is a sub-optimal PTHR1 ligand.
Figure 2B:
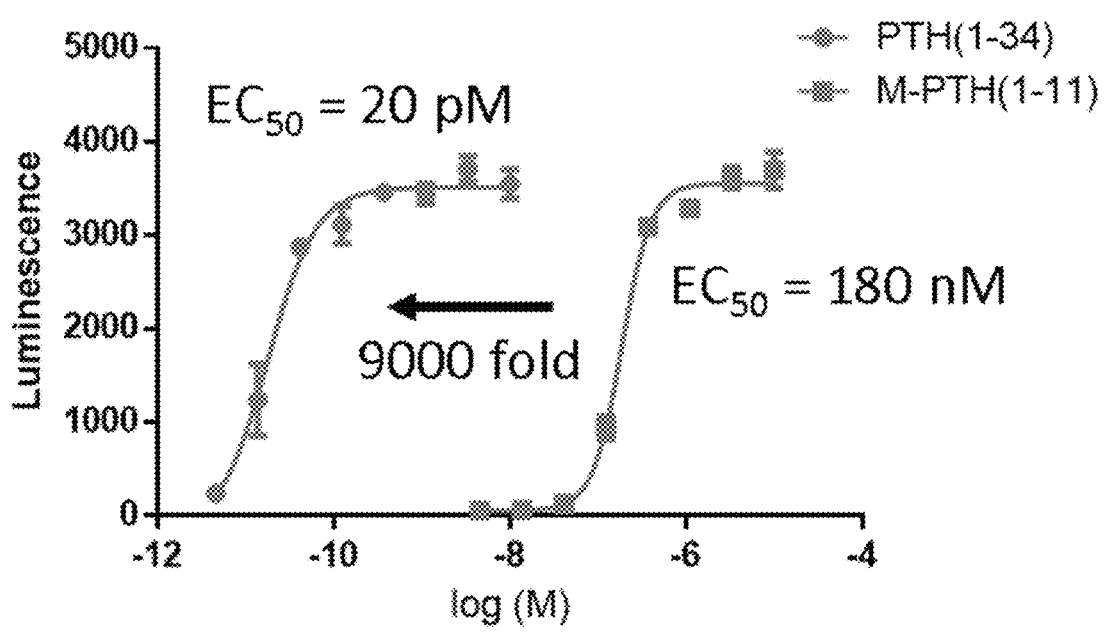

A bioactive fragment of parathyroid hormone (PTH) comprises the N-terminal 34 residues [PTH(1-34)], which potently activates the PTH receptor, PTHR1 (FIG. 1). PTH activates PTHR1 via its N-terminus, based on the observation that a modified analogue of PTH(1-11) retains activity, but with a potency for PTHR1 activation almost 4 orders of magnitude less than that of PTH(1-34), accounted for by its much weaker binding (FIG. 2). This observation also provides the evidence for a second site of interaction of PTH (1-34) with its receptor.

Figure 3:
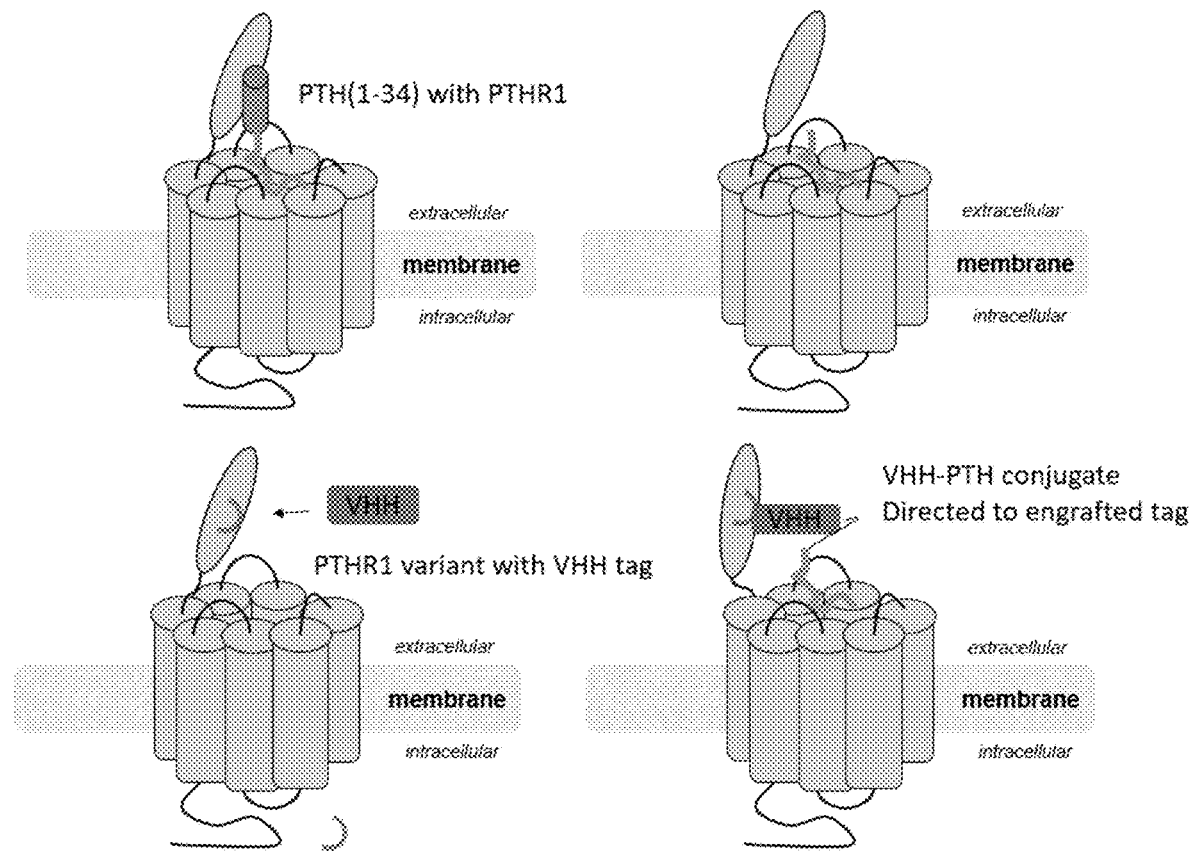
FIG. 3: Cartoon depiction of the modes of interaction of PTH peptide analogues and camelid single domain antibody (nanobody/VHH) conjugates with PTHR1. Tag recognized by VHH was engrafted into PTHR1 sequence.

As shown herein, the sub-optimal PTH(1-11) ligand was converted into a more potent one by provision of an second—artificial—site of interaction. To provide this additional site, a fusion of PTH(1-11) with a nanobody that recognizes the extracellular portion of PTHR1 was created. As a proof of concept, epitope tags recognized by nanobodies into a disordered portion of the PTHR1 extracellular domain were engineered. In similar fashion, a version of PTHR1 with GFP incorporated into the same disordered loop was created to enable the use of GFP-specific nanobodies (FIG. 3).

PTH requires a free N-terminus for interaction with PTHR1. To avoid disrupting the disposition of CDR1, CDR2 and CDR3 located near the nanobody's N-terminal region and required for binding, a fusion was formed by using the C-terminus of VHH05 and a C-terminally modified PTH(1-11) analogue (C-terminal to C-terminal non-natural fusion). This was accomplished by exploiting the chemoenzymatic installation of an azide to serve as a click handle at the C-terminus of each nanobody, and the installation of a dibenzylcyclooctyne (DBCO) substituent at the C-terminus of PTH derivatives using standard solid phase peptide synthesis (FIG. 4A). Not only did this approach overcome the limitations of genetic fusions, which do not allow C—C fusions, it also allowed the incorporation of non-natural amino acids such as aminoisobutyric acid (Aib). The use of Aib increases the PTHR1 activation potency of PTH(1-11) analogues by at least 10-fold. The nanobodies recognize the sequence QADQEAKELARQIS (SEQ ID NO: 53) (Ubc6e epitope), PDRKAAVSHWQQ (SEQ ID NO: 56) (Headlock) or GFP ("enhancer") (FIG. 4B).

Figure 5A:
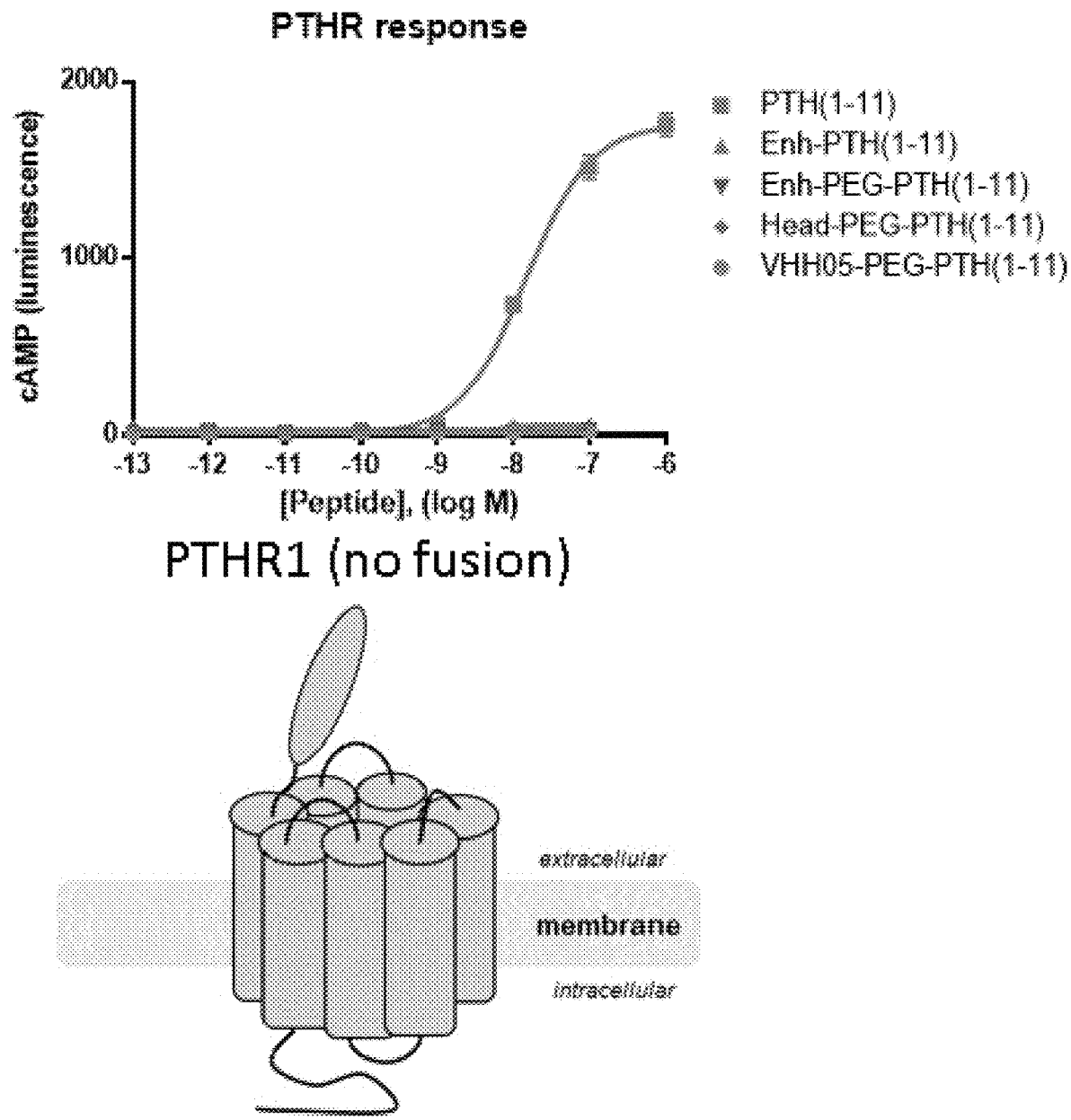
FIG. 5A-5B: VHH conjugation enhances the activity of PTH fragments. The biological activity of PTH fragments or PTH fragments conjugated to VHHs that bind to known targets was compared for two different PTHR1 constructs: wild type human PTHR1 (FIG. 5A) or human-PTHR1 fused to GFP (FIG. 5B).
Figure 5B:
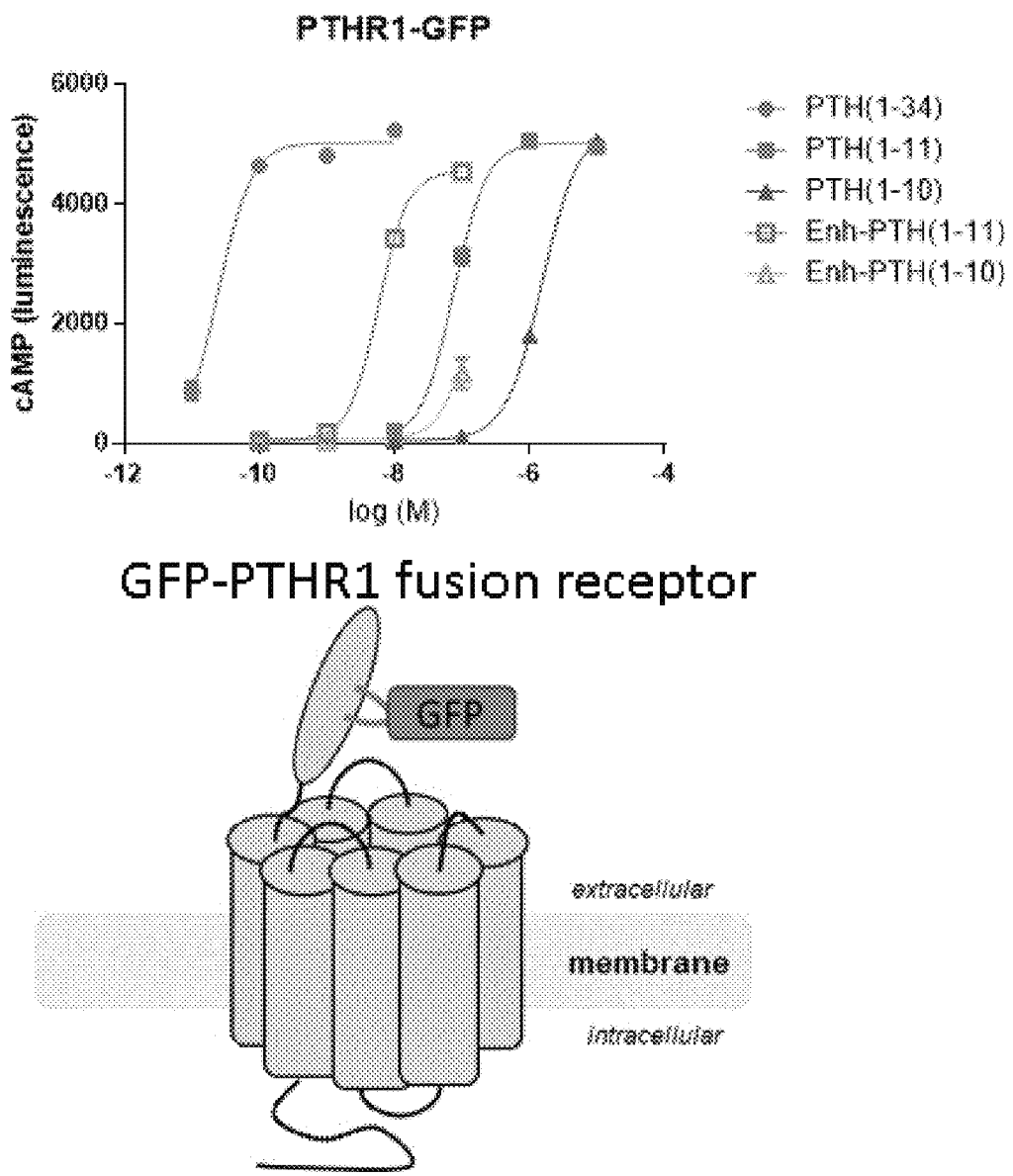

The GFP-PTHR1 fusion was stably expressed in cells that respond to receptor engagement by activation of a cAMP-sensitive version of luciferase. Exposure of these transfectants to PTH(1-11) yielded the expected dose-response curve with half maximal stimulation at ~200 nM. Nanobodies that recognize either one of the peptide epitope tags fused to PTH(1-11) failed to stimulate, whereas the anti-GFP nanobody fused to PTH(1-11) enhances its potency on GFP-PTHR1 by ~10-20 fold compared to free PTH(1-11) (FIGS. 5A and 5B).

Figure 6:
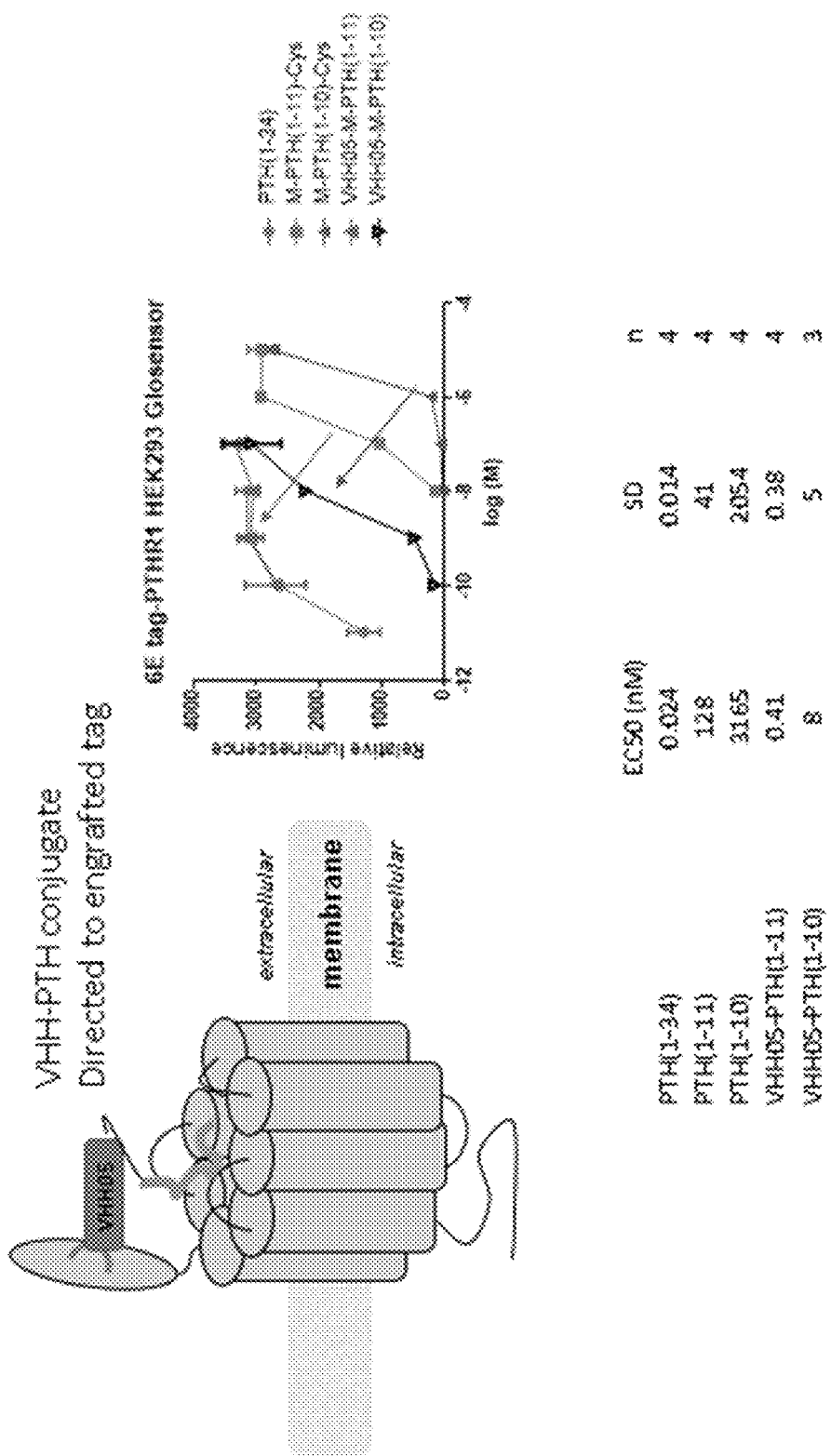
FIG. 6: Incorporation of a VHH-recognized tag (an epitope derived from Ubc6e, QADQEAKELARQIS, SEQ ID NO: 53) into PTHR1 enables the enhancement of ligand activity via conjugation to VHH05.

This result was improved by grafting the VHH05 epitope tag onto PTHR1 in a region that by crystallographic analysis was disordered. Administration of the VHH05-PTH(1-11) adduct was 500-fold more potent than PTH(1-11) and only 17-fold weaker than PTH(1-34) (FIG. 6). Even for a shorter version, PTH(1-10), a similarly striking increase in potency was observed when fused to VHH05 (FIG. 6).

Figure 11:
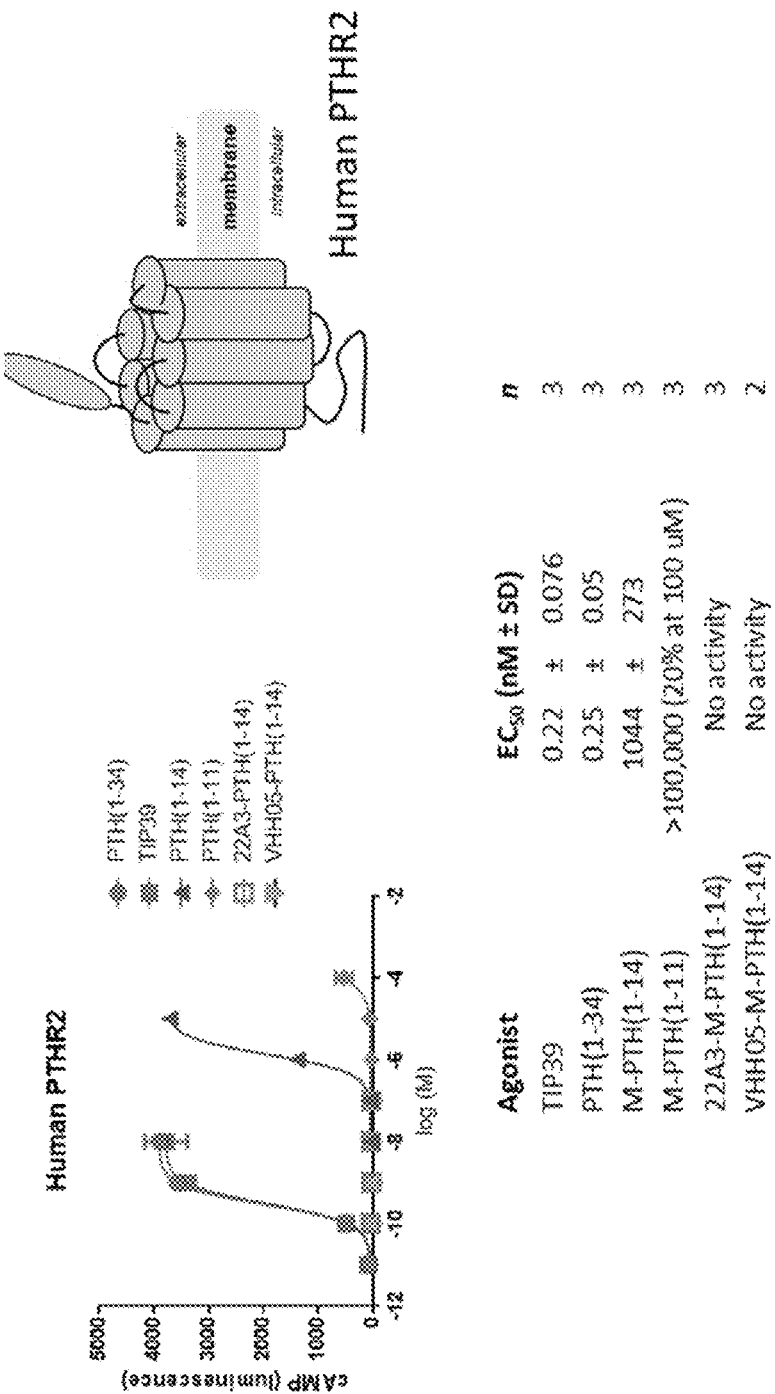
FIG. 11: Nanobody selectivity dictates ligand activity potentiation. PTH(1-14) conjugated to VHH05 or VHH22A3 did not activate human PTHR2, while a known PTHR2 ligand, TIP 39 (SLALADDAAFRERARLLAALERRHWLNSYMHKLLVLDAP, SEQ ID NO: 79), activated human PTHR2 ligand.

Whereas the results above were obtained using engineered GPCR variants that express an epitope/protein tag recognized by a nanobody, the same goal was also achieved by using a nanobody that recognizes the GPCR of interest itself. In pursuit of this, a nanobody described in a patent from Ablynx (US 2010/0062004 A1, nanobody 22A3) that recognizes human and rat PTHR1 was used. The PTH(1-11)-22A3 C-to-C conjugate was >60-fold more potent in activating unmodified human PTHR1 than PTH(1-11) itself (FIG. 9). The other PTH(1-11) fusions (enhancer, VHH05) failed to activate unmodified PTHR1 up to a concentration of 100 nM (highest concentration tested). This result indicates that epitope recognition by the nanobody-PTH(1-11) fusion is necessary for potent activation of the PTH receptor. The PTH(1-14)-22A3 conjugate or PTH(1-14)-VHH05 failed to activate cells that express human PTHR2 (a homolog of PTHR1), in line with the lack of binding of VHH22A3 or VHH005 to PTHR2 (FIG. 11).

These results demonstrate a novel nanobody-dependent way of targeting sub-optimal ligands to the corresponding receptor. Such sub-optimal ligands are devoid of significant activity when administered alone at concentrations similar to those used for the nanobody-PTH adducts. This concept can be applied to chemokine receptors as well, because nanobodies show greater discriminatory capacity for the different chemokine receptors than the ligands that bind to them. Like PTH, chemokines require a native N-terminus to bind to their receptors, and—as for PTH—truncated versions that include the N-terminus retain activity but at a much reduced level.

It was surprisingly found herein that, for ligands that are already very tight binders/potent "optimal", attaching them to targeting molecules does little to improve their potency. For example PTH(1-34) becomes less potent when attached to the directing nanobody (FIG. 10). For optimal ligands (such as PTH(1-34)) attachment to a nanobody does not provide specificity for the target. For example VHH05-PTH (1-34) activates wild type PTHR1 whereas VHH05-PTH(1-11) does not. The results showed that that PTH(1-34) is bioactive whether or not it is conjugated to VHH and selectivity is only achieved for short suboptimal peptides (like PTH(1-11)) but not for higher affinity peptides (like PTH(1-34)).

By fusing C-terminally truncated chemokine fragments to nanobodies that recognize a particular chemokine receptor, a given chemokine receptor can be uniquely addressed. For example, CXCR1 and CXCR2 both bind to IL8. Nanobodies have been identified that bind to CXCR2 but not CXCR1 (see: Bradley et al, Molecular Pharmacology February 2015, 87 (2) 251-262). By conjugating a weakly active N-terminal fragment of IL8 to such nanobodies selective agonists or antagonists of CXCR2 can be identified. This has implications for the treatment of inflammatory disorders (see Bradley et al Molecular Pharmacology February 2015, 87 (2) 251-262).

The approach described here for enhancing the activity of weak ligands for cell surface receptors, and the selectivity of said ligands for specific receptors, is not necessarily limited to proteinaceous ligands or GPCRs. For example, weakly active small molecule ligands of cell surface receptors can be conjugated and tethered site-specifically to nanobodies using a conceptually similar approach. Nanobodies to a variety of cell surface proteins (not just GPCRs) have been described and in these cases the method proposed here could be deployed as well.

Example 2—Improved GPCR Ligands from Nanobody Tethering

Antibodies conjugated to bioactive compounds such as cytotoxic drugs allow targeted delivery of therapeutics to cell types of choice, based on that antibody's specificity. A new type of conjugate was presented that consists of a nanobody and a peptidic ligand for a G protein-coupled receptors (GPCR), fused via their C-termini. The activation of parathyroid hormone receptor-1 (PTHR1) was addressed, the target of peptides used to treat osteoporosis, which has proven refractory to potent activation by small molecules. The signaling activity and specificity was improve of otherwise poorly active N-terminal peptide fragments of PTH by conjugating them to nanobodies that recognize the extracellular portion of PTHR1. These C-to-C conjugates show biological activity superior to that of the parent fragment peptide in vitro and in vivo, as shown in mice for a conjugate comprised of a PTH(1-14) analogue and the PTHR1-binding nanobody. The lead conjugate also possesses selectivity for PTHR1 superior to that of teriparatide. This design approach, dubbed "conjugation of ligands and antibodies for membrane proteins (CLAMPs)", can yield new ligands for cell surface receptors with properties superior to those previously provided by chemistry or nature.

Antibodies bind tightly and specifically to their targets, even in highly complex environments. This property of antibodies has been used to deliver bioactive compounds to sites of interest, both for diagnostic and therapeutic applications[1]. For example, conjugates between antibodies and cytotoxic drugs (antibody-drug conjugates or ADCs) can selectively kill cancer cells[2]. The success of ADCs often depends on the internalization of the conjugate through endocytosis, followed by release of the cytotoxic payload. Far fewer studies have made use of antibodies to deliver bioactive compounds with sites of action at the cell surface. The conjugation of a ligand for a surface receptor to an antibody that recognizes that same receptor should increase the effective concentration of the ligand and so increase its potency and specificity, provided appropriate spatial constraints are maintained. Ideally, this method could be used with an antibody that directly targets the receptor of interest to enable application to cells and organisms without the need for their genetic modification. The G protein-coupled receptor (GPCR) family of proteins is an attractive class of targets to pursue using this approach.

Figure 12:
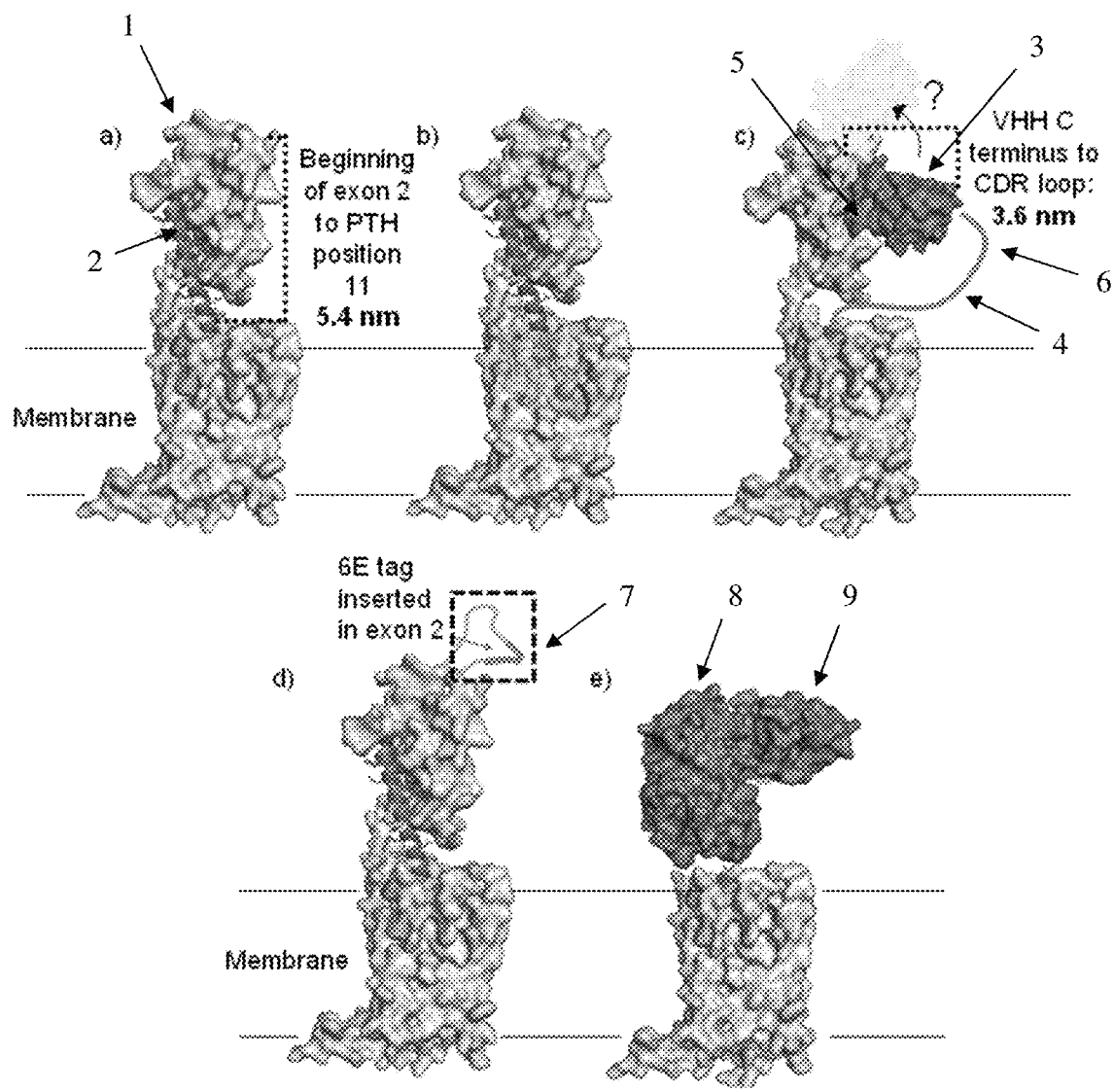
FIG. 12: Schematic of VHH-mediated delivery of PTHR ligands and the constructs used in this study. (Panel a) Crystal structure of human PTHR1 (1) bound to PTH(1-34) (2) protein data bank entry (PDB): 6FJ3. (Panel b) Structure as in panel a but with PTHR1 residues 231-296 and 349-353 shown in transparency to allow visualization of the N-terminal portion of PTH inserted into the transmembrane domain. (Panel c) Modeled complex of PTHR1 with VHH-PTH(1-11). The VHH structure (3) is based on $VHH_{GFP}$ from PDB: 3K1K and PTH(1-11) bound to receptor (4) is derived from PDB: 6FJ3. The complementarity determining loops (5) bind the target, and the C terminus (6), where the PTH fragment is attached. Neither the site of binding for $VHH_{PTHR}$, nor is its orientation relative to PTHR1 is known, as indicated by the ghost version of the VHH. (Panel d) Modeled structure of $PTHR1_{6E}$. The predicted location of the PTHR1 segment encoded by exon 2 is highlighted in the dashed box. The orientations of the inserted tags (6E-(7), YFP-(8)) relative to the remainder of the receptor are not known. (Panel e) Modeled structure of PTHR1$_{YFP\Delta ECD}$. Residues 31-179 from PTHR1 and residues 12-34 from PTH (PDB: 6FJ3) were removed to provide this structure. PTHR1$_{YFP\Delta ECD}$ is depicted in complex with VHH$_{GFP}$ ((9); PDB 3K1K).

Molecules that target GPCRs represent more than 25% of all approved drugs[3]. Antibodies and the variable fragments of camelid heavy chain-only antibodies (VHHs or nanobodies) have found increasing use for modulating GPCR signaling[4,5]. GPCRs and their ligands display a considerable degree of degeneracy. Several natural ligands bind to more than a single GPCR and many GPCRs can bind more than one ligand[6,7]. The parathyroid hormone receptors constitute one such example: a bioactive N-terminal fragment of parathyroid hormone (PTH, residues 1-34), used under the name teriparatide to treat osteoporosis, potently activates both type-1 and type-2 PTH-receptors (PTHR1/PTHR2)[8]. PTHR1/2 are part of the B-family of GPCRs which are naturally activated by large (>25 residue) peptides[9]. Despite intense pharmaceutical interest, no small molecule agonists of B-family GPCRs with potencies comparable to the natural ligands have been described. To address PTHR signaling and selectivity, conjugates of fragments of PTH and VHHs were prepared. VHHs are appealing building blocks for these conjugates, as they are the smallest antibody fragments that retain the ability to bind antigen and can be produced in high yield using bacterial expression[10]. The site of antigen recognition on VHHs is near the N-terminus[11,12] and the interaction of PTHR1 and PTHR2 with their ligands requires a free N-terminus on the latter[8,13,14]. Using a chemo-enzymatic approach, C-to-C-terminal fusions of PTH fragments and VHHs[15] was made. These chimeric molecules, dubbed "conjugates of ligands and antibodies for membrane proteins" or CLAMPs, target either wild-type or engineered receptor variants (FIG. 12). The optimized CLAMPs display biological activities in vitro and in vivo that are vastly superior to those of the PTH fragments from which they were derived. When otherwise weakly active PTH fragments are incorporated into these conjugates, they can be made exquisitely selective for activation of only those receptors engaged by the VHH. This stands in marked contrast to the lack of selectivity shown by PTH(1-34)[8]. These findings suggest that CLAMPs should be broadly applicable for the design of ligands with unique and useful properties.

Methods

General. HEK293 cell lines were cultured in DMEM medium supplemented with 10% (v/v) fetal bovine serum and penicillin/streptomycin. Cell lines were routinely tested *mycoplasma* infection. LC/MS was performed on a Waters Xevo Q-Tof system equipped with HPLC-C8 columns. Mass spectra were obtained using Q-Tof mass spectrometry with a positive ionization mode. Masses for VHHs and conjugates were calculated via analysis of multiply charged ions using the MaxEnt feature on MassLynx software. Protein and peptide concentrations were calculated using absorption at 280 nm for VHHs and peptides with tryptophan (Trp) residues. For peptides without Trp, the amount of peptide was quantified gravimetrically assuming that the weighed mass consisted of 50% peptide (w/w). Antibody 12CA5 was purchased from Sigma Aldrich. Polyclonal mouse IgG was purchased from Southern Biotech. Transfections of HEK293 were performed using Lipofectamine2000 using manufacturer instructions.

Plasmids and DNA. HEK293-derived cell lines stably expressing human PTHR1 (GP2.3), rat PTHR1 (GR35), PTHR1$_{GFP}$ (GPG10), and PTHR1$_{YFP\Delta ECD}$ (GD5) along with a cAMP-responsive luciferase variant have been previously reported[19,21,27]. A HEK293 cell line stably expressing β-Arrestin2-YFP (GBR24) was constructed similarly[51].

PTHR1$_{6E}$ was produced using the Q5 Site-directed mutagenesis kit (NEB) and used to prepare a stably transfected HEK293-derived cell line. Annotated sequence data for all PTHR1 constructs are SEQ ID NO: 76, 78, and 82-84. Aligned sequences of VHHs used in this study are shown in SEQ ID NO: 71, 73, 74, and 80. Materials are available upon request.

Figure 17A:
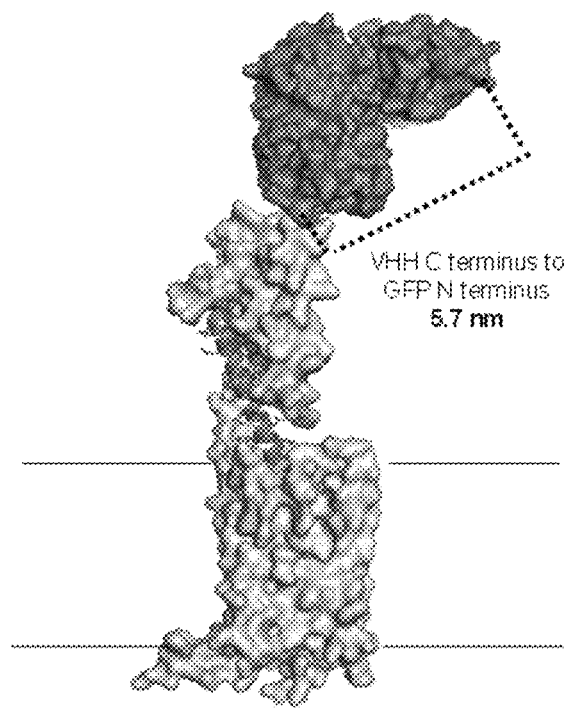
Figure 17B:
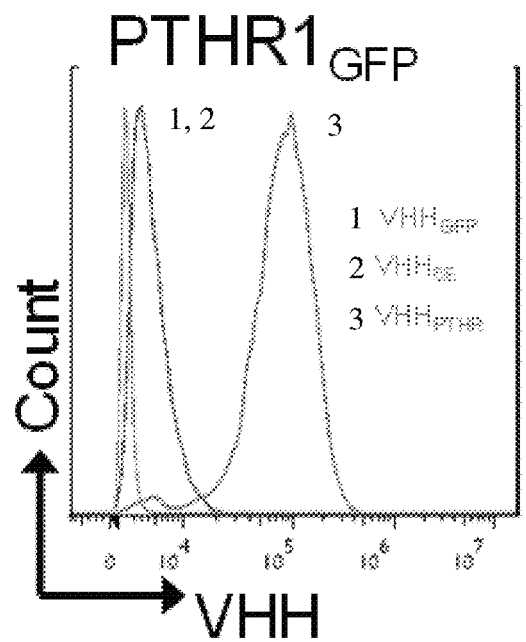

Peptide synthesis. Peptides were prepared using conventional solid-phase synthesis methods with Fmoc-protection of backbone amines. Synthesis was performed on Rink-amide linker resin to yield C-terminal amides. Backbone deprotection was performed via treatment with piperidine in dimethylformamide (DMF, 20% vol/vol) for 15 minutes at room temperature. Coupling was performed using Fmoc-protected amino acids (4 equivalents), N,N,N',N'-Tetramethyl-O-(1H-benzotriazol-1-yl)uronium hexafluorophosphate (HBTU, 4 equivalents), and diisopropylethylamine (DIPEA, 8 equivalents) in DMF for 45 minutes at room temperature. Fmoc-Lys(biotin)-OH and Fmoc-Lys(azide)-OH were from used from commercial sources without alteration the synthetic methods described above. Following completion of synthesis, the resin was dried and deprotection was carried out using a solution of 92.5% trifluoroacetic acid, 5% $H_2O$, and 2.5% TIPS. Peptides were precipitated into diethyl ether, pelleted by centrifugation, dried under a stream of air, purified using reversed-phase C18 HPLC using a water-acetonitrile gradient, and lyophilized. The identity and approximate purity of peptides was confirmed by LC/MS (FIGS. 17A to 17C). Purified products were dissolved in water (10 mM stock concentration) and stored at −20° C.

Purified peptides with C-terminal cysteines were subjected to a reaction with a 2-fold molar excess of either DBCO-maleimide (Click Chemistry Tools) or DBCO-PEG$_3$-maleimide (ConjuProbe) (FIGS. 26A to 26F) in solvent with 50% (v/v) dimethylsulfoxide (DMSO) and 50 mM pH 7.4 phosphate buffer and purified by reversed-phase C18 HPLC. The identity of peptides was confirmed by LC/MS (FIG. 18). Purified products were dissolved in DMSO (1 mM stock concentration) and stored at −20° C.

Protein expression and purification. The production and purification of VHH$_{GFP}$(named VHH-enhancer) and VHH6E (named VHH05) has been described previously[20, 22]. The sequence for VHH$_{PTHR}$ was acquired from the literature (named 22A3)[23]. Although several VHHs that bound PTHR1 were reported, 22A3 was selected as it was reported to have the highest affinity[23]. Briefly, VHHs were expressed using the pHEN6 vector. Plasmids coding for PelB-VHH-LPETGG-His$_6$ were transformed into WK6 *E. coli* using heat shock. Transfected WK6 *E. coli* were grown in Luria Bertani broth under ampicillin selection at 37° C. until an optical density at 600 nm between 0.6 and 0.8 was reached. Protein expression was induced by the addition of 1 mM IPTG and cells were grown at 30° C. overnight. The bacteria were pelleted by centrifugation and resuspended in TES buffer (50 mM Tris, 650 μM EDTA, 2 M sucrose, 15 mL buffer per liter of culture) to prepare for osmotic shock. After incubating for 2 hours at 4° C., 75 ml distilled $H_2O$ was added, and the bacterial suspension was incubated overnight at 4° C. The bacteria were again pelleted and VHHs were purified from the supernatant by Ni-NTA bead batch purification, followed by buffer exchange. Sortase-A pentamutant was expressed and purified as previously described[3].

Flow cytometry. Suspensions of cells in PBS were stained for 1 hour on ice in the presence of indicated concentrations of VHH probes functionalized with Alexafluor647. Cells were pelleted by centrifugation and washed with PBS prior to analysis by flow cytometry (BD Accuri C6). Gating was performed on forward scatter/side scatter profiles to analyze intact cells. Data was analyzed using FlowJo version 7.6. The median fluorescent intensity (MFI) of stained cells was used to generate VHH binding dose response curves (FIG. 20). For curves that did not reach plateau at the highest concentrations tested, curves were constrained by setting the maximal plateau value equal to that seen when staining that cell line with other VHHs that did achieve a plateau.

Sortase-mediated labeling (sortagging). VHHs were labeled using sortase A pentamutant as described[25]. Briefly, VHH (20-100 μM) with a C-terminal sortase-recognition motif and His-tag were incubated with GGG-peptide (500 μM) and sortase A pentamutant (10 M) in Tris-buffered saline (TBS) containing 10 mM $CaCl_2$) overnight at 14° C. Functionalized VHHs were purified from unreacted VHH and sortase by exposure to nickel-NTA sepharose beads and removal of GGG-peptide by buffer exchange using a 10 kDa molecular weight cutoff spin filter or a PD10 disposable size exclusion column. Purified VHH conjugates were concentrated using 10 kDa spin filter. VHH-PTH(1-14) and VHH-G$_3$-PTH(1-14) conjugates were prone to precipitation following concentration.

VHH-peptide conjugation reactions. VHH-biotin-azide conjugates (FIGS. 13A to 13C) were mixed with PTH-DBCO (3-fold molar excess) in TBS with 10% (v/v) glycerol. The reaction was shaken at 22° C. until unreacted VHH-biotin-azide had been completely consumed. The product conjugate was purified from free PTH-DBCO using a PD10 size exclusion column. Product identity was confirmed by LC/MS (FIG. 19).

Microscopy. Monolayers of HEK293 cells grown on glass cover slips at approximately 80% confluency expressing either hPTHR1 or PTHR$_{6E}$ were washed with Hanks balanced salt solution supplemented with 10 mM HEPES pH 7.4 and 0.1% (w/v) bovine serum albumin (HB). The cells were then stained with M-PTH(1-20)-fluorescein and VHH-tetramethylrhoadmine in HB at 4° C. for 30 m. After staining, cells were washed with HB three times, and fixed with 4% formalin either immediately after rinsing or following a 15 m incubation at room temperature in DMEM+ 10% FBS. Cells were then rinsed and mounted with Vectorshield containing DAPI (to visualize nuclei) on glass slides for imaging. Images were acquired using a Nikon Eclipse Ni system with a 40× PLAN FLUOR 0.75NA DIC M/N2 objective.

Measurement of cAMP response. These assays were performed as previously described[27]. Briefly, HEK-293-derived cell lines that stably express the Glosensor cAMP reporter (Promega Corp.)[30] and PTHR1, a PTHR1 variant, or PTHR2 were seeded into white sided 96 well plates (50,000 cells/well) and grown to confluency. Confluent monolayers of cells were pre-incubated with CO2 independent medium containing D-luciferin (0.5 mM) at 37° C. until a stable baseline level of luminescence was established (20 min). Varying concentrations of ligands were then added, and the time course of luminescence response was recorded using BioTek plate reader. The maximal luminescence response (observed 12-16 min after ligand addition) was used to construct dose-response data sets (Table 4, FIGS. 22A to 22E).

For the measurement of cAMP signaling duration experiments (FIGS. 24A to 24H) were performed as previously described[28]. Cells were treated with ligands at the indicated concentrations for 12 minutes (ligand-on phase). After this period, the medium in each well was removed and the cells were rinsed twice with C02-independent medium to remove unbound ligand. After the addition of D-luciferin-containing fresh medium to each well, the luminescence was recorded for an additional 30-40 minutes using a PerkinElmer Envision plate reader (ligand-off phase).

Measurement of cytoplasmic calcium mobilization. The mobilization of $Ca^{2+}$ levels was assessed in the HEK293 cell line stably transfected with human PTHR1. Intracellular Ca2+ levels were assessed using a cell-permeant $Ca^{2+}$ sensor, Fura2-AM (Invitrogen). Cells in a black 96-well plate were loaded with Fura2-AM in the presence of Pluronic F-127 for 45 min and then rinsed with Hanks buffered saline solution (HBSS). Following an additional 30-minute incubation in HBSS, the plate was analyzed using a PerkinElmer Life Sciences Envision plate reader to monitor fluorescence emission at a wavelength of 510 nm, upon excitation at wavelengths of 340 and 380 nm. The data were recorded at 2-second intervals prior to and after ligand addition. The data were calculated as the ratio of the fluorescence signal obtained with excitation at 340 nm to that obtained with excitation at 380 nm.

Measurement of internalization using GFP fluorescence. Receptor internalization was assessed in the HEK293 cell line stably transfected with human PTHR1-pHluorin2-GFP (GPG10)[19]. Confluent monolayers of cells in black walled 96 well plates were incubated in HBSS with bovine serum albumin (0.1% w/v) and HEPES buffer (pH 7.4, 10 mM). Peptides or peptide-VHH conjugates were added and wells were analyzed by recording fluorescence readouts with excitation at 485 nm or 405 nm and emission at 535 nm. Data were analyzed as a ratio of fluorescence intensity following excitation at 485/405 nm over the course of 90 minutes.

Animal experiments and measurement of in vivo response. Mice (CD1 female, age 11 weeks) were treated in accordance with the ethical guidelines adopted by Massachusetts General Hospital. Calcemic response assays were conducted using cohort sizes comparable to past work[27], which provided data adequate for identifying differences in the time course and magnitude of PTH-induced calcemic responses. Peptides and conjugates were administered at doses that allowed for differentiation between compounds with differing levels of in vivo activity[27]. Statistical analyses were performed assuming Gaussian distribution of data. Mice (n=4 per compound) were injected subcutaneously with vehicle (10 mM citric acid/150 mM NaCl/0.05% Tween-80, pH 5.0) or vehicle containing PTH or conjugate at a dose of 35 nmol/kg body weight. Prior to injection, mice were grouped according to basal blood calcium concentrations to ensure each group possessed similar average (mean) blood ionized calcium levels at t=0. Blood was withdrawn just before injection (t=0) or at times thereafter. Tail vein blood was collected and immediately analyzed. Blood $Ca^{2+}$ concentration was measured with a Siemens RapidLab 348 Ca2+/pH analyzer.

Data calculations. Data were processed using Microsoft Excel and GraphPad Prism 6. Data from cAMP dose-response assays were analyzed using a sigmoidal dose-response model with variable slope. Data sets were statistically compared by using Student's t test (two-tailed) assuming unequal variances for the two sets.

Results

Receptor constructs and conjugates used for targeting. PTH(1-34) interacts with PTHR1 via a two-site mechanism of interaction (FIG. 12)[8, 16]. The association between the extracellular domain of PTHR1 and residues 12-34 of PTH provides the bulk of the binding energy and specificity for this interaction. The association between the transmembrane domain of PTHR1 and residues 1-14 of PTH induces a conformational change in the receptor, which initiates intracellular signaling cascades. This mode of interaction, supported by a large amount of structure-activity relationship data, has been confirmed recently by high resolution crystallographic and cryo-electron microscopy analysis of PTHR1-ligand interactions (FIG. 12)[13, 14].

To mimic receptor association exhibited by PTH(1-34), either wild-type PTHR1 or PTHR1 variants was used, modified to carry an epitope in the extracellular domain recognized by a VHH of choice. While there is no structural information for any VHH bound to PTHR1, a mode of interaction was envisioned between the receptor and VHH-PTH conjugates like that depicted in FIG. 12—Panel c. The portion of PTHR1 encoded by exon 2 is not resolved in structural studies (FIG. 12—Panel d)[13, 14, 17], is not important for ligand binding[18], and in past work has been targeted as a site for receptor modification[18, 19]. A construct was generated that encodes a PTHR1 variant in which a 14-residue fragment from exon 2 was replaced with a 14-mer epitope tag from the intracellular protein UBC6e (PTHR1$_{6E}$, FIG. 12—Panel d)[20]. A receptor construct in which a pH-sensitive green fluorescent protein variant (GFP) was inserted into the portion of the receptor encoded by exon 2 (PTHR1$_{GFP}$ in FIGS. 17A to 17C)[19]. Another version of PTHR1 in which yellow fluorescent protein (YFP) replaces the entire extracellular domain (PTHR1$_{YFP\Delta ECD}$, FIG. 12—Panel e)[21], was also used.

Figure 13C:
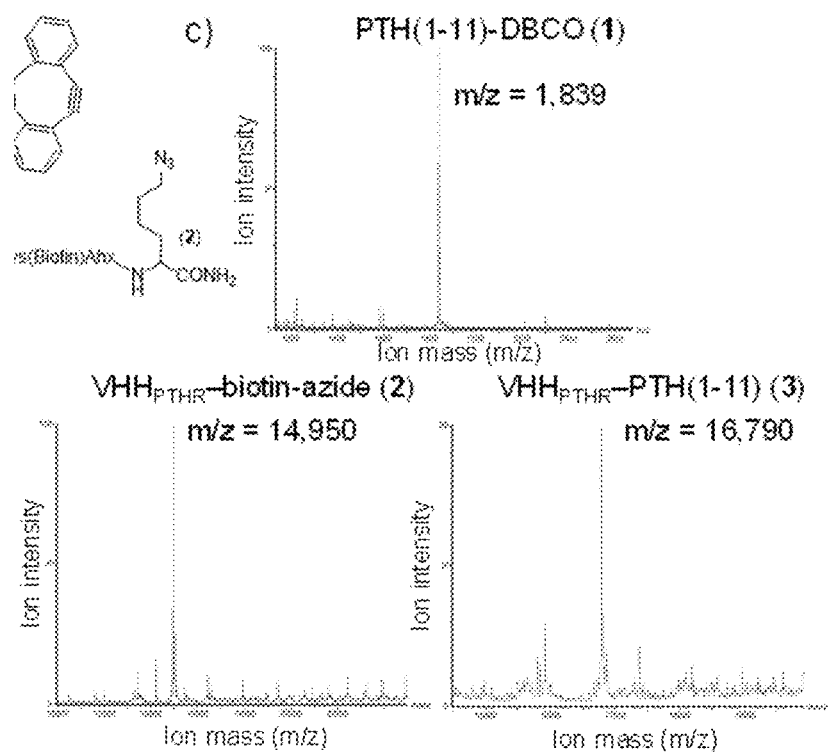

To target these receptors, conjugates comprised of N-terminal fragments of PTH and VHHs (FIG. 12) were constructed. VHHs that recognize green or yellow fluorescent proteins (VHH$_G$FP)[22], a 14-mer peptide fragment from the intracellular protein UBC6e (VHH$_{6E}$)[20], or PTHR1 itself (VHH$_{PTHR}$)[23]. C-terminally His-tagged VHHs was expressed in bacteria in a form amenable to subsequent site-specific functionalization at the C-terminus, using sortase A-mediated labeling (sortagging)[24, 25]. VHHs were attached to either a triglycine-modified fluorophore for cytofluorimetry or a peptide with azide and biotin moieties for biorthogonal chemistry and conjugate tracking, respectively (FIGS. 13A to 13C).

Figure 14A:
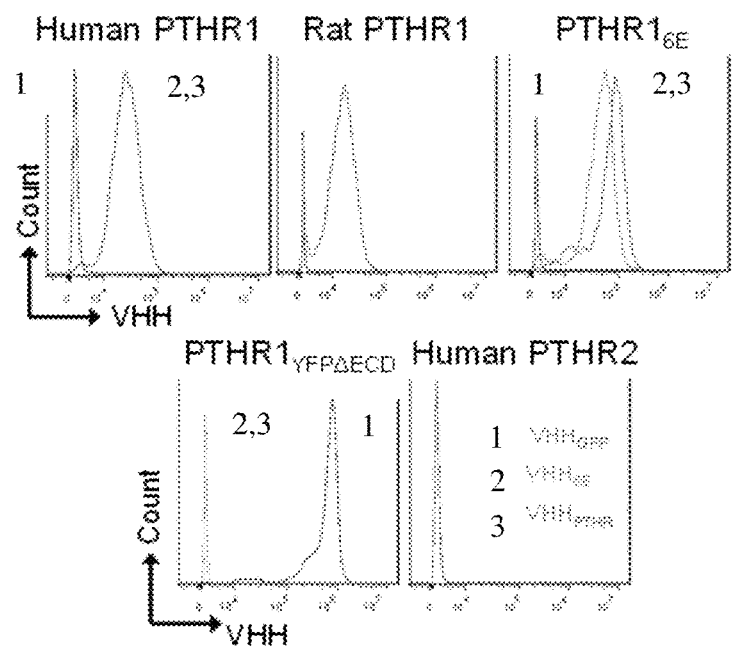
FIGS. 14A-14B: Binding of VHHs to HEK293 cell lines stably transfected with PTHRs.

It was determined whether VHHs bound to their intended targets on live cells by flow cytometry (FIG. 14A). HEK293 cell lines stably transfected were stained with the PTHR1 variants described above, rat PTHR1 (rPTHR1)[27], or PTHR2. rPTHR1 has been studied extensively and is identical to murine PTHR1 (mPTHR1) in the extracellular domain outside of exon 2. VHHs that bind to rPTHR1 should also bind to mPTHR1 and be useful for studies in mice. Each of the VHHs stained the expected cell lines, with the exception of the VHH$_{GFP}$-PTHR1$_{GFP}$ pair, as discussed in FIGS. 17A to 17C. VHH$_{PTHR}$ bound all constructs that retained the PTHR1 ECD, including rat PTHR1, but not PTHR1$_{YFP\Delta ECD}$. This places the binding site primarily in the PTHR1 extracellular domain (ECD). Only VHH$_{GFP}$ stained cells that express PTHR1$_{YFP\Delta ECD}$, consistent with its ability to bind YFP[22]. None of the VHHs tested stained the cell line that expresses PTHR2[28]. To estimate the affinity of the selected VHH for their targets flow cytometry was used to quantify binding. The staining of PTHR1YFP-del-NT by VHH$_{GFP}$ and PTHR1$_{6E}$ by VHH$_{6E}$ exhibited half-maximal staining at less than 10 nM, whereas the staining of cells expressing each of the PTHR1 receptor constructs that retained the ECD reached half-maximal staining at 100-200 nM (FIG. 20). The precise half-maximal staining concentrations for VHH$_{P_tH_R}$ are unknown because the intensity of staining (MFI) did not plateau at the highest concentrations tested and this value was estimated from other experiments.

Figure 14B:
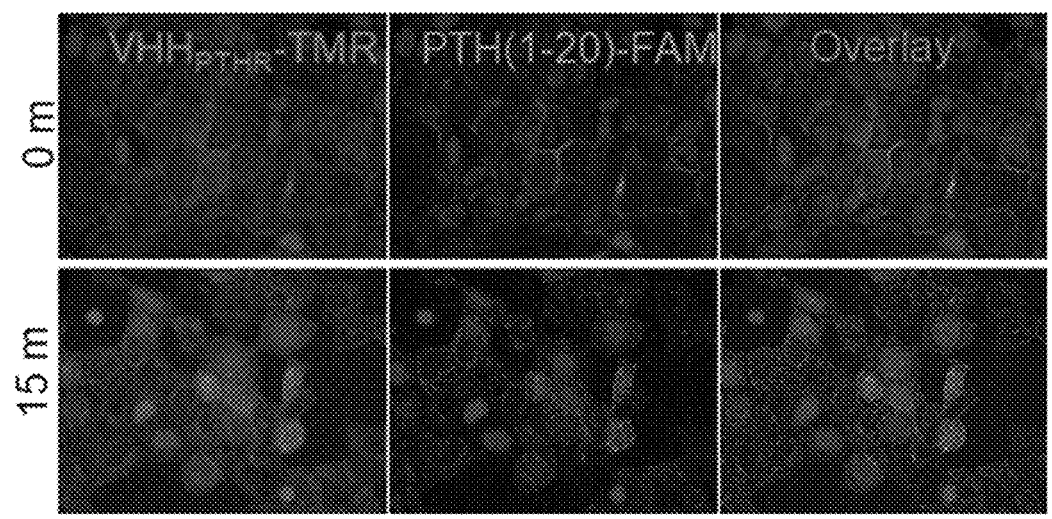
Figure 21A:
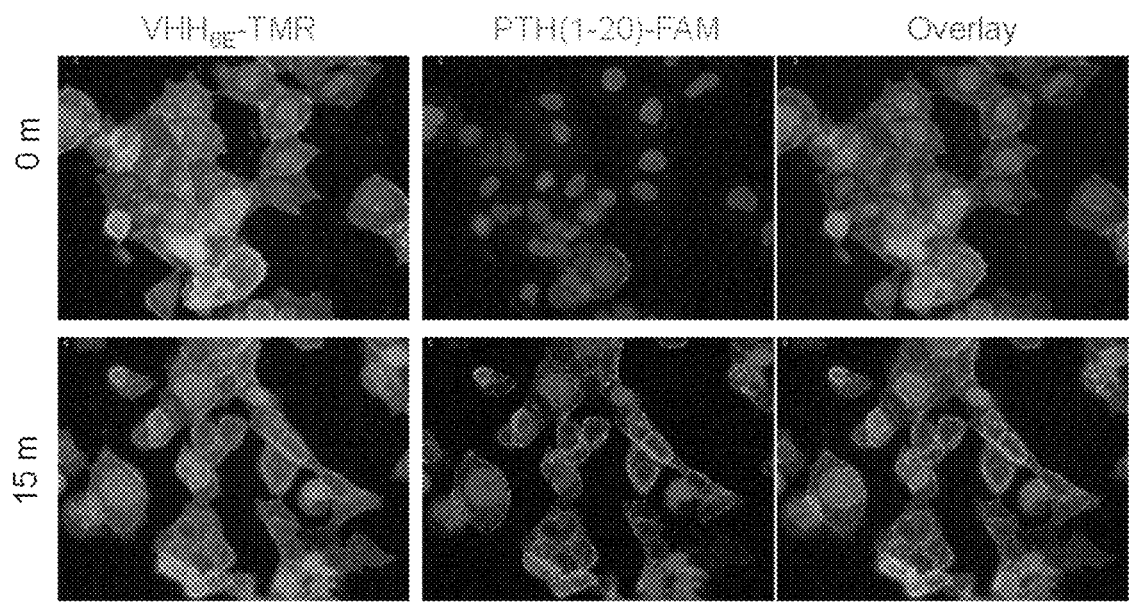
FIGS. 21A-21B: Assessment of VHH$_{6E}$ and PTH(1-20) binding to PTHR1$_{6E}$ using microscopy.
Figure 21B:
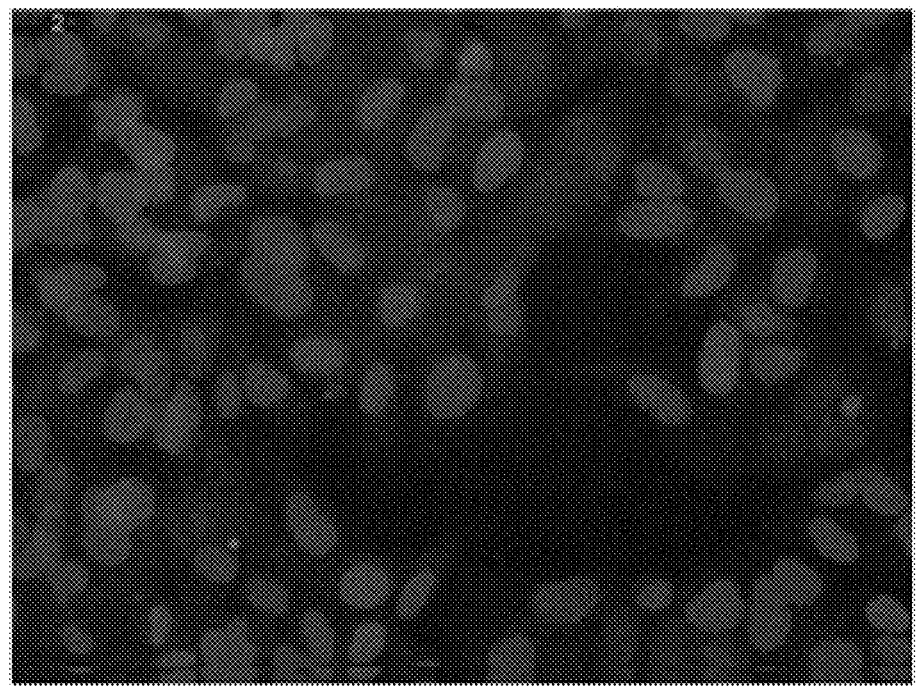
Figure 22A:
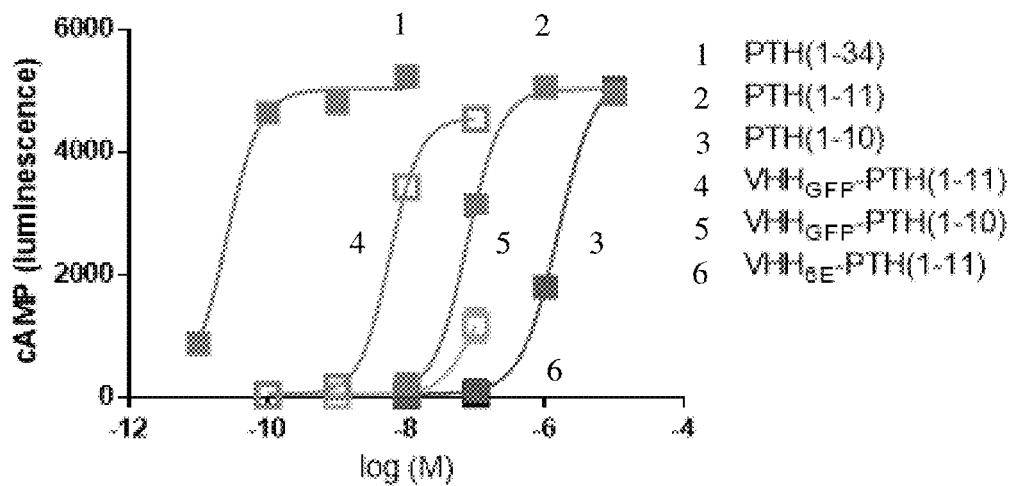
FIGS. 22A-22E: Representative dose-response curves for cAMP induction in HEK293 cell lines. Varying concentrations of ligands were added to clonal HEK293-derived cell lines stably expressing the indicated receptor and the time course of luminescence response was recorded using BioTek plate reader. The maximal luminescence response (observed 12-16 min after ligand addition) was used to construct dose-response data sets. Data points represent mean±SD and connecting lines result from the fit of a four-parameter sigmoidal dose-response model. Cell lines stably express (FIG. 22A) PTHR1$_{GFP}$, (FIG. 22B) PTHR1$_{6E}$, (FIG. 22C) PTHR1$_{YFP\Delta ECD}$, or (FIGS. 22D and 22E) human PTHR1.
Figure 22B:
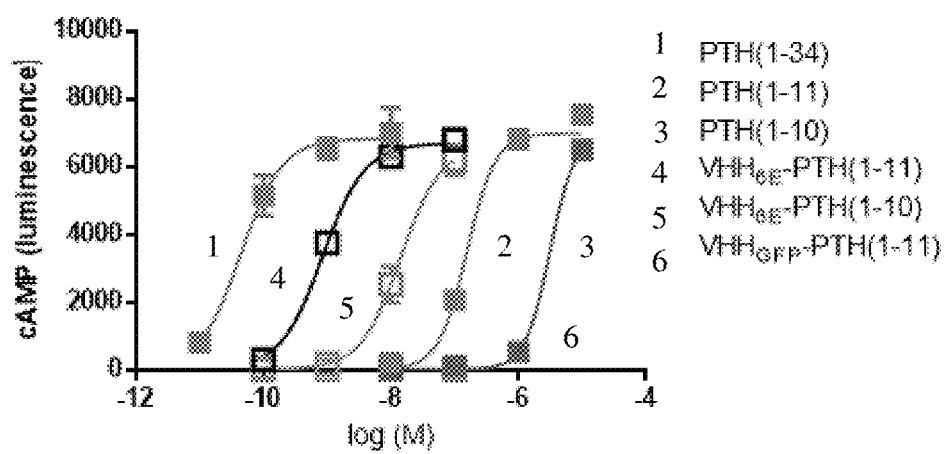
Figure 22C:
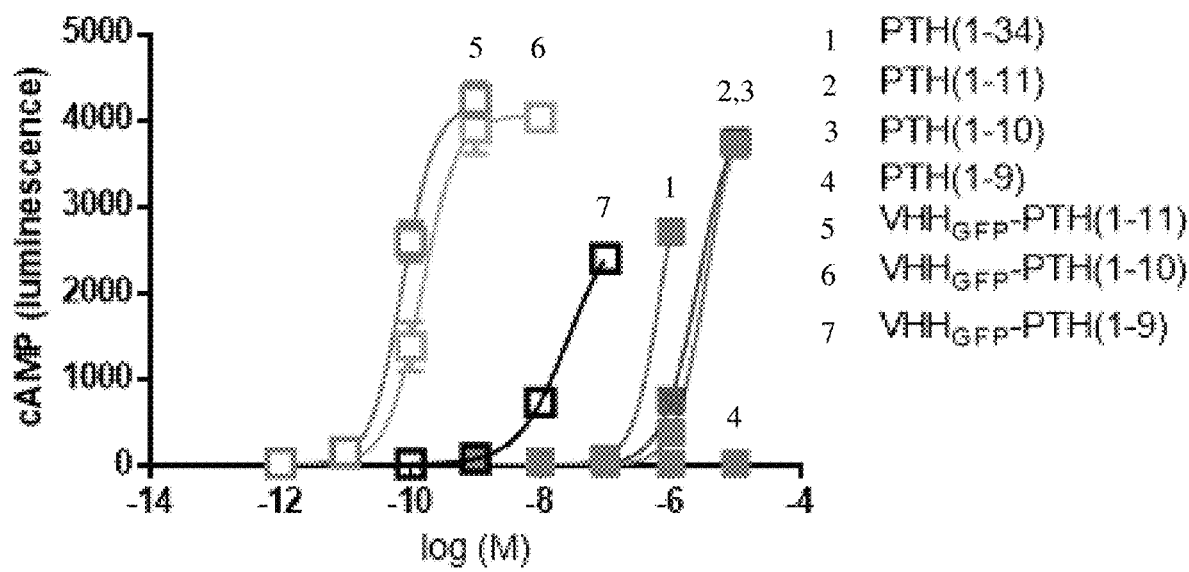
Figure 22D:
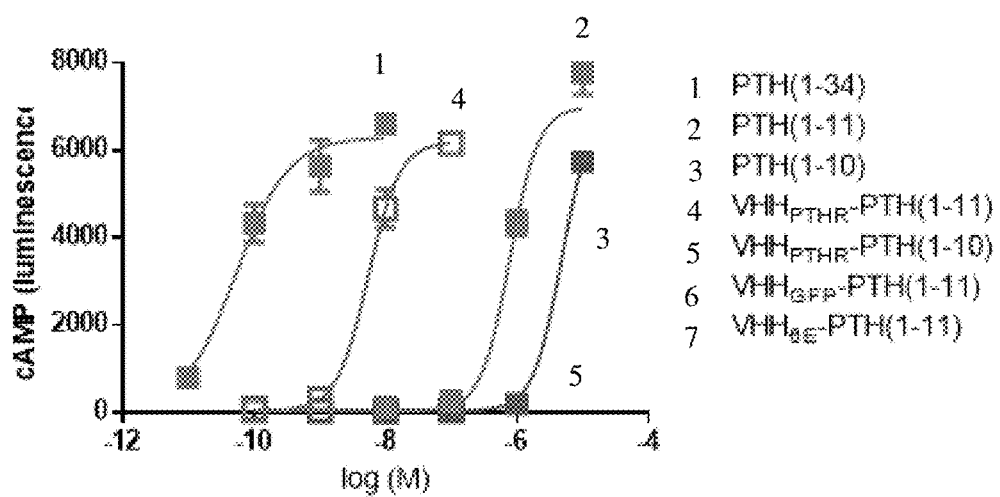
Figure 22E:
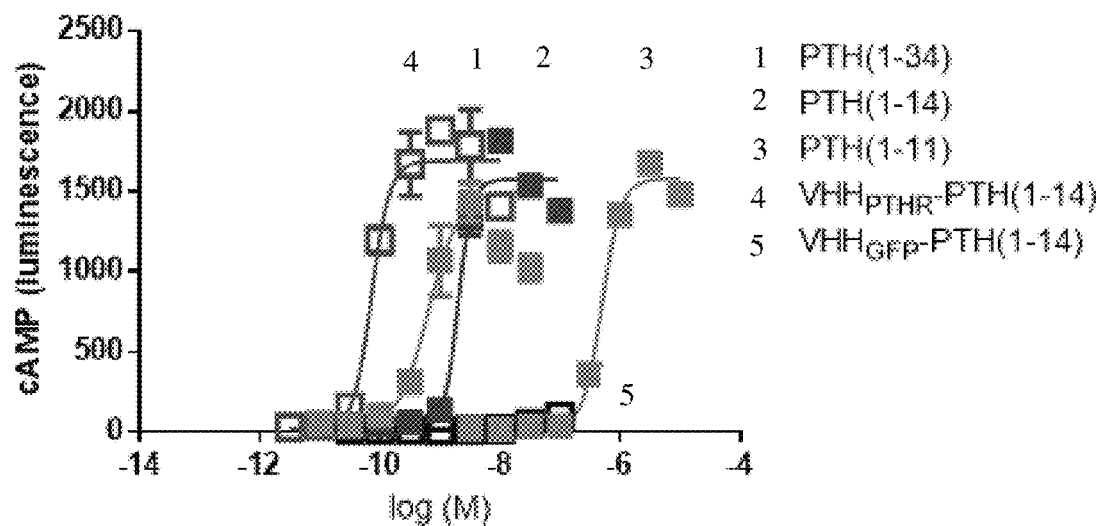

Microscopy was used to complement these flow cytometry experiments and visualized trafficking of either PTHR1 or PTHR1$_{6E}$ following engagement by PTH(1-20) functionalized with fluorescein and either VHH$_{PTHR}$ or VHH$_{6E}$ tagged with tetramethylrhodamine (FIG. 14B FIGS. 21A to 21B). Imaging of cells fixed immediately after staining on ice shows colocalization of VHH and PTH at the cell surface. Following a 15-minute incubation at room temperature, punctate and colocalized fluorescent signals were observed, corresponding to endocytosed receptor-PTH-VHH complexes[29]. Cells not transfected with PTHR1 showed weak staining (FIGS. 21A to 21B). These data indicate that the VHHs used and PTH(1-20) can simultaneously engage the receptor.

Figure 23A:
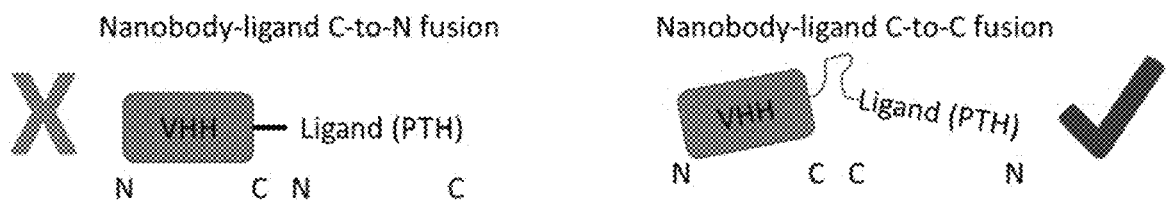
FIGS. 23A-23C: Modification of the N-terminus of PTH degrades activity.
Figure 23B:
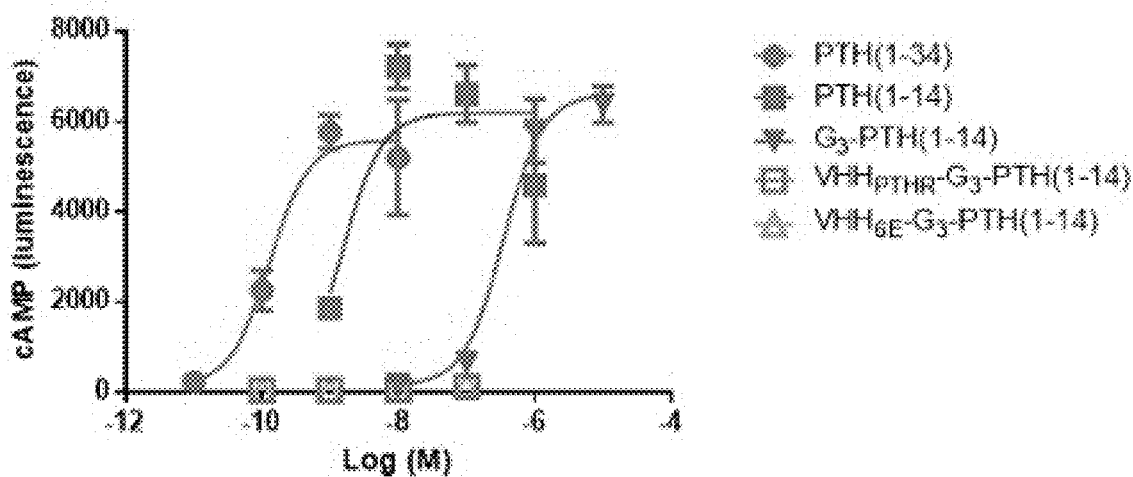
Figures 23C, 24A:
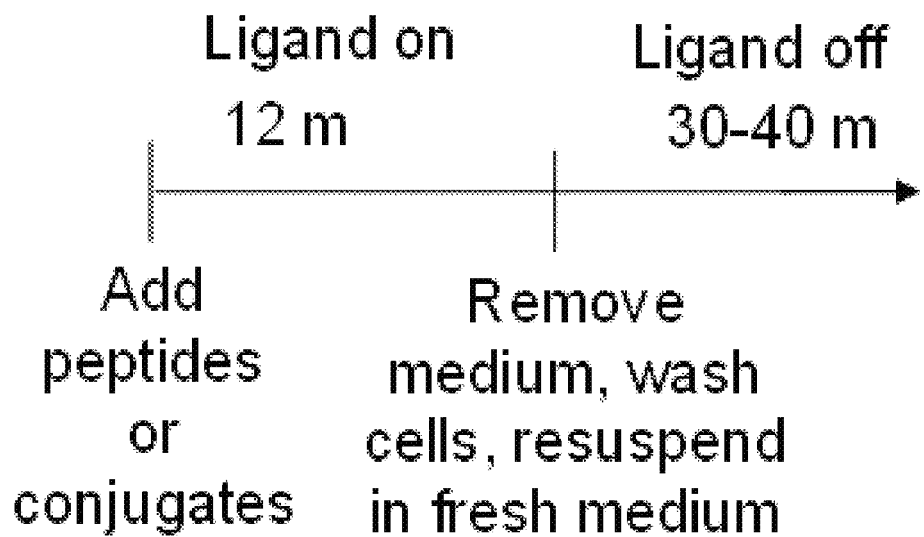
FIGS. 24A-24H: VHH anchoring of PTH fragments prolongs cAMP signaling. Cells were treated with peptides or conjugates at concentrations listed in the legend for each figure to stimulate cAMP responses as described in methods.
Figure 24B:
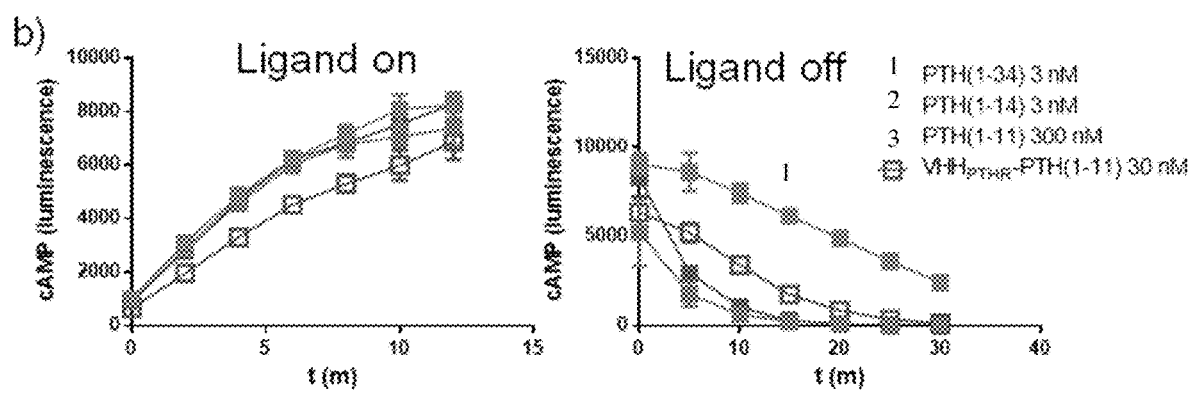
Figure 24C:
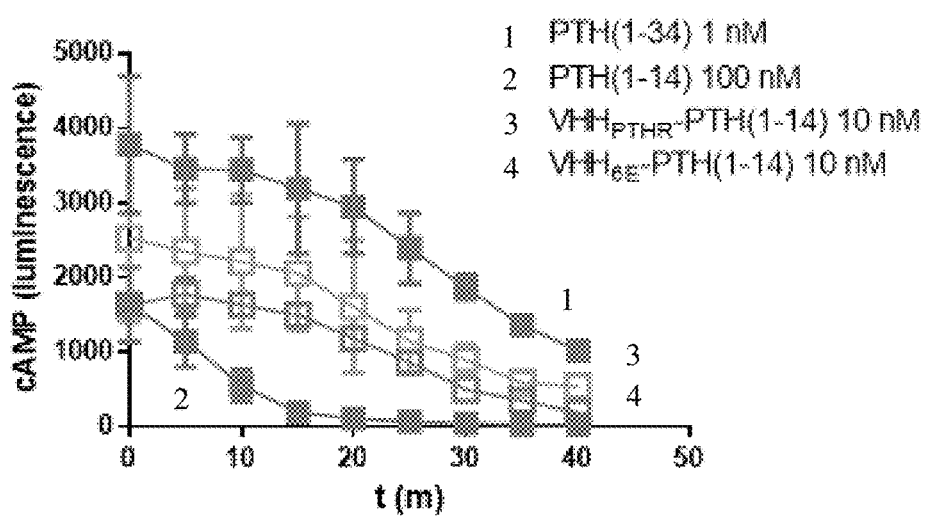
Figure 24D:
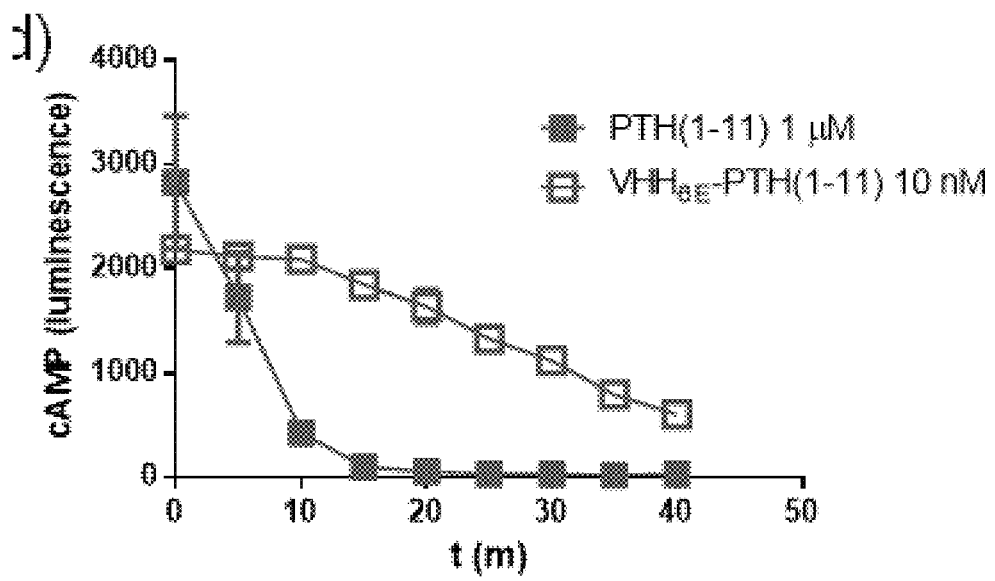
Figure 24E:
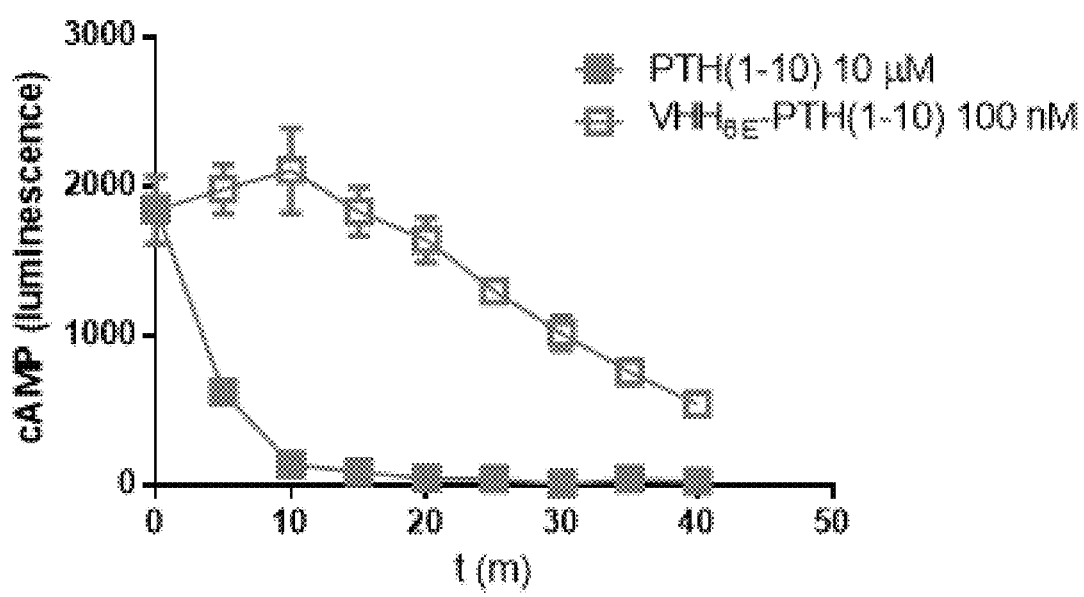
Figure 24F:
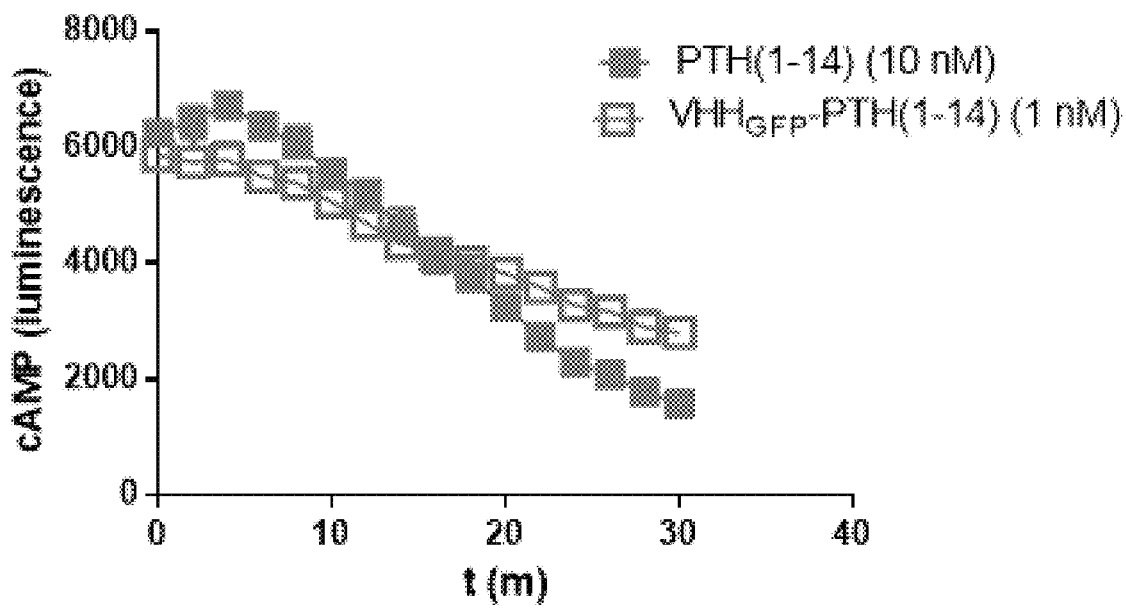
Figure 24G:
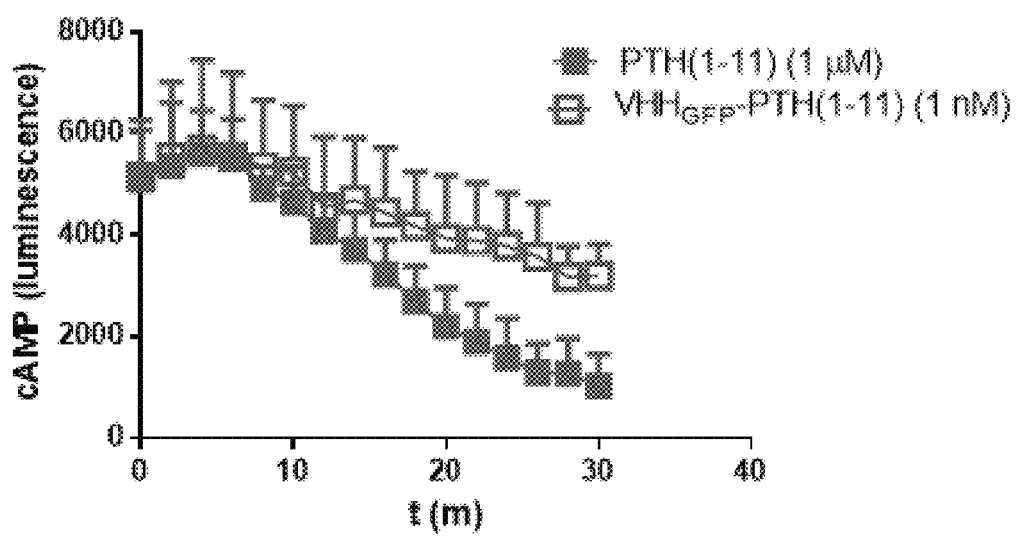
Figure 24H:
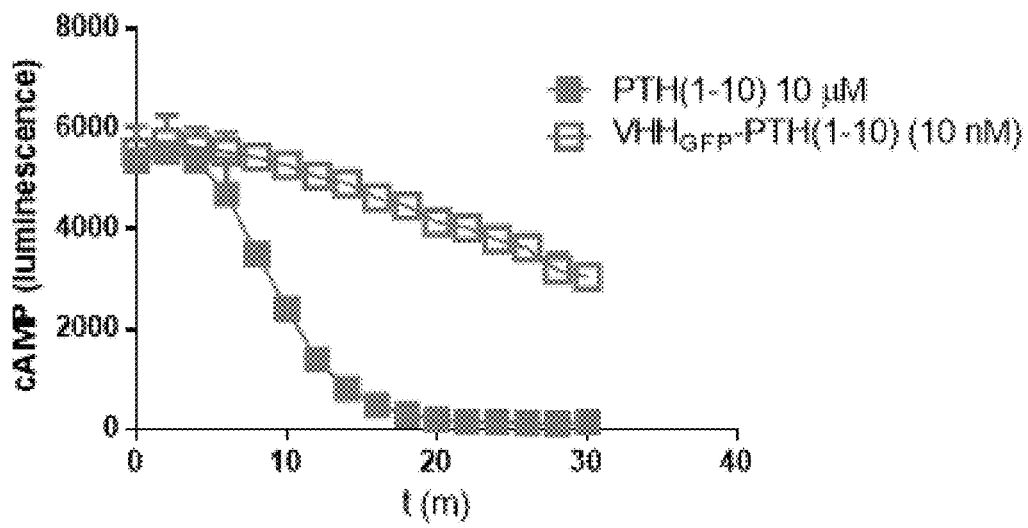

Peptide ligands of PTHR1 and conjugation to antibody fragments. To test whether delivery of PTH fragments to their site of action by conjugation to VHHs affects their signaling activity, the N-terminal fragments of PTH was synthesized (FIGS. 13A to 13C, Table 4, FIGS. 22A to 22E). These fragments were prepared as C-terminal amides by conventional solid-phase peptide synthesis, purified, and their identities were confirmed by mass spectrometry (FIGS. 13A to 13C, FIG. 18). Most of these peptides contained several of the modifications found in the "M"-PTH series of PTH peptides, including the non-standard residue aminoisobutyric acid (Aib) at position 3, which enhances the biological activity of these short PTH fragments (FIGS. 13A to 13C)[26]. Each of these peptides contained a C-terminal cysteine (Cys). Using Cys-maleimide chemistry, a dibenzylcyclooctyne (DBCO) handle (FIG. 18) was appended to enable an azide-alkyne conjugation between the C-termini of an azide-functionalized VHH and a DBCO-modified synthetic peptide. Of note, the resulting triazole linkage is not susceptible to cleavage by reduction, as are the disulfide linkages used in other conjugates. The composition of the conjugates was confirmed by mass spectrometry (FIGS. 13A to 13C, FIG. 19). For comparison, conjugates were also prepared in which a PTH(1-14) analogue with an N-terminal triglycine extension (G$_3$-PTH(1-14)) was conjugated to VHHs using sortagging, resulting in a conjugate with the C—N configuration (FIGS. 23A to 23C).

The capacity of these peptides was then assessed and conjugates to stimulate the production of cyclic adenosine monophosphate (cAMP), a second messenger molecule produced upon PTHR1 activation, using HEK293 cells expressing a targeted PTHR variant and a luciferase-based cAMP-responsive reporter[30]. Progressive truncation of C-terminal residues from PTH(1-34) caused a marked loss in the potency on wild-type PTHR1 and other PTHR1 variants with intact ECDs (Table 4, FIGS. 22A to 22E). Addition of a triglycine appendage at the N-terminus of PTH(1-14) caused a reduction in potency, relative to PTH(1-14) with a free N-terminal amine (FIGS. 23A to 23C), in line with precedent[31]. Conjugates in which G$_3$-PTH(1-14) was ligated to the VHH C-terminus using sortase were completely inactive, emphasizing the importance of a free N-terminus for PTH (FIGS. 23A to 23C). In contrast, conjugates formed by C-to-C-terminal fusion were active (Table 4, FIGS. 22A to 22E).

The conjugation of PTH fragments lacking residues 15-34, known to be important for ECD binding, to VHHs that bound to the targeted receptor enhanced potency (Table 4). For example, VHH$_{GFP}$-PTH(1-10) is 7,800-fold more potent than PTH(1-10) on PTHR1$_{YFPΔECD}$. The potency of VHH$_{GFP}$-PTH(1-10) at PTHR1$_{YFPΔECD}$ (EC$_{50}$~0.5 nM) is especially notable given that PTH(1-34), an analogue with properties similar to naturally occurring PTH, is relatively weakly active (EC$_{50}$>500 nM) on this receptor. VHH$_{PTHR}$ conjugation also increases the potency of PTH(1-11) and PTH(1-14) at PTHR1, PTHR1$_{GFP}$, and PTHR1$_{6E}$; in line with results from VHH binding experiments (FIG. 20). This finding indicates that recognition by VHH$_{PTHR}$ is not impaired by modifications in the portion of receptor encoded by exon 2. As an example, VHH$_{PTHR}$-PTH(1-14) is 57-fold more potent than PTH(1-14) on cells expressing wild-type PTHR1. Even VHHs that showed weak staining of the relevant cell lines in cytofluorimetry assays, like that of VHH$_{GFP}$ on PTHR$_{GFP}$ expressing cells, still enhanced the signaling activity of N-terminal fragments like PTH(1-11) (FIGS. 17A to 17C). Signaling duration, as assessed using a previously validated method[26, 28, 32], is also prolonged for the shorter PTH fragments upon their conjugation to the appropriately specific VHH (FIGS. 24A to 24H). The kinetics of the cAMP signaling induced by some VHH-PTH fragments resemble that seen with PTH(1-34) (FIGS. 24A to 24H). Past work has shown a correlation between the ability of a ligand to induced prolonged signaling at PTHR1 and its ability to continue to signal following internalization into endosomal compartments, with PTH(1-34) serving as a prime example[26]. The prolonged signaling of VHH-PTH conjugates relative to the corresponding free peptides suggests that the added affinity provided by VHH binding may enable endosomal signaling.

Figure 25:
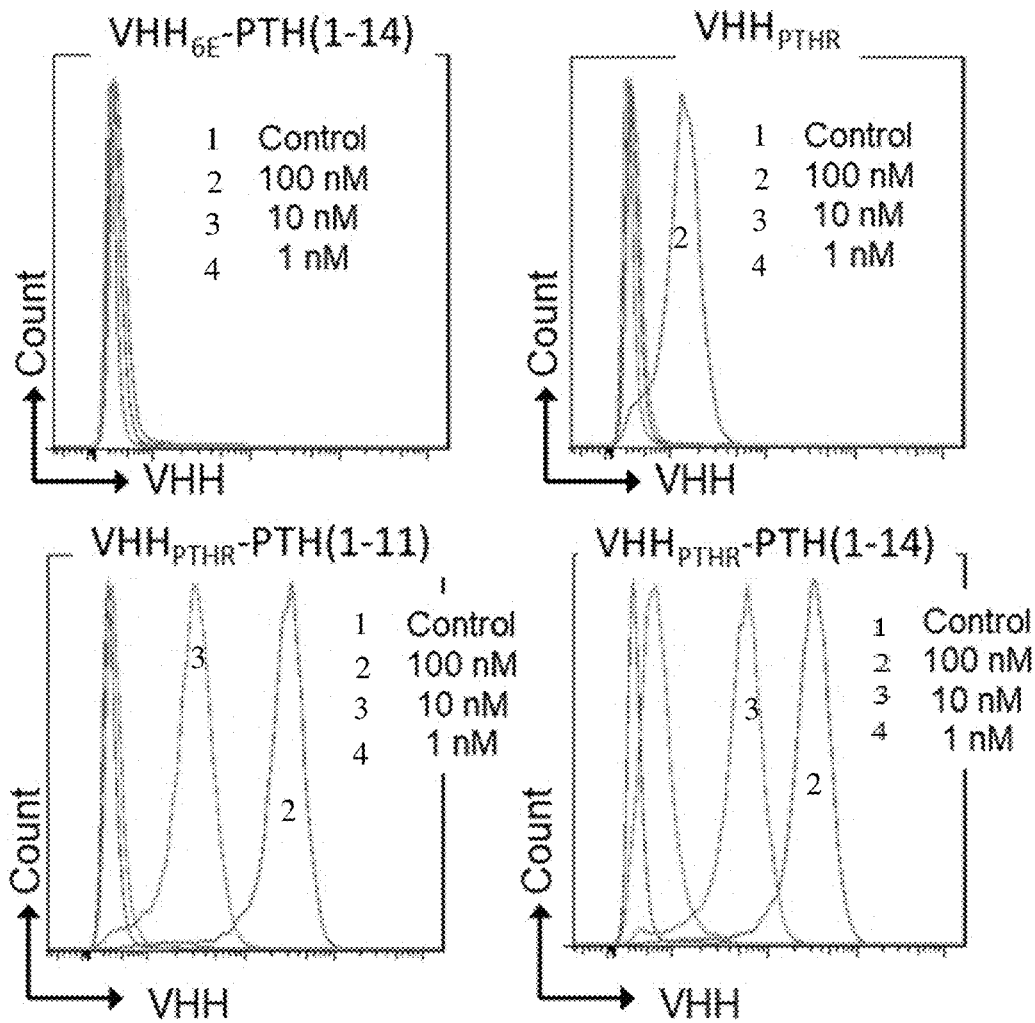
FIG. 25: Variation in binding caused by conjugation of receptor-binding or irrelevant VHHs. HEK293 cells expressing PTHR1 were stained with conjugates indicated in panels a-d at concentrations listed in legends and prepared for analysis by flow cytometry as described in methods. The control staining condition for each panel was staining with VHH$_{6E}$-biotin-azide used at a concentration of 100 nM. For VHH$_{PTHR}$, VHH$_{PTHR}$-biotin-azide was used for staining.
Figure 26A:
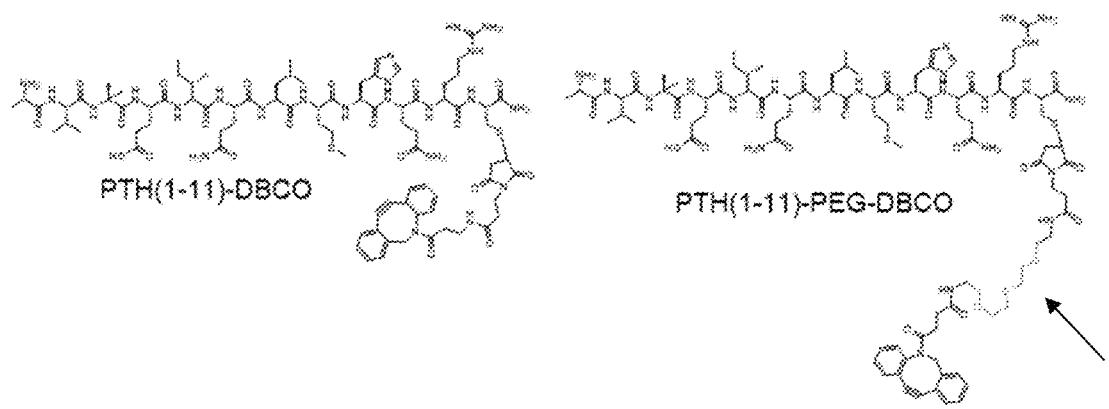
FIGS. 26A-26F: Impact of DBCO conjugation and PEG linker insertion on peptide and conjugate bioactivity. Peptides and VHH-peptide conjugates were assessed for cAMP induction in HEK293 cell lines as described in methods. Data points represent mean±SD and connecting lines result from the fit of a four-parameter sigmoidal dose-response model.
Figure 26B:
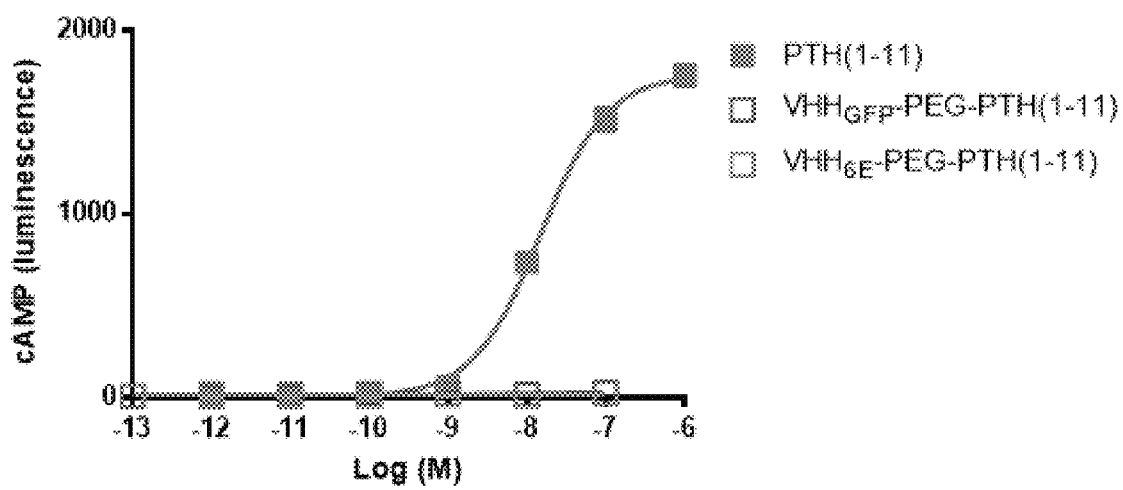
Figure 26C:
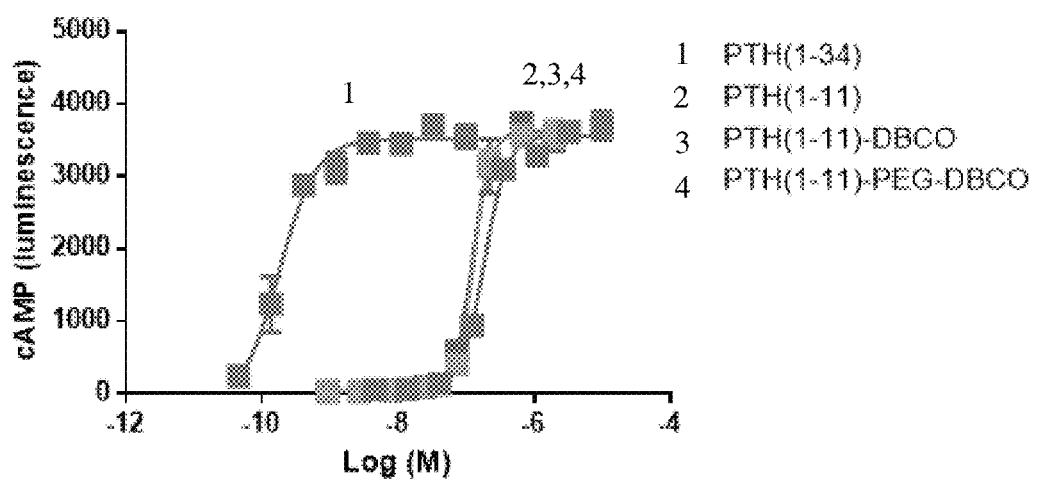
Figures 26D, 26E:
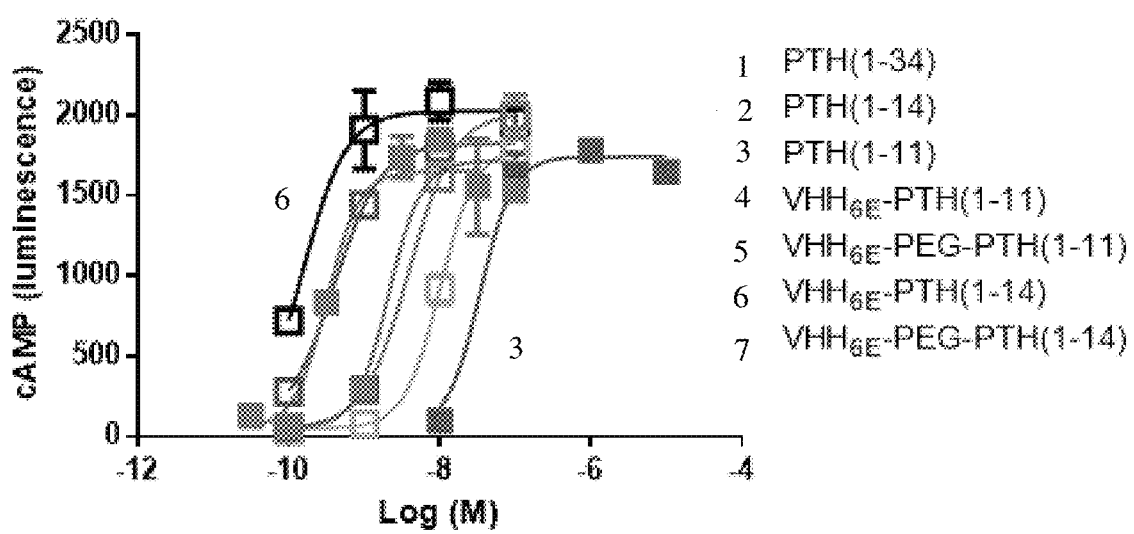
Figures 26F, 27A:
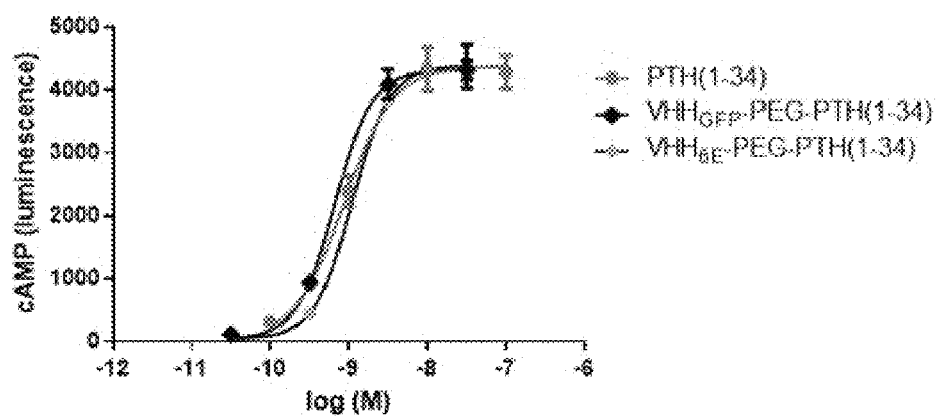
FIGS. 27A-27B: VHH conjugation does not affect signaling capacity of PTH(1-34). PTH(1-34)-Cys was conjugated to VHH with an intervening PEG$_3$ linker as described in FIGS. 13A to 13C and FIGS. 24A to 24H.
Figure 27B:
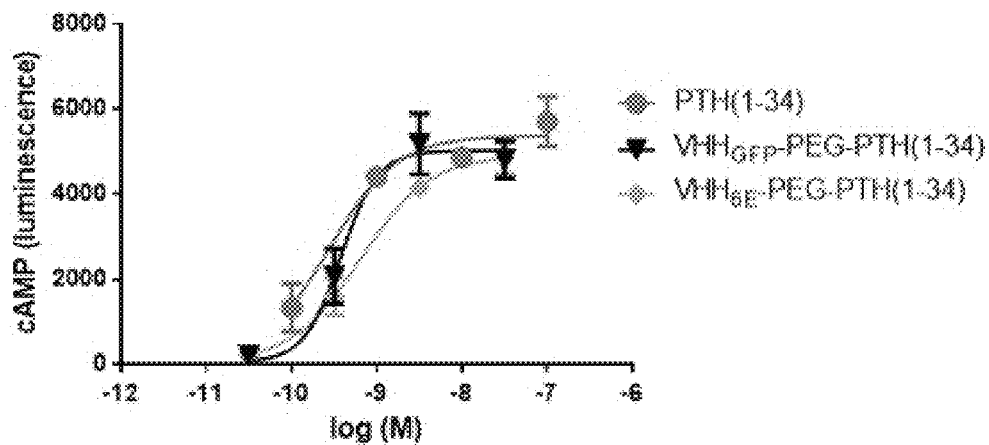

In contrast to the increase in signaling activity provided by the conjugation of PTH fragments with receptor binding VHHs, conjugation of active PTH fragments with irrelevant VHHs is detrimental to activity on the intact PTHR1. For example, conjugates of VHH$_{6E}$ and VHH$_{GFP}$ with PTH(1-11) and PTH(1-14) are inactive on wild-type human PTHR1 at the highest concentrations tested, even though the peptides themselves are quite active (Table 4, FIGS. 22A to 22E). This loss of activity is caused at least in part by a loss in receptor binding for PTH fragments conjugated to irrelevant VHHs (FIG. 25). VHH$_{6E}$-PTH(1-14) fails to bind hPTHR1 expressing cells whereas VHH$_{PTHR}$-PTH(1-14) binds more tightly than VHH$_{PTHR}$ alone. The impact of irrelevant VHH conjugation is not explained by variation in signaling activity caused by the chemical handles installed for azide-alkyne conjugation chemistry (FIGS. 26A to 26F). Furthermore, the length of the VHH-PTH linker is not a strong determinant of conjugate signaling activity or specificity: incorporation of a PEG$_3$ linker has minimal impact (FIGS. 26A to 26F). The enhancements in signaling activity provided by VHH conjugation is not seen with PTHR1 ligands that bind through both ECD and transmembrane domain interactions irrespective of VHH conjugation: conjugates of PTH(1-34) and VHHs exhibit potent biological activity regardless of whether the target of the VHH is present on the cell line tested (FIGS. 27A to 27B). VHH$_{PTHR}$-PTH(1-14) activated PTHR1$_{YFPΔECD}$ even though the nanobody does not bind this receptor (Table 4).

Figure 28A:
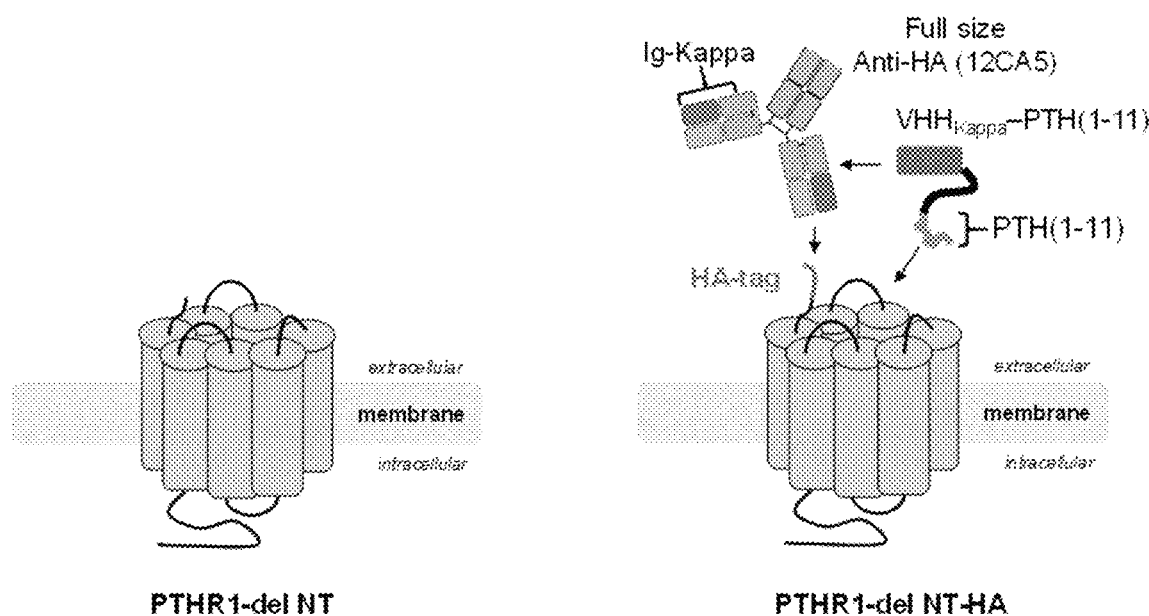
FIGS. 28A-28B: Targeting PTHR1 lacking extracellular domain. HEK293 cells stably expressing cAMP-responsive luciferase were transiently transfected with either rat PTHR1 lacking extracellular domain (rPTHR1-delNT) or a construct with an HA tag inserted in place of the extracellular domain (rPTHR1-delNT-HA). See below for sequences.
Figure 28B:
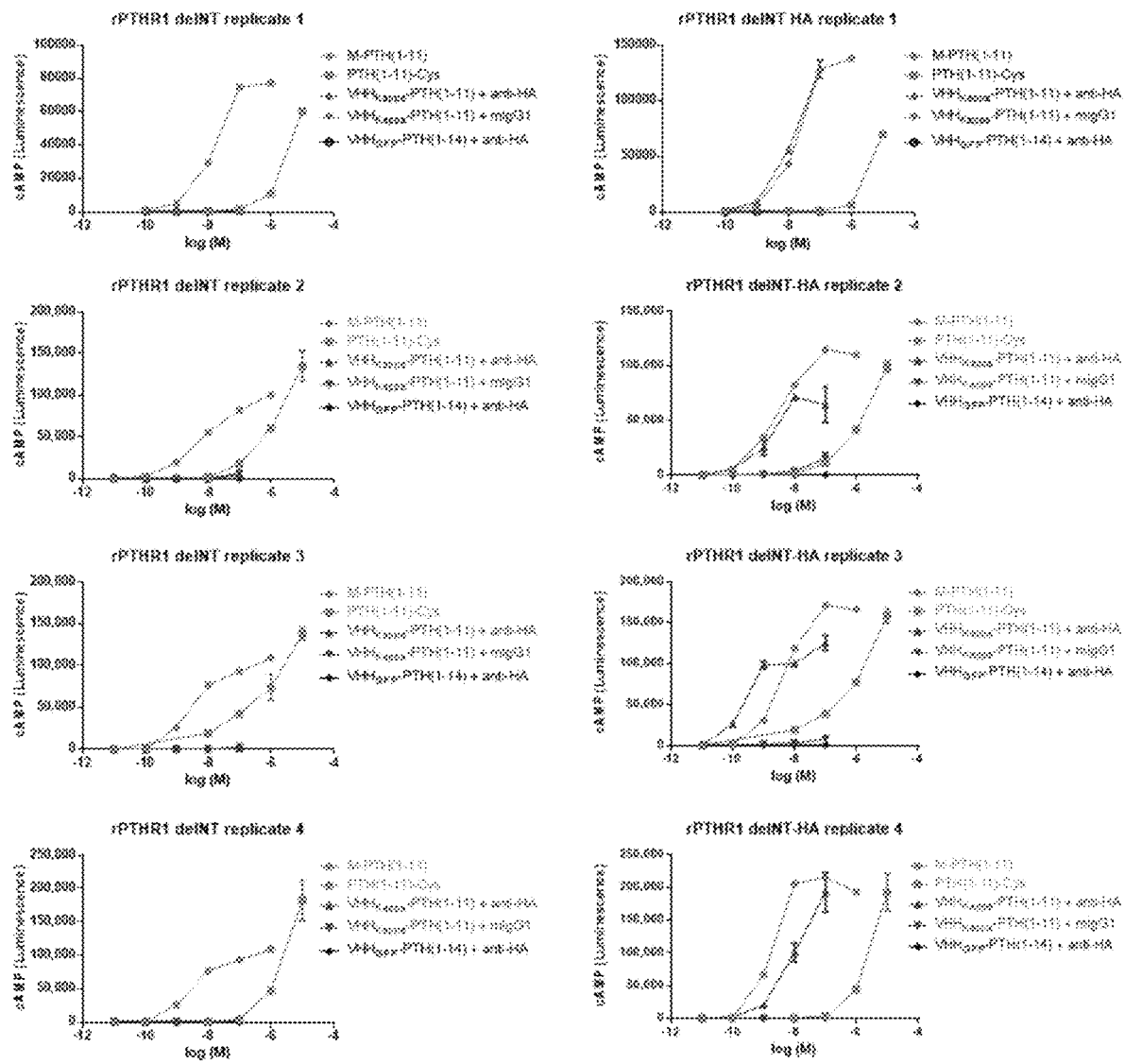

Among the GPCR superfamily, family B GPCRs have relatively large ECDs. To assess whether the CLAMP approach might also be useful for GPCRs with smaller ECDs, an alternate approach for targeting a variant of PTHR1 was developed in which the ECD is replaced by a common epitope tag (HA-tag, PYDVPDYAGGGG (SEQ ID NO: 97), FIGS. 28A to 28B). Since there are no VHHs that target the HA tag, a mouse monoclonal antibody (anti-HA, 12CA5, IgG2b-kappa) was used to target this receptor and a VHH that binds to the mouse kappa light chain (VHH$_{Kappa}$, previously named TP1170)[33] as an indirect means of tethering PTH(1-11) to the truncated receptor (FIGS. 28A to 28B). Simultaneous application of anti-HA and VHH$_{Kappa}$-PTH(1-11) activated PTHR1-delNT-HA more effectively than PTH(1-11) (FIGS. 28A to 28B). In control experiments PTHR1-delNT (no HA tag) was not activated by VHH$_{Kappa}$-PTH(1-11). Neither anti-HA nor VHH$_{Kappa}$-PTH(1-11) alone were capable of activating PTHR1-delNT-HA.

Figure 29A:
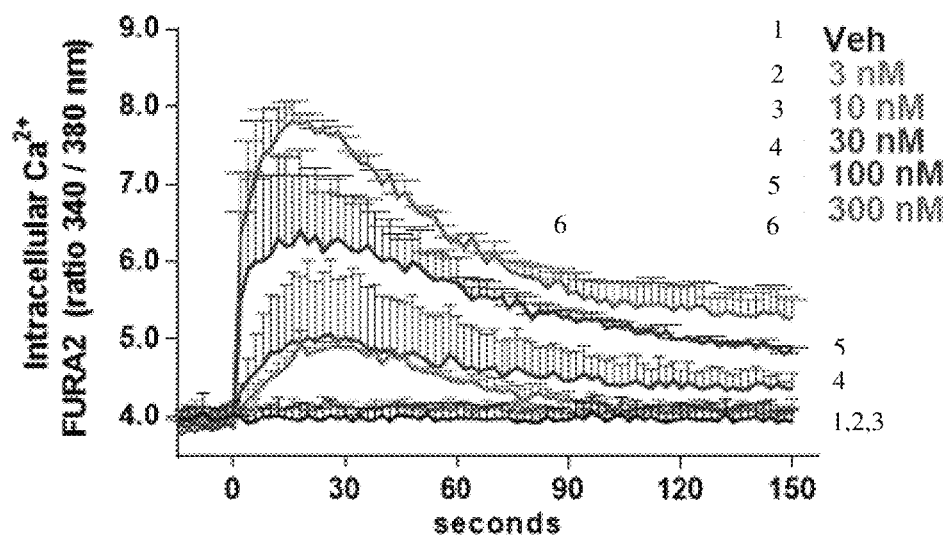
FIGS. 29A-29C: Measurement of cytoplasmic calcium mobilization by PTHR1 agonists.
Figure 29B:
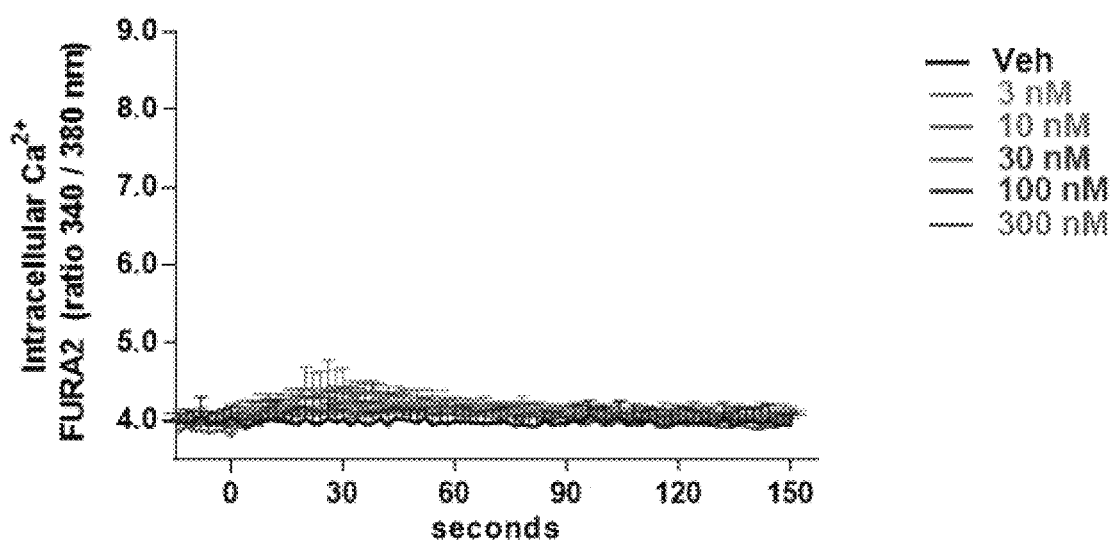
Figure 29C:
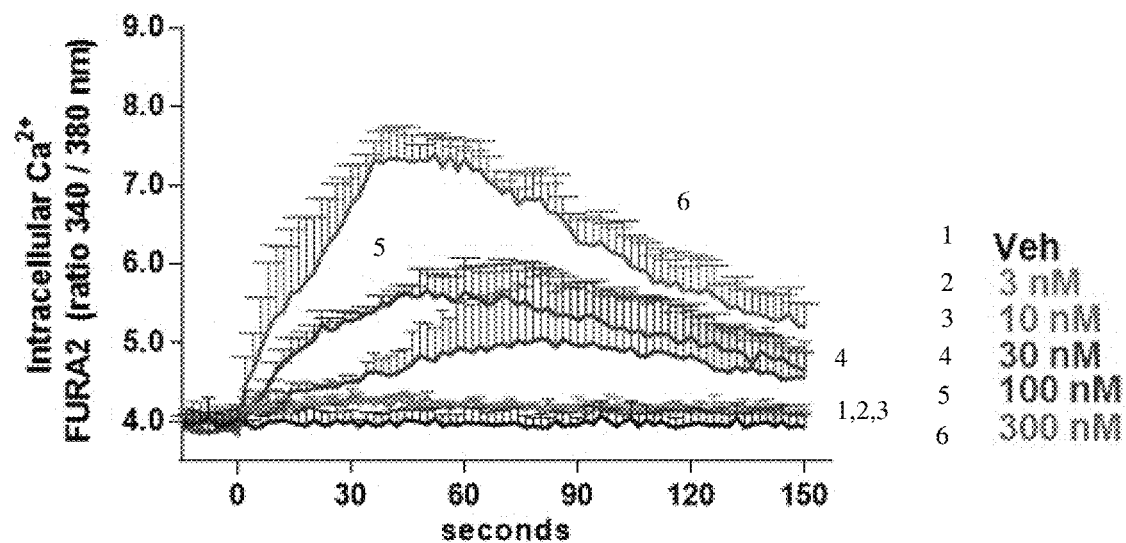
Figure 30A:
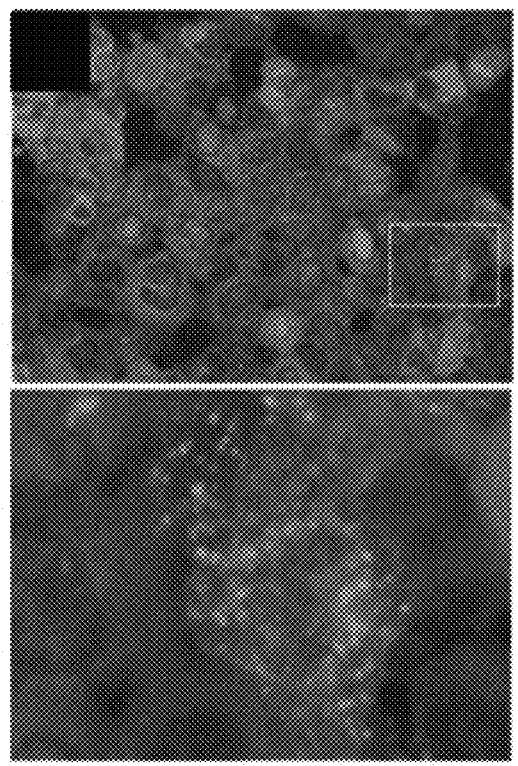
FIGS. 30A-30F: Assessment of β-arrestin recruitment. A HEK293-derived cell line stably expressing a β-arrestin2-YFP fusion[2] was transiently transfected with human PTHR1. Some panels show cells stained with PTH(1-34)- tetramethylrhoadmine conjugate [PTH(1-34)-TMR] (red) and the nuclei of all cells were counterstained with DAPI.
Figure 30B:
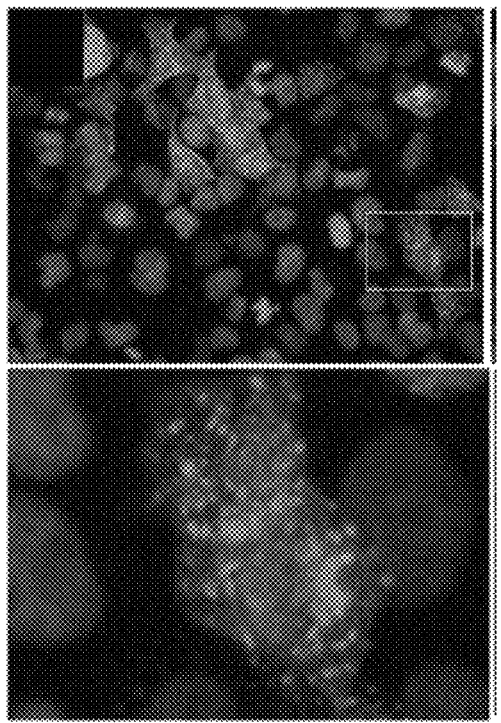
Figure 30C:
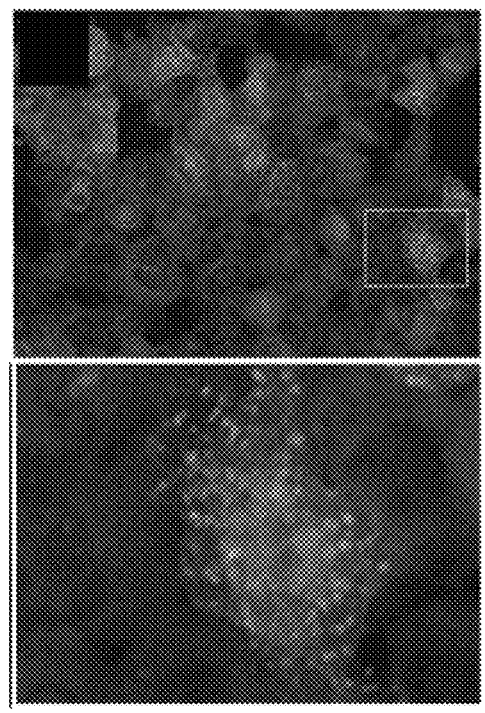
Figure 30D:
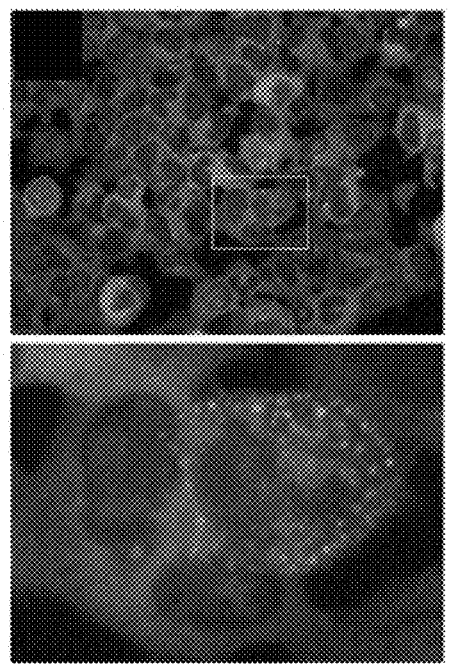
Figure 30E:
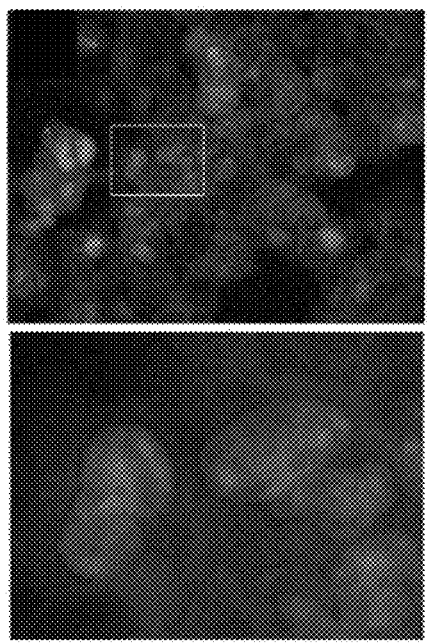
Figure 30F:
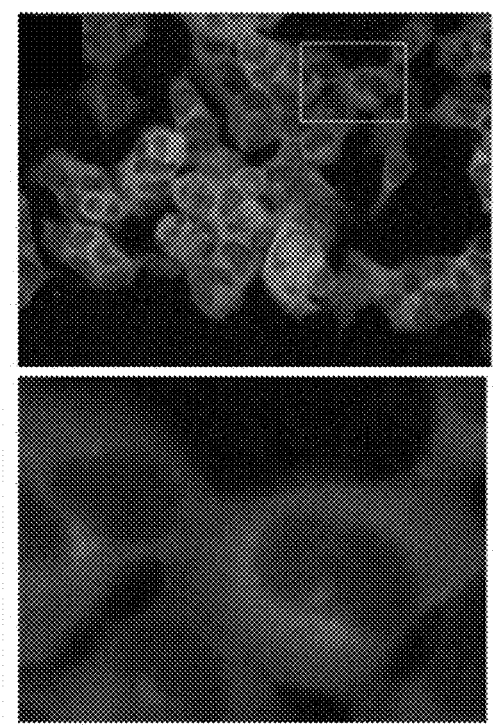
Figure 31:
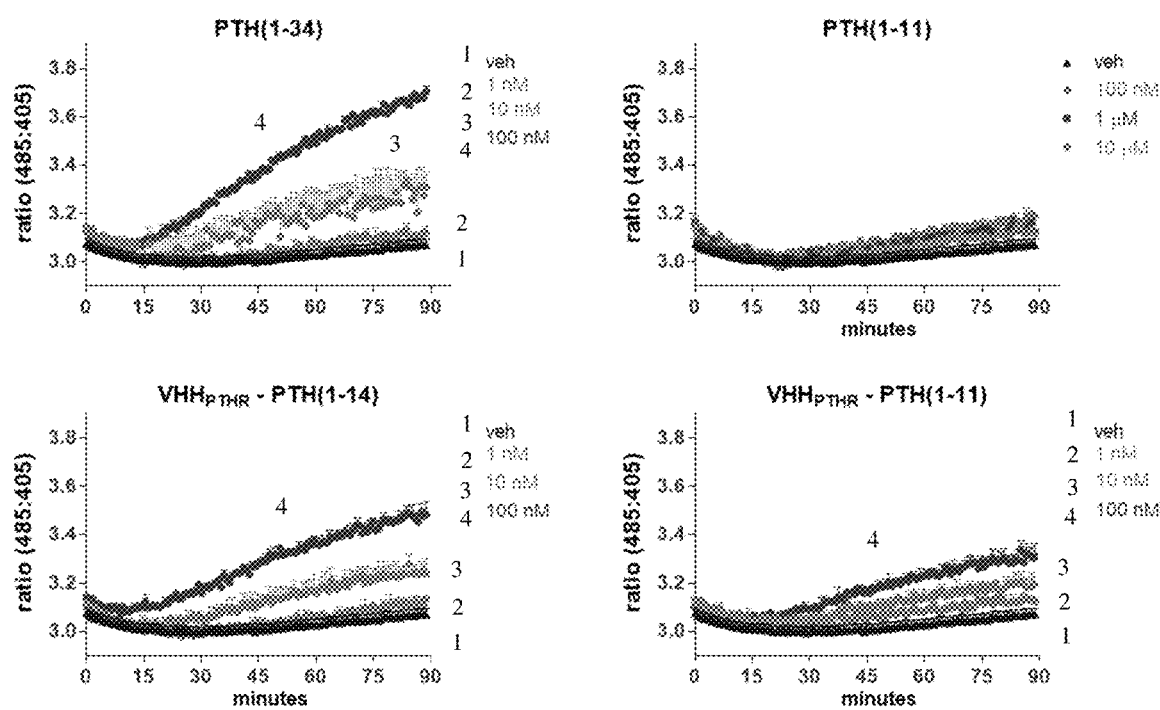
FIG. 31: Assessment PTHR1 internalization. A HEK293-derived cell line stably expressing a PTHR1-GFP-pHluorin2 was treated with a PTH peptide or VHH-peptide doses at the indicated doses. The ratio of fluorescence intensity at 535 nm following excitation at either 485 nm or 405 nm was measured over time. Data points indicate mean±SEM. These data are representative of two independent replicates experiments.

Activated GPCRs can signal through more than one intracellular pathway, at the cell surface or from internalized compartments. There is interest in identifying ligands that are functionally selective in signaling through one pathway over another (biased agonists)[34]. PTHR1 signals through multiple pathways including Gs/protein kinase A (PKA)/cAMP, Gq/phospholipase C (PLC)/Ca$^{2+}$, and β-arrestin/ERK[35]. It was tested whether selected VHH-PTH conjugates engaged these pathways. It was found that VHH$_{PTHR}$-PTH(1-14) but not VHH$_{PTHR}$-PTH(1-11) stimulated signaling though the Gq/PLC/Ca$^{2+}$ signaling pathway in cells expressing human PTHR1 (FIGS. 29A to 29C). VHH$_{PTHR}$-PTH(1-11) appears to be selective for Gs/PKA/cAMP signaling, although assessing Gq signaling at higher conjugate concentrations than currently possible or using different assay formats may reveal weak activity. PTHR1 signaling through the Gq pathway has been shown to be more sensitive to structural modifications and alterations in affinity than signaling through the Gs pathway[8, 35], in line with these findings. The capacity of VHH$_{PTHR}$-PTH(1-14) was also assessed to induce PTHR1 to recruit β-arrestin. It was found that PTH(1-34) and VHH$_{PTHR}$-PTH(1-14) (FIGS. 30A and 30D), but not VHH$_{PTHR}$ alone (FIG. 30E), effectively stimulated the relocalization of cytoplasmically dispersed YFP-tagged β-arrestin to distinct puncta. Colocalization of a fluorophore-tagged PTH(1-34) with YFP-β-arrestin in puncta supported the specificity of arrestin recruitment to the agonist-occupied PTHR1 (FIG. 30C). Many of the puncta observed in cells treated with PTH(1-34) or VHH$_{PTHR}$-PTH(1-14) were observed near the nucleus, which is consistent with ligand-induced internalization. Ligand-induced internalization was further assessed through the use of cells expressing PTHR1-GFP, in which the GFP variant is pH-sensitive. Since the spectral properties of this GFP variant change as a function of pH[19], the movement of the receptor from the cell surface into the acidic endolysosomal compartment can be assessed by monitoring at times after ligand addition the change in fluorescence at two wavelengths (FIG. 31). In this assay VHH$_{PTHR}$-PTH(1-14) behaves similarly to PTH(1-34), an agonist known to induce PTHR1 internalization[35], providing further evidence that VHH$_{PTHR}$-PTH(1-14) induces internalization. In total, VHH$_{PTHR}$-PTH(1-14) behaves similarly to PTH(1-34) in each of the cell-based bioassays tested.

Figure 15A:
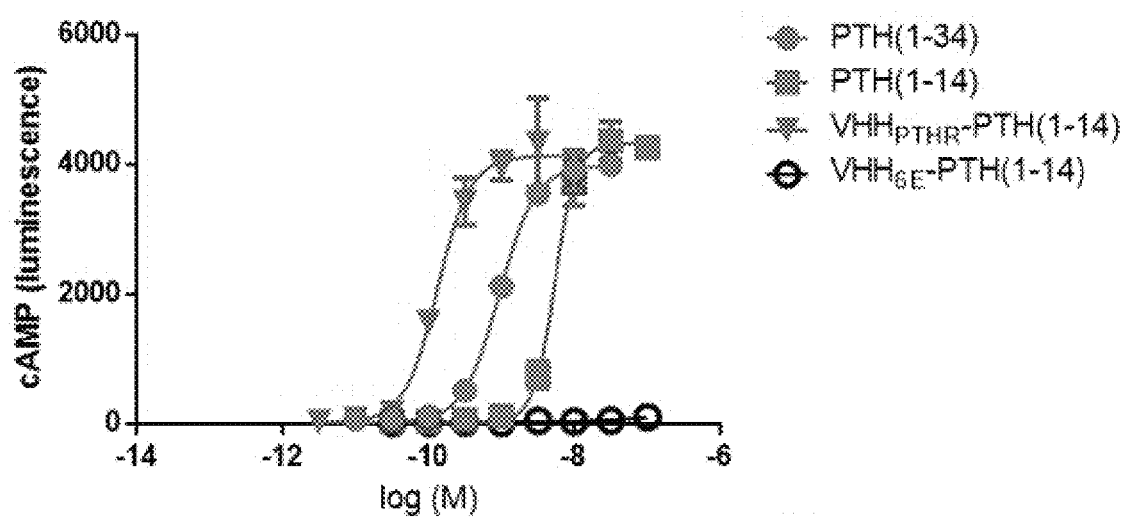
FIGS. 15A-15C: Selective and potent activation of PTHR1 via VHH$_{PTHR}$ conjugation. HEK293 cell lines stably expressing either human PTHR1 (hPTHR1) or hPTHR2 were treated with varied doses of the indicated peptides or conjugates and activation was assessed by cAMP production.
Figures 15B, 15C:
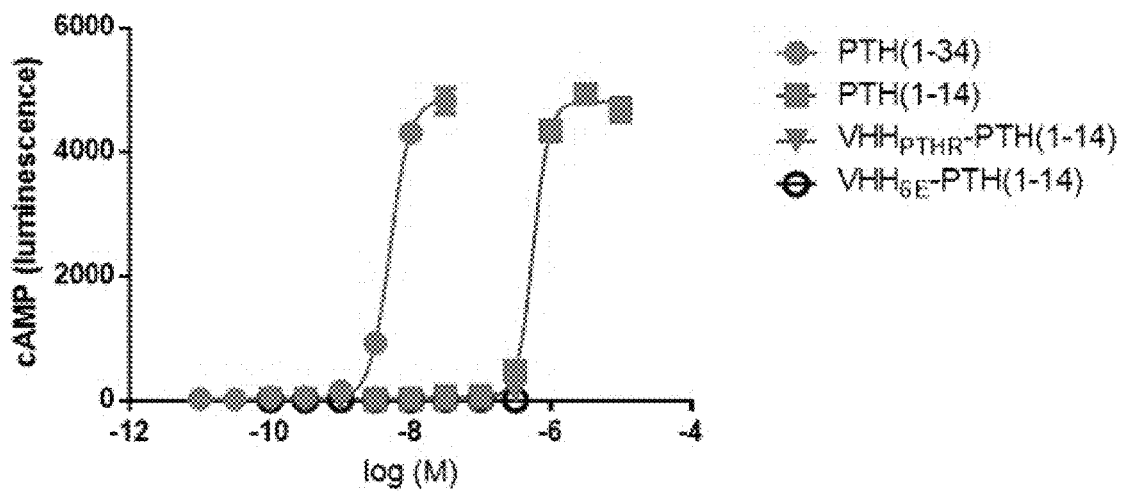

The increase in biological activity and selectivity of PTH fragments seen through conjugation to VHHs led us to test whether the same enhancements in activity applied to two naturally occurring subtypes of PTHR. PTH(1-34) tightly binds and activates both PTHR1 and PTHR2[8]. VHH$_{PTHR}$ binds to PTHR1 but not PTHR2 (FIGS. 14A to 14B). VHH$_{PTHR}$-PTH conjugates should therefore activate PTHR1 but not PTHR2. Conjugates of PTH(1-14) were focused on as this fragment also activated PTHR1 and PTHR2 (FIGS. 15A to 15C). The VHH$_{PTHR}$-PTH(1-14) conjugate activated PTHR1 more potently than any other compound tested in this study (EC$_{50}$~0.07 nM), whereas it was completely inactive at PTHR2 at 330 nM (>4,500-fold selectivity for PTHR1, FIGS. 15A to 15C). This contrasts with the lack of selectivity of PTH(1-34) in this study (5-fold selectivity for PTHR1) and in past work[8].

Figure 16A:
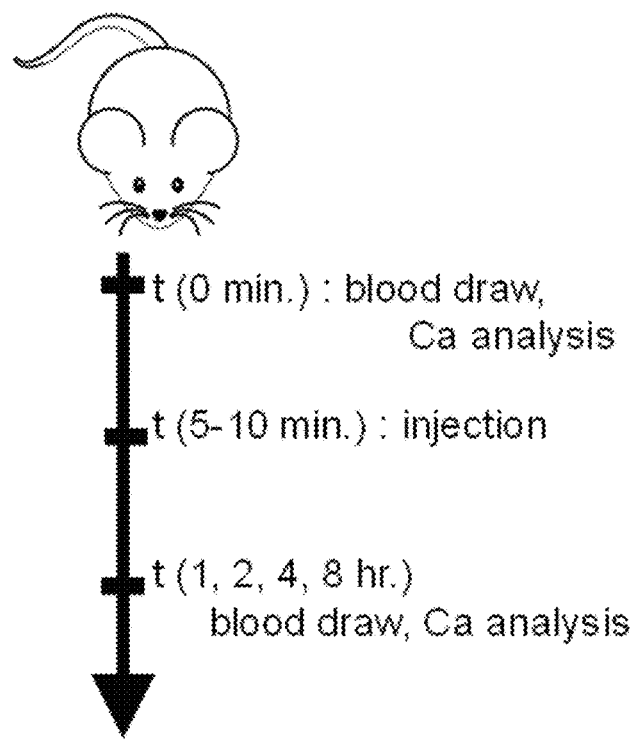
FIGS. 16A-16B: VHH conjugation potentiates an in vivo response.
Figure 16B:
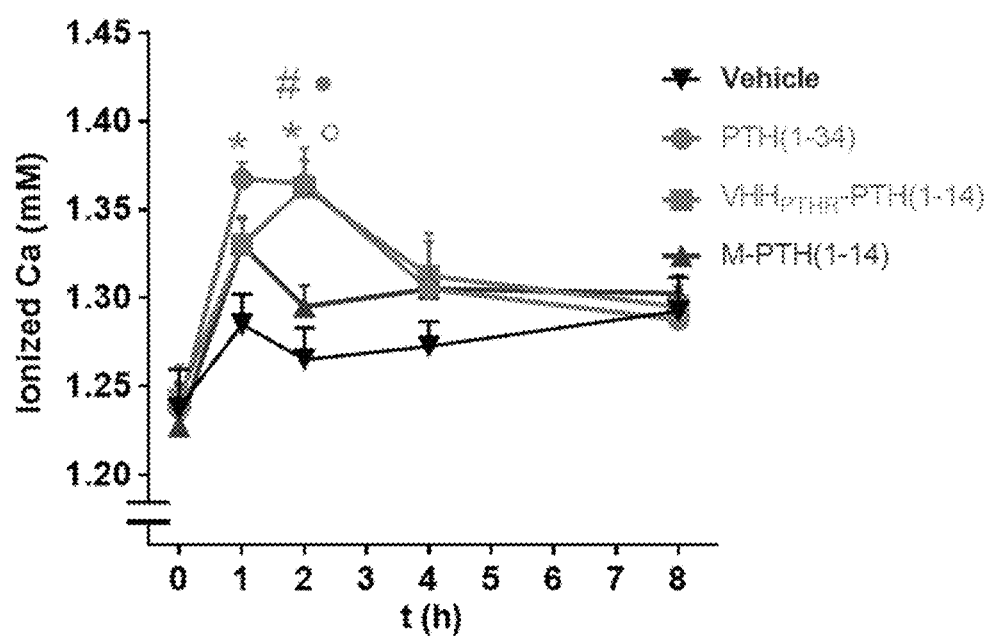
Figures 32A, 32B:
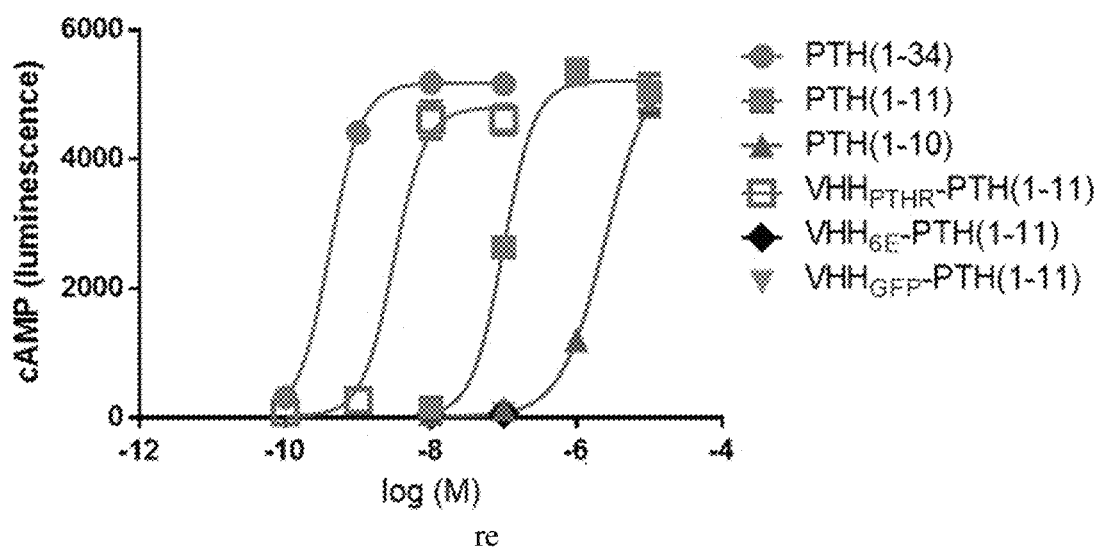
FIGS. 32A-32B: $VHH_{PTHR}$ conjugation potentiates PTH fragment activation of rat PTHR1. HEK293 cells stably expressing rat PTHR1 were stimulated with peptide or conjugate as described in methods.

In vivo activity. It was tested whether the potent biological activity observed for VHH-PTH conjugates in cell-based assays would extend to an in vivo setting. The VHH$_{PTHR}$-PTH(1-14) conjugate was used in these experiments because it was more potent than VHH$_{PTHR}$-PTH(1-11). VHH$_{PTHR}$ potentiated PTH(1-11) signaling activity for the rat PTHR1 (FIGS. 32A to 32B). Since VHH$_{PTHR}$ bound rat PTHR1 (FIGS. 14A to 14B), is would also bind mouse PTHR1, as these receptors are nearly identical (99% identical in their extracellular domain). To measure in vivo activity, the mice were injected subcutaneously with equimolar amounts of either PTH(1-34), M-PTH(1-14), VHH$_{PTHR}$-PTH(1-14), or saline. PTH(1-34) induced a strong increase in blood ionized calcium levels, which peaks 1-2 h after injection and returns to baseline thereafter, whereas free M-PTH(1-14) exhibits little if any activity in this assay, in line with past findings[26]. The experiment showed that VHH$_{PTHR}$-PTH(1-14) stimulated a spike in blood calcium that peaked two hours after injection (FIGS. 16A to 16B). The conjugation of PTH(1-14) with VHH$_{PTHR}$ therefore potentiates biological activity both in cell-based assays and in vivo.

DISCUSSION

Antibodies as part of conventional antibody-drug conjugates deliver cytotoxic compounds that typically target intracellular proteins[1, 2]. Less explored is the use of antibodies to deliver ligands for surface receptors, such as GPCRs. This is likely due in part to complications in preparing homogenous and bioactive conjugates of antibodies and ligands that rely on antibody binding to potentiate engagement of receptor by the ligand. The immunocytokines (conjugates of cytokines and antibodies) are an exception[36]. Immunocytokines have been characterized in cell- and animal-based models and have progressed to the clinic, but not without toxicity, suggesting an insufficiency in targeting[36]. In one case, even the identity of the targeting antibody of the immunocytokine was irrelevant for in vivo efficacy[37]. The introduction of mutations in cytokines to improve the selectivity of immunocytokines can dampen the affinity of cytokines for their receptors[38, 39] Immunocytokine-based approaches differ from the CLAMP platform in that they rely on genetic fusions (and genetically encoded residues) and the use of full-size cytokine domains, as opposed to the small peptide fragments with non-natural residues used here.

In one precedent for targeting GPCRs with antibody-ligand fusions, VHH$_{GFP}$ equipped with a SNAP-tag was linked to a photoactivatable ligand for the GPCR mGluR2[40]. This fusion was then used to activate a GFP-tagged receptor upon photoactivation of the ligand. The response induced by a saturating solution of the photoactivatable VHH-ligand conjugate was ~40% as strong as that induced by a saturating solution of natural ligand and moreover required the use of a receptor-GFP fusion[40]. This precluded the use of genetically unmodified cells or animals. In another example, full-length anti-PKSK9 antibodies fused at the N-terminus of the heavy or light chain with analogues of the glucagon-like peptide 1 (GLP-1) were produced[41]. However, most of the fusions tested were expressed in low yield, isolated with inactivating truncations in the GLP-1 fragment, unstable in solution, or were degraded rapidly in vivo, demonstrating the difficulties encountered when expressing fusion proteins comprised of full-length antibodies and ligands of interest[41].

Despite several screening campaigns, no VHHs that directly activate GPCRs have been identified[5]. A library of C-to-C terminal fusions of VHHs and synthetic PTH peptides was prepared. The use of C-to-C fusions is supported by the lack of activity of the corresponding N-to-C fusions (FIGS. 23A to 23C). It is possible that the genetic fusion of PTH peptides to the N-terminus of VHHs might be accommodated with retention of both VHH binding and PTH activity, this would require a unique genetic construct and optimization of expression for each fusion. This complication was avoided through the chemoenzymatic approach. A further benefit of this synthetic strategy is the ease of incorporation of non-natural residues such as Aib into the synthetic peptide portion of the conjugate to improve proteolytic stability[41]. Several conjugates stimulated cAMP responses with potencies similar to that of PTH(1-34) (Table 4). Even PTH(1-9), which fails to activate PTHR1 unless tethered directly to the receptor's N-terminus via genetic fusion[42], showed activity when conjugated to a VHH (Table 4). VHH-mediated delivery of ligands should enable identification of weak ligands that might otherwise be dismissed as completely inactive. Similar observations were made in evaluating conjugates consisting of peptide fragments derived from the N- and C-termini of corticotrophin releasing factor-1, which were weakly active or inactive alone, but once assembled via click chemistry, several conjugates were potent agonists[43].

Agonist activity for VHH-PTH conjugates was dependent on binding of the VHH to the receptor being targeted: a mismatch between specificity of the VHH and the receptor construct led to a loss in conjugate activity. A conjugate, $VHH_{PTHR}$-PTH(1-14), was identified with very potent signaling activity in cell-based assays (Table 4), with biological activity in mice (FIGS. 16A to 16B), and with selectivity for PTHR1 over PTHR2 that far surpasses the selectivity of PTH(1-34), the prototypical PTHR1 agonist (FIGS. 15A to 15C) used clinically. PTHR1 is known to mediate the biological activity of PTH in treating osteoporosis, whereas the function of PTHR2 is more obscure. Tools to selectively target PTHR1, and subtypes of GPCRs in other families, will be useful for dissecting the biological function of receptors for which potent and selective ligands are of limited availability. Success in targeting PTHR1 over PTHR2 sets the stage for designing ligands that specifically activate other receptors with overlapping specificities[6, 7].

The ability to deliver ligands to specific subtypes of receptors, or to receptors engineered to contain an antibody-recognized tag, should allow the creation of (modular) versions of designed receptors exclusively activated by designer drugs (DREADDs)[44]. Previously described DREADDs for GPCRs were identified through modification of the ligand binding site of naturally occurring GPCRs, so that the modified receptors respond to a "designer" small molecule but not the ligand of the prototype receptor. These designer molecules selectively activate the designer receptor but not any endogenously expressed alternative[45, 46]. A similar approach has been deployed to produce an orthogonal receptor-ligand pair for interleukin-2[47]. The finding that $VHH_{GFP}$-PTH(1-11) potently activates $PTHR1_{YFP\Delta ECD}$ ($EC_{50}$~0.15 nM) but is inactive at wild-type PTHR1, suggests a path towards using VHH-tag recognition as a way to convert a GPCR of choice into a DREADD. One aspect of GPCR pharmacology that has not been faithfully reproduced in some DREADD constructs is that of ligand binding kinetics[48]. For some receptors, such as PTHR1, the duration of ligand binding and the signaling induced as a consequence can dictate the type of physiological response evoked. The duration of the cAMP response elicited by PTHR1 activation is correlated with the strength and duration of the calcemic response in vivo[26, 49]. Several of the VHH-PTH conjugates tested here induce cAMP signaling that is prolonged relative to the free peptide and similar to that of PTH(1-34) (FIGS. 24A to 24H), suggesting that the affinity provided by VHH binding can be used as an independent means to adjust ligand binding and signaling kinetics.

In conclusion, it was shown that the conjugation of otherwise suboptimal PTHR1 agonist peptides to VHHs that target the intended receptor provides a substantial increase in agonist potency and receptor selectivity. The ability to modulate receptor affinity while not modifying the structure of the agonist used to activate signaling should enable a further dissection of connections between ligand affinity, receptor signaling kinetics, and ligand bias[50]. Preliminary analyses suggest that VHH-ligand conjugates can be designed that possess signaling properties that diverge from that of the natural ligands (Table 4, FIGS. 29A to 29C). The CLAMP platform should be amenable to targeting other GPCRs, especially those with large peptide ligands that bind to their receptors via a two-site mechanism, such as family B GPCRs and chemokine receptors.

TABLE 4

Stimulation of PTHR1 and variants by VHH-PTH conjugates.

| Peptide or conjugate | hPTHR1 (nM ± SD) | PTHR1$_{6E}$ | hPTHR1$_{YFP\Delta ECD}$ |
|---|---|---|---|
| PTH(1-34) | 0.51 ± 0.28 | 1.3 ± 1.0 | 689 ± 301 |
| PTH(1-14) | 4.3 ± 2.0 | 3.4 ± 1.6 | 1.1 ± 0.9 |
| PTH(1-11) | 516 ± 238 | 94 ± 74 | 246 ± 133 |
| PTH(1-10) | 3121 ± 1671 | 5079 ± 407 | 3841 ± 1604 |
| PTH(1-9) | Inactive at 10,000 nM | Inactive at 10,000 nM | Inactive at 10,000 nM |
| $VHH_{PTHR}$-PTH(1-14) | 0.075 ± 0.041 | 0.2 ± 0.1 | 0.9 ± 0.5 |
| $VHH_{PTHR}$-PTH(1-11) | 5.0 ± 1.6 | 4.0 ± 3.2 | Inactive at 100 nM |
| $VHH_{PPTHR}$-PTH(1-10) | Inactive at 100 nM | ND | ND |
| $VHH_{6E}$-PTH(1-14) | Inactive at 330 nM | 0.4 ± 0.2 | ND |
| $VHH_{6E}$-PTH(1-11) | Inactive at 100 nM | 6.9 ± 2.6 | Inactive at 100 nM |
| $VHH_{6E}$-PTH(1-10) | ND | 2.8 ± 1.4 | ND |
| $VHH_{6E}$-PTH(1-9) | ND | Inactive at 100nM | |
| $VHH_{GFP}$-PTH(1-14) | Inactive at 100 nM | Inactive at 100nM | 0.58 ± 0.29 |
| $VHH_{GFP}$-PTH(1-11) | Inactive at 100 nM | Inactive at 100nM | 0.14 ± 0.06 |
| $VHH_{GFP}$-PTH(1-10) | ND | ND | 0.46 ± 0.22 |
| $VHH_{GFP}$-PTH(1-9) | ND | ND | ~40% activation at 100n |

TABLE 5

Complete tabulation of cAMP induction assays.

| hPTHR1 | EC$_{50}$ (nM ± SD) | Max (normalized ± SD) | n |
|---|---|---|---|
| PTH(1-34) | 0.51 ± 0.28 | 1.00 ± 0.00 | 8 |
| PTH(1-14) | 4.3 ± 2.0 | 1.01 ± 0.07 | 5 |
| PTH(1-11) | 516 ± 238 | 1.01 ± 0.09 | 7 |
| PTH(1-10) | 3121 ± 1671 | 1.03 ± 0.08 | 3 |
| PTH(1-9) | Inactive at 10,000 nM | | 3 |
| VHH$_{PTHR}$-PTH(1-14) | 0.075 ± 0.041 | 0.96 ± 0.17 | 4 |
| VHH$_{PTHR}$-PTH(1-11) | 5.0 ± 1.6 | 0.95 ± 0.09 | 7 |
| VHH$_{PTHR}$-PTH(1-10) | Inactive at 100 nM | | 2 |
| VHH$_{6E}$_PTH(1-14) | Inactive at 330 nM | | 3 |
| VHH$_{6E}$_PTH(1-11) | Inactive at 100 nM | | 2 |
| VHH$_{6E}$_PTH(1-10) | ND | | |
| VHH$_{6E}$_PTH(1-9) | ND | | |
| VHH$_{GFP}$_PTH(1-14) | Inactive at 100 nM | | 3 |
| VHH$_{GFP}$_PTH(1-11) | Inactive at 100 nM | | 3 |
| VHH$_{GFP}$_PTH(1-10) | ND | | |
| VHH$_{GFP}$_PTH(1-9) | ND | | |

| hPTHR1$_{GFP}$ | EC$_{50}$ (nM ± SD) | Max (normalized ± SD) | n |
|---|---|---|---|
| PTH(1-34) | 0.4 ± 0.8 | 1.00 ± 0.00 | 7 |
| PTH(1-14) | 2.3 ± 1.2 | 1.09 ± 0.03 | 3 |
| PTH(1-11) | 79 ± 45 | 1.10 ± 0.13 | 7 |
| PTH(1-10) | 2552 ± 653 | 1.16 ± 0.15 | 6 |
| PTH(1-9) | Inactive at 10,000 nM | | 4 |
| VHH$_{PTHR}$-PTH(1-14) | 1.7 ± 2.3 | 1.10 ± 0.10 | 3 |
| VHH$_{PTHR}$-PTH(1-11) | 0.5 ± 0.1 | 1.03 ± 0.26 | 4 |
| VHH$_{PTHR}$-PTH(1-10) | ND | | |
| VHH$_{6E}$_PTH(1-14) | 32.9 ± 3.5 | 1.14 ± 0.08 | 3 |
| VHH$_{6E}$_PTH(1-11) | Inactive at 100 nM | | 3 |
| VHH$_{6E}$_PTH(1-10) | Inactive at 100 nM | | 3 |
| VHH$_{6E}$_PTH(1-9) | ND | | |
| VHH$_{GFP}$_PTH(1-14) | 1.8 ± 0.6 | 1.21 ± 0.17 | 3 |
| VHH$_{GFP}$_PTH(1-11) | 8.0 ± 3.4 | 1.10 ± 0.18 | 6 |
| VHH$_{GFP}$_PTH(1-10) | Inactive at 100 nM | | 3 |
| VHH$_{GFP}$_PTH(1-9) | Inactive at 100 nM | | 4 |

| hPTHR1$_{6E}$ | EC$_{50}$ (nM ± SD) | Max (normalized ± SD) | n |
|---|---|---|---|
| PTH(1-34) | 1.3 ± 1.0 | 1 ± 0.0 | 3 |
| PTH(1-14) | 3.4 ± 1.6 | 1.06 ± 0.12 | 3 |
| PTH(1-11) | 94 ± 74 | 1.09 ± 0.22 | 3 |
| PTH(1-10) | 5079 ± 407 | 1.09 ± 0.07 | 3 |
| PTH(1-9) | Inactive at 10,000 nM | | 3 |
| VHH$_{PTHR}$-PTH(1-14) | 0.2 ± 0.1 | 0.98 ± 0.19 | 3 |
| VHH$_{PTHR}$-PTH(1-11) | 4.0 ± 3.2 | 0.98 ± 0.11 | 3 |
| VHH$_{PTHR}$-PTH(1-10) | ND | | |
| VHH$_{6E}$_PTH(1-14) | 0.4 ± 0.2 | 1.08 ± 0.23 | 3 |
| VHH$_{6E}$_PTH(1-11) | 6.9 ± 2.6 | 1.11 ± 0.18 | 3 |
| VHH$_{6E}$_PTH(1-10) | 2.8 ± 1.4 | 0.94 ± 0.04 | 3 |
| VHH$_{6E}$_PTH(1-9) | Inactive at 100 nM | | 3 |
| VHH$_{GFP}$_PTH(1-14) | Inactive at 100 nM | | 2 |
| VHH$_{GFP}$_PTH(1-11) | Inactive at 100 nM | | 2 |
| VHH$_{GFP}$_PTH(1-10) | ND | | |
| VHH$_{GFP}$_PTH(1-9) | ND | | |

| hPTHR1$_{YFP\Delta ECD}$ | EC$_{50}$ (nM ± SD) | Max (normalized ± SD) | n |
|---|---|---|---|
| PTH(1-34) | 689 ± 301 | 1.00 ± 0.00 | 7 |
| PTH(1-14) | 1.1 ± 0.9 | 0.96 ± 0.04 | 4 |
| PTH(1-11) | 246 ± 133 | 1.02 ± 0.12 | 10 |
| PTH(1-10) | 3841 ± 1604 | 1.12 ± 0.08 | 6 |
| PTH(1-9) | Inactive at 10,000 nM | | 3 |
| VHH$_{PTHR}$-PTH(1-14) | 0.9 ± 0.5 | 0.91 ± 0.15 | 4 |
| VHH$_{PTHR}$-PTH(1-11) | Inactive at 100 nM | | 3 |
| VHH$_{PTHR}$-PTH(1-10) | ND | | |
| VHH$_{6E}$_PTH(1-14) | 72 ± 15.2 | 1.11 ± 0.07 | 3 |
| VHH$_{6E}$_PTH(1-11) | Inactive at 100 nM | | 3 |
| VHH$_{6E}$_PTH(1-10) | ND | | |
| VHH$_{6E}$_PTH(1-9) | ND | | |
| VHH$_{GFP}$_PTH(1-14) | 0.58 ± 0.29 | 1.16 ± 0.36 | 4 |
| VHH$_{GFP}$_PTH(1-11) | 0.14 ± 0.06 | 1.19 ± 0.40 | 7 |
| VHH$_{GFP}$_PTH(1-10) | 0.46 ± 0.22 | 1.06 ± 0.35 | 7 |
| VHH$_{GFP}$_PTH(1-9) | ~40% activation at 100 nM | 0.38 ± 0.11 | 5 |

TABLE 5-continued

| rPTHR1 | EC$_{50}$ (nM ± SD) | Max (normalized ± SD) | n |
|---|---|---|---|
| PTH(1-34) | 0.28 ± 0.12 | 1.00 ± 0.00 | 3 |
| PTH(1-14) | | | |
| PTH(1-11) | 120.3 ± 90.3 | 1.02 ± 0.03 | 3 |
| PTH(1-10) | 2466 ± 23 | 1.09 ± 0.11 | 3 |
| PTH(1-9) | | | |
| VHH$_{PTHR}$-PTH(1-14) | | | |
| VHH$_{PTHR}$-PTH(1-11) | 3.2 ± 0.9 | 1.00 ± 0.13 | 3 |
| VHH$_{PTHR}$-PTH(1-10) | | | |
| VHH$_{6E}$-PTH(1-14) | | | |
| VHH$_{6E}$-PTH(1-11) | Inactive at 100 nM | | 2 |
| VHH$_{6E}$-PTH(1-10) | | | |
| VHH$_{6E}$-PTH(1-9) | | | |
| VHH$_{GFP}$-PTH(1-14) | | | |
| VHH$_{GFP}$-PTH(1-11) | Inactive at 100 nM | | 2 |
| VHH$_{GFP}$-PTH(1-10) | | | |
| VHH$_{GFP}$-PTH(1-9) | | | |

| hPTHR2 | EC$_{50}$ (nM ± SD) | Max (normalized ± SD) | n |
|---|---|---|---|
| PTH(1-34) | 1.45 ± 2.42 | 1 ± 0 | 4 |
| PTH(1-14) | 924 ± 328 | 1.14 ± 0.28 | 3 |
| PTH(1-11) | >100,000 (20% at 100 uM) | 0.36 ± 0.32 | 3 |
| PTH(1-10) | | | |
| PTH(1-9) | | | |
| VHH$_{PTHR}$-PTH(1-14) | Inactive at 330 nM | | 4 |
| VHH$_{PTHR}$-PTH(1-11) | | | |
| VHH$_{PTHR}$-PTH(1-10) | | | |
| VHH$_{6E}$-PTH(1-14) | Inactive at 330 nM | | 3 |
| VHH$_{6E}$-PTH(1-11) | | | |
| VHH$_{6E}$-PTH(1-10) | | | |
| VHH$_{6E}$-PTH(1-9) | | | |
| VHH$_{GFP}$-PTH(1-14) | | | |
| VHH$_{GFP}$-PTH(1-11) | | | |
| VHH$_{GFP}$-PTH(1-10) | | | |
| VHH$_{GFP}$-PTH(1-9) | | | |

REFERENCES

1. Carter, P. J.; Lazar, G. A., Next generation antibody drugs: pursuit of the 'high-hanging fruit'. *Nature Reviews Drug Discovery* 2018, 17 (3), 197-223.
2. Thomas, A.; Teicher, B. A.; Hassan, R. T., Antibody-drug conjugates for cancer therapy. *Lancet Oncology* 2016, 17 (6), E254-E262.
3. Hauser, A. S.; Attwood, M. M.; Rask-Andersen, M.; Schioth, H. B.; Gloriam, D. E., Trends in GPCR drug discovery: new agents, targets and indications. *Nature Reviews Drug Discovery* 2017, 16 (12), 829-842.
4. Hutchings, C. J.; Koglin. M.; Olson. W. C.; Marshall. F. H., Opportunities for therapeutic antibodies directed at G-protein-coupled receptors. *Nature Reviews Drug Discovery* 2017, 16 (11), 787-+.
5. Heukers, R.; De Groof, T. W. M.; Smit, M. J., Nanobodies detecting and modulating GPCRs outside in and inside out. *Current Opinion in Cell Biology* 2019, 57, 115-122.
6. Scholten, D. J.; Canals, M.; Maussang, D.; Roumen, L.; Smit, M. J.; Wijtmans, M.; de Graaf, C.; Vischer, H. F.; Leurs, R., Pharmacological modulation of chemokine receptor function. *British Journal of Pharmacology* 2012, 165 (6), 1617-1643.
7. Bortolato, A.; Dore, A. S.; Hollenstein, K.; Tehan, B. G.; Mason, J. S.; Marshall, F. H., Structure of Class B GPCRs: new horizons for drug discovery. *British Journal of Pharmacology* 2014, 171 (13), 3132-3145.
8. Gardella, T. J.; Vilardaga, J.-P., International Union of Basic and Clinical Pharmacology. XCIII. The Parathyroid Hormone Receptors-Family B G Protein-Coupled Receptors. *Pharmacological Reviews* 2015, 67 (2), 310-337.
9. de Graaf, C.; Song, G. J.; Cao, C.; Zhao, Q.; Wang, M. W.; Wu, B. L.; Stevens, R. C., Extending the Structural View of Class B GPCRs. *Trends in Biochemical Sciences* 2017, 42 (12), 946-960.
10. Ingram, J. R.; Schmidt, F. I.; Ploegh, H. L., Exploiting Nanobodies' Singular Traits. *Annual Review of Immunology*, Vol 36 2018, 36, 695-715.
11. Koehl, A.; Hu, H. L.; Feng, D.; Sun, B. F.; Zhang, Y.; Robertson, M. J.; Chu, M.; Kobilka, T. S.; Laermans, T.; Steyaert, J.; Tarrasch, J.; Dutta, S.; Fonseca, R.; Weis, W. I.; Mathiesen, J. M.; Skiniotis, G.; Kobilka, B. K., Structural insights into the activation of metabotropic glutamate receptors. *Nature* 2019, 566 (7742), 79-+.
12. Konning, D.; Zielonka, S.; Grzeschik, J.; Empting, M.; Valldorfl, B.; Krah, S.; Schroter, C.; Sellmann, C.; Hock, B.; Kolmarl, H., Camelid and shark single domain antibodies: structural features and therapeutic potential. *Current Opinion in Structural Biology* 2017, 45, 10-16.
13. Ehrenmann, J.; Schoppe, J.; Klenk, C.; Rappas, M.; Kummer, L.; Dore, A. S.; Pluckthun, A., High-resolution crystal structure of parathyroid hormone 1 receptor in complex with a peptide agonist. *Nature Structural & Molecular Biology* 2018, 25 (12), 1086-+.
14. Zhao, L. H.; Ma, S. S.; Sutkeviciute, I.; Shen, D. D.; Zhou, X. E.; de Waal, P. W.; Li, C. Y.; Kang, Y. Y.; Clark, L. J.; Jean-Alphonse, F. G.; White, A. D.; Yang, D. H.; Dai, A. T.; Cai, X. Q.; Chen, J.; Li, C.; Jiang, Y.; Watanabe, T.; Gardella, T. J.; Melcher, K.; Wang, M. W.; Vilardaga, J. P.; Xu, H. E.; Zhang, Y., Structure and dynamics of the active human parathyroid hormone receptor-1. *Science* 2019, 364 (6436), 148-+.
15. Guimaraes, C. P.; Witte, M. D.; Theile, C. S.; Bozkurt, G.; Kundrat, L.; Blom, A. E.; Ploegh, H. L., Site-specific C-terminal and internal loop labeling of proteins using sortase-mediated reactions. In *Nat Protoc*, England, 2013; Vol. 8, pp 1787-99.
16. Cheloha, R. W.; Gellman, S. H.; Vilardaga, J.-P.; Gardella, T. J., PTH receptor-1 signalling [mdash]mechanistic insights and therapeutic prospects. *Nat Rev Endocrinol* 2015, 11, 712-724.
17. Pioszak, A. A.; Xu, H. E., Molecular recognition of parathyroid hormone by its G protein-coupled receptor. *Proceedings of the National Academy of Sciences of the United States of America* 2008, 105 (13), 5034-5039.
18. Lee, C. W.; Gardella, T. J.; Abousamra, A. B.; Nussbaum, S. R.; Segre, G. V.; Potts, J. T.; Kronenberg, H. M.; Juppner, H., ROLE OF THE EXTRACELLULAR REGIONS OF THE PARATHYROID-HORMONE (PTH) PTH-RELATED PEPTIDE RECEPTOR IN HORMONE-BINDING. *Endocrinology* 1994, 135 (4), 1488-1495.
19. Mahon, M. J., pHluorin2: an enhanced, ratiometric, pH-sensitive green florescent protein. *Adv Biosci Biotechnol* 2011, 2 (3), 132-137.
20. Ling, J.; Cheloha, R. W.; McCaul, N.; Sun, Z.-Y. J.; Wagner, G.; Ploegh, H. L. A nanobody that recognizes a 14-residue peptide epitope in the E2 ubiquitin-conjugating enzyme UBC6e modulates its activity *Molecular Immunology* [Online], 2019.
21. Carter, P. H.; Dean, T.; Bhayana, B.; Khatri, A.; Rajur, R.; Gardella, T. J., Actions of the Small Molecule Ligands SW106 and AH-3960 on the Type-1 Parathyroid Hormone Receptor. *Molecular Endocrinology* 2015, 29 (2), 307-321.
22. Kirchhofer, A.; Helma, J.; Schmidthals, K.; Frauer, C.; Cui, S.; Karcher, A.; Pellis, M.; Muyldermans, S.; Casas-Delucchi, C. S.; Cardoso, M. C.; Leonhardt, H.; Hopfner, K. P.; Rothbauer, U., Modulation of protein properties in living cells using nanobodies. *Nature Structural & Molecular Biology* 2010, 17 (1), 133-U162.
23. Adams, H.; Saunders, M. J. S.; De Haard, J. J. W. AMINO ACID SEQUENCES DIRECTED AGAINST GPCRS AND POLYPEPTIDES COMPRISING THE SAME FOR THE TREATMENT OF GPCR-RELATED DISEASES AND DISORDERS. 2010.
24. Rashidian, M.; Keliher, E. J.; Bilate, A. M.; Duarte, J. N.; Wojtkiewicz, G. R.; Jacobsen, J. T.; Cragnolini, J.; Swee, L. K.; Victora, G. D.; Weissleder, R.; Ploegh, H. L., Noninvasive imaging of immune responses. *Proceedings of the National Academy of Sciences of the United States of America* 2015, 112 (19), 6146-6151.
25. Duarte, J. N.; Cragnolini, J. J.; Swee, L. K.; Bilate, A. M.; Bader, J.; Ingram, J. R.; Rashidfarrokhi, A.; Fang, T.; Schiepers, A.; Hanke, L.; Ploegh, H. L., Generation of Immunity against Pathogens via Single-Domain Antibody-Antigen Constructs. *Journal of Immunology* 2016, 197 (12), 4838-4847.
26. Okazaki, M.; Ferrandon, S.; Vilardaga, J. P.; Bouxsein, M. L.; Potts, J. T.; Gardella, T. J., Prolonged signaling at the parathyroid hormone receptor by peptide ligands targeted to a specific receptor conformation. *Proceedings of the National Academy of Sciences of the United States of America* 2008, 105 (43), 16525-16530.
27. Cheloha, R. W.; Maeda, A.; Dean, T.; Gardella, T. J.; Gellman, S. H., Backbone modification of a polypeptide drug alters duration of action in vivo. *Nature Biotechnology* 2014, 32 (7), 653-655.
28. Liu, S.; Cheloha, R. W.; Watanabe, T.; Gardella, T. J.; Gellman, S. H., Receptor selectivity from minimal backbone modification of a polypeptide agonist. *Proceedings of the National Academy of Sciences of the United States of America* 2018, 115 (49), 12383-12388.
29. Ferrandon, S.; Feinstein, T. N.; Castro, M.; Wang, B.; Bouley, R.; Potts, J. T.; Gardella, T. J.; Vilardaga, J.-P., Sustained cyclic AMP production by parathyroid hormone receptor endocytosis. *Nature Chemical Biology* 2009, 5 (10), 734-742.
30. Binkowski, B. F.; Butler, B. L.; Stecha, P. F.; Eggers, C. T.; Otto, P.; Zimmerman, K.; Vidugiris, G.; Wood, M. G.; Encell, L. P.; Fan, F.; Wood, K. V., A Luminescent Biosensor with Increased Dynamic Range for Intracellular cAMP. *Acs Chemical Biology* 2011, 6 (11), 1193-1197.
31. Rabbani, S. A.; Yasuda, T.; Bennett, H. P. J.; Sung, W. L.; Zahab, D. M.; Tam, C. S.; Goltzman, D.; Hendy, G. N., RECOMBINANT HUMAN PARATHYROID-HORMONE SYNTHESIZED IN *ESCHERICHIA-COLI*—PURIFICATION AND CHARACTERIZATION. *Journal of Biological Chemistry* 1988, 263 (3), 1307-1313.
32. Cheloha, R. W.; Chen, B. M.; Kumar, N. N.; Watanabe, T.; Thorne, R. G.; Li, L. J.; Gardella, T. J.; Gellman, S. H., Development of Potent, Protease-Resistant Agonists of the Parathyroid Hormone Receptor with Broad beta Residue Distribution. *Journal of Medicinal Chemistry* 2017, 60 (21), 8816-8833.
33. Pleiner, T.; Bates, M.; Görlich, D., A toolbox of anti-mouse and anti-rabbit IgG secondary nanobodies. *The Journal of Cell Biology* 2017.
34. Wootten, D.; Christopoulos, A.; Marti-Solano, M.; Babu, M. M.; Sexton, P. M., Mechanisms of signalling and biased agonism in G protein-coupled receptors. *Nature Reviews Molecular Cell Biology* 2018, 19 (10), 638-653.
35. Cupp, M. E.; Nayak, S. K.; Adem, A. S.; Thomsen, W. J., Parathyroid hormone (PTH) and PTH-related peptide domains contributing to activation of different PTH receptor-mediated signaling pathways. *J Pharmacol Exp Ther* 2013, 345 (3), 404-18.
36. Neri, D., Antibody-Cytokine Fusions: Versatile Products for the Modulation of Anticancer Immunity. Cancer Immunology Research 2019, 7 (3), 348-354.
37. Tzeng, A.; Kwan, B. H.; Opel, C. F.; Navaratna, T.; Wittrup, K. D., Antigen specificity can be irrelevant to immunocytokine efficacy and biodistribution. *Proceedings of the National Academy of Sciences of the United States of America* 2015, 112 (11), 3320-3325.
38. Garcin, G.; Paul, F.; Staufenbiel, M.; Bordat, Y.; Van der Heyden, J.; Wilmes, S.; Cartron, G.; Apparailly, F.; De Koker, S.; Piehler, J.; Tavernier, J.; Uze, G., High efficiency cell-specific targeting of cytokine activity. *Nature Communications* 2014, 5.
39. Pogue, S. L.; Taura, T.; Bi, M. Y.; Yun, Y.; Sho, A.; Mikesell, G.; Behrens, C.; Sokolovsky, M.; Hallak, H.; Rosenstock, M.; Sanchez, E.; Chen, H. M.; Berenson, J.; Doyle, A.; Nock, S.; Wilson, D. S., Targeting Attenuated Interferon-alpha to Myeloma Cells with a CD38 Antibody Induces Potent Tumor Regression with Reduced Off-Target Activity. *Plos One* 2016, 11 (9).
40. Farrants, H.; Gutzeit, V. A.; Acosta-Ruiz, A.; Trauner, D.; Johnsson, K.; Levitz, J.; Broichhagen, J., SNAP-Tagged Nanobodies Enable Reversible Optical Control of a G Protein-Coupled Receptor via a Remotely Tethered Photoswitchable Ligand. *Acs Chemical Biology* 2018, 13 (9), 2682-2688.
41. Chodorge, M.; Celeste, A. J.; Grimsby, J.; Konkar, A.; Davidsson, P.; Fairman, D.; Jenkinson, L.; Naylor, J.; White, N.; Seaman, J. C.; Dickson, K.; Kemp, B.; Spooner, J.; Rossy, E.; Hornigold, D. C.; Trevaskis, J. L.; Bond, N. J.; London, T. B.; Buchanan, A.; Vaughan, T.;

Rondinone, C. M.; Osbourn, J. K., Engineering of a GLP-1 analogue peptide/anti-PCSK9 antibody fusion for type 2 diabetes treatment. *Scientific Reports* 2018, 8.
42. Shimizu, M.; Carter, P. H.; Gardella, T. J., Autoactivation of type-1 parathyroid hormone receptors containing a tethered ligand. *Journal of Biological Chemistry* 2000, 275 (26), 19456-19460.
43. Devigny, C.; Perez-Balderas, F.; Hoogeland, B.; Cuboni, S.; Wachtel, R.; Mauch, C. P.; Webb, K. J.; Deussing, J. M.; Hausch, F., Biomimetic Screening of Class-B G Protein-Coupled Receptors. *Journal of the American Chemical Society* 2011, 133 (23), 8927-8933.
44. Urban, D. J.; Roth, B. L., DREADDs (Designer Receptors Exclusively Activated by Designer Drugs): Chemogenetic Tools with Therapeutic Utility. *Annual Review of Pharmacology and Toxicology*, Vol 55 2015, 55, 399-417.
45. Armbruster, B. N.; Li, X.; Pausch, M. H.; Herlitze, S.; Roth, B. L., Evolving the lock to fit the key to create a family of G protein-coupled receptors potently activated by an inert ligand. *Proceedings of the National Academy of Sciences of the United States of America* 2007, 104 (12), 5163-5168.
46. Guettier, J. M.; Gautam, D.; Scarselli, M.; de Azua, I. R.; Li, J. H.; Rosemond, E.; Ma, X. C.; Gonzalez, F. J.; Armbruster, B. N.; Lu, H. Y.; Roth, B. L.; Wess, J., A chemical-genetic approach to study G protein regulation of beta cell function in vivo. *Proceedings of the National Academy of Sciences of the United States of America* 2009, 106 (45), 19197-19202.
47. Sockolosky, J. T.; Trotta, E.; Parisi, G.; Picton, L.; Su, L. L.; Le, A. C.; Chhabra, A.; Silveria, S. L.; George, B. M.; King, I. C.; Tiffany, M. R.; Jude, K.; Sibener, L. V.; Baker, D.; Shizuru, J. A.; Ribas, A.; Bluestone, J. A.; Garcia, K. C., Selective targeting of engineered T cells using orthogonal IL-2 cytokine-receptor complexes. *Science* 2018, 359 (6379), 1037-+.
48. Alvarez-Curto, E.; Milligan, G., Defining the Functional Equivalence of Wild-Type and Chemically Engineered G Protein-Coupled Receptors. *Designer Receptors Exclusively Activated by Designer Drugs* 2015, 108, 1-28.
49. Maeda, A.; Okazaki, M.; Baron, D. M.; Dean, T.; Khatri, A.; Mahon, M.; Segawa, H.; Abou-Samra, A. B.; Jueppner, H.; Bloch, K. D.; Potts, J. T., Jr.; Gardella, T. J., Critical role of parathyroid hormone (PTH) receptor-1 phosphorylation in regulating acute responses to PTH. *Proceedings of the National Academy of Sciences of the United States of America* 2013, 110 (15), 5864-5869.
50. Herenbrink, C. K.; Sykes, D. A.; Donthamsetti, P.; Canals, M.; Coudrat, T.; Shonberg, J.; Scammells, P. J.; Capuano, B.; Sexton, P. M.; Charlton, S. J.; Javitch, J. A.; Christopoulos, A.; Lane, J. R., The role of kinetic context in apparent biased agonism at GPCRs. *Nature Communications* 2016, 7.
51. Wehbi, V. L.; Stevenson, H. P.; Feinstein, T. N.; Calero, G.; Romero, G.; Vilardaga, J.-P., Noncanonical GPCR signaling arising from a PTH receptor-arrestin-G beta gamma complex. *Proceedings of the National Academy of Sciences of the United States of America* 2013, 110 (4), 1530-1535.

REFERENCES

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. An engineered ligand that binds to a human parathyroid hormone receptor 1 (PTHR1), the engineered ligand comprising a sub-optimal ligand conjugated to an antibody that binds to PTHR1;
   wherein the sub-optimal ligand comprises an N-terminal fragment of parathyroid hormone (PTH) comprising amino acids 1-9 of PTH (SEQ ID NO: 3) and not comprising amino acids 15-34 of PTH (SEQ ID NO: 3);
   wherein the antibody is a nanobody;
   wherein the sub-optimal ligand comprises a C-terminus and an N-terminus;
   wherein the antibody comprises a C-terminus and an N-terminus; and
   wherein the C-terminus of the sub-optimal ligand is conjugated to the C-terminus or the N-terminus of the antibody and wherein the antibody binds to an epitope consisting of the amino acid sequence of any one of SEQ ID NO: 53-55.

2. The engineered ligand of claim 1, wherein the sub-optimal ligand binds a first binding site of PTHR1 and the PTHR1 antibody binds a second binding site of PTHR1.

3. The engineered ligand of claim 1, wherein the suboptimal ligand comprises an unnatural amino acid.

4. The engineered ligand of claim 1, wherein the PTHR1 is a natural or an engineered PTHR1.

5. A complex comprising the engineered ligand of claim 1 associated with the PTHR1.

6. A composition comprising the engineered ligand of claim 1 and a pharmaceutically acceptable carrier.

7. The engineered ligand of claim 1, wherein the sub-optimal ligand is selected from the group consisting of any one of SEQ ID NOs: 5-51 and 85-91.

8. The engineered ligand of claim 1, wherein the C-terminus of the sub-optimal ligand is conjugated to the C-terminus of the antibody.

9. The engineered ligand of claim 1, wherein the antibody comprises the amino acid sequence of any one of SEQ ID NOs: 71, 74, and 80.

10. The engineered ligand of claim 1, wherein the antibody comprises a peptide linker at its C-terminus.

11. The engineered ligand of claim 10, wherein the peptide linker comprises the amino acid sequence of GGL-PETGG (SEQ ID NO: 81).

12. The engineered ligand of claim 1, wherein the sub-optimal ligand is conjugated to the antibody via a linker.

13. The engineered ligand of claim 12, wherein linker is a polyethylene (PEG) linker.

14. The engineered ligand of claim 3, wherein the unnatural amino acid is aminoisobutyric acid (Aib), homoarginine (Homoarg), or 1-aminocyclopentane-1-carboxylic acid (ACPC).

* * * * *

UNITED STATES PATENT AND TRADEMARK OFFICE
CERTIFICATE OF CORRECTION

| | |
|---|---|
| PATENT NO. | : 11,878,063 B2 |
| APPLICATION NO. | : 16/810783 |
| DATED | : January 23, 2024 |
| INVENTOR(S) | : Ross Cheloha et al. |

It is certified that error appears in the above-identified patent and that said Letters Patent is hereby corrected as shown below:

In the Specification

At Column 1, Line 12, please replace the paragraph titled "GOVERNMENT SUPPORT" with the following paragraph:
FEDERALLY SPONSORED RESEARCH
This invention was made with government support under Grant Numbers AI087879, and DK011794, awarded by the National Institutes of Health. The Government has certain rights in the invention.

Signed and Sealed this
Nineteenth Day of March, 2024

Katherine Kelly Vidal
*Director of the United States Patent and Trademark Office*

SEQUENCE LISTING

```
<160> NUMBER OF SEQ ID NOS: 97

<210> SEQ ID NO 1
<211> LENGTH: 115
<212> TYPE: PRT
<213> ORGANISM: Homo sapiens

<400> SEQUENCE: 1

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
        50                  55                  60

Phe Val Ala Leu Gly Ala Pro Leu Ala Pro Arg Asp Ala Gly Ser Gln
65                  70                  75                  80

Arg Pro Arg Lys Lys Glu Asp Asn Val Leu Val Glu Ser His Glu Lys
                85                  90                  95

Ser Leu Gly Glu Ala Asp Lys Ala Asp Val Asn Val Leu Thr Lys Ala
            100                 105                 110

Lys Ser Gln
        115

<210> SEQ ID NO 2
<211> LENGTH: 84
<212> TYPE: PRT
<213> ORGANISM: Homo sapiens

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr Lys
65                  70                  75                  80

Ala Lys Ser Gln
```

```
<210> SEQ ID NO 3
<211> LENGTH: 34
<212> TYPE: PRT
<213> ORGANISM: Homo sapiens

<400> SEQUENCE: 3

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 4
<211> LENGTH: 35
<212> TYPE: PRT
<213> ORGANISM: Homo sapiens

<400> SEQUENCE: 4

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Cys
        35

<210> SEQ ID NO 5
<211> LENGTH: 14
<212> TYPE: PRT
<213> ORGANISM: Artificial Sequence
<220> FEATURE:
<223> OTHER INFORMATION: Synthetic

<400> SEQUENCE: 5

Ser Val Ser Glu Ile Gln Leu Met His Asn Leu Gly Lys His
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Ser Val Ser Glu Ile Gln Leu Met His Asn Leu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Ser Val Ser Glu Ile Gln Leu Met His Asn
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 8

Ser Val Ser Glu Ile Gln Leu Met His
1               5

<210> SEQ ID NO 9
<211> LENGTH: 14
<212> TYPE: PRT
<213> ORGANISM: Artificial Sequence
<220> FEATURE:
<223> OTHER INFORMATION: Synthetic

<400> SEQUENCE: 9

Ala Val Ser Glu Ile Gln Leu Met His Gln Ala Lys Trp Cys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic

<400> SEQUENCE: 10

Ala Val Ser Glu Ile Gln Leu Met His Gln Arg
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic

<400> SEQUENCE: 11

Ala Val Ser Glu Ile Gln Leu Met His Gln
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 12

Ser Val Ala Glu Ile Gln Leu Met His Asn Leu Gly Lys His
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 13

Ser Val Ala Glu Ile Gln Leu Met His Asn Leu
1               5                   10
```

```
<210> SEQ ID NO 14
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 14

Ser Val Ala Glu Ile Gln Leu Met His Asn
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 15

Ser Val Ala Glu Ile Gln Leu Met His
1               5

<210> SEQ ID NO 16
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 16

Ala Val Ala Glu Ile Gln Leu Met His Gln Ala Lys Trp Cys
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 17

Ala Val Ala Glu Ile Gln Leu Met His Gln Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid
```

```
<400> SEQUENCE: 18

Ala Val Ala Glu Ile Gln Leu Met His Gln
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid

<400> SEQUENCE: 19

Ala Val Ser Glu Ile Gln Leu Met His Asn Leu Gly Lys His
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid

<400> SEQUENCE: 20

Ala Val Ser Glu Ile Gln Leu Met His Asn Leu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid

<400> SEQUENCE: 21

Ala Val Ser Glu Ile Gln Leu Met His Asn
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid

<400> SEQUENCE: 22

Ala Val Ser Glu Ile Gln Leu Met His
1               5

<210> SEQ ID NO 23
<211> LENGTH: 14
<212> TYPE: PRT
<213> ORGANISM: Artificial Sequence
```

```
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid

<400> SEQUENCE: 23

Ala Val Ser Glu Ile Gln Leu Met His Gln Ala Lys Trp Cys
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid

<400> SEQUENCE: 24

Ala Val Ser Glu Ile Gln Leu Met His Gln Arg
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid

<400> SEQUENCE: 25

Ala Val Ser Glu Ile Gln Leu Met His Gln
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Ser Val Ser Glu Ile Gln Ala Met His Asn Leu Gly Lys His
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (7)..(7)
<223> OTHER INFORMATION: Ala is 2-aminoisobutyric acid

<400> SEQUENCE: 27

Ser Val Ser Glu Ile Gln Ala Met His Asn Leu
1               5                   10
```

```
<210> SEQ ID NO 28
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (7)..(7)
<223> OTHER INFORMATION: Ala is 2-aminoisobutyric acid

<400> SEQUENCE: 28

Ser Val Ser Glu Ile Gln Ala Met His Asn
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (7)..(7)
<223> OTHER INFORMATION: Ala is 2-aminoisobutyric acid

<400> SEQUENCE: 29

Ser Val Ser Glu Ile Gln Ala Met His
1               5

<210> SEQ ID NO 30
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (7)..(7)
<223> OTHER INFORMATION: Ala is 2-aminoisobutyric acid

<400> SEQUENCE: 30

Ala Val Ser Glu Ile Gln Ala Met His Gln Ala Lys Trp Cys
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (7)..(7)
<223> OTHER INFORMATION: Ala is 2-aminoisobutyric acid

<400> SEQUENCE: 31

Ala Val Ser Glu Ile Gln Ala Met His Gln Arg
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (7)..(7)
<223> OTHER INFORMATION: Ala is 2-aminoisobutyric acid
```

```
<400> SEQUENCE: 32

Ala Val Ser Glu Ile Gln Ala Met His Gln
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: Ala is 2-aminoisobutyric acid

<400> SEQUENCE: 33

Ser Val Ser Glu Ile Gln Leu Met His Ala Leu Gly Lys His
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: Ala is 2-aminoisobutyric acid

<400> SEQUENCE: 34

Ser Val Ser Glu Ile Gln Leu Met His Ala Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: Ala is 2-aminoisobutyric acid

<400> SEQUENCE: 35

Ser Val Ser Glu Ile Gln Leu Met His Ala
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: Ala is 2-aminoisobutyric acid

<400> SEQUENCE: 36

Ala Val Ser Glu Ile Gln Leu Met His Ala Ala Lys Trp Cys
1               5                   10

<210> SEQ ID NO 37
<211> LENGTH: 11
<212> TYPE: PRT
<213> ORGANISM: Artificial Sequence
```

```
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: Ala is 2-aminoisobutyric acid

<400> SEQUENCE: 37

Ala Val Ser Glu Ile Gln Leu Met His Ala Arg
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: Ala is 2-aminoisobutyric acid

<400> SEQUENCE: 38

Ala Val Ser Glu Ile Gln Leu Met His Ala
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (12)..(12)
<223> OTHER INFORMATION: Ala is 2-aminoisobutyric acid

<400> SEQUENCE: 39

Ser Val Ser Glu Ile Gln Leu Met His Asn Leu Ala Lys His
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (12)..(12)
<223> OTHER INFORMATION: Ala is 2-aminoisobutyric acid

<400> SEQUENCE: 40

Ala Val Ser Glu Ile Gln Leu Met His Gln Ala Ala Trp Cys
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid
<220> FEATURE:
<221> NAME/KEY: MOD_RES
<222> LOCATION: (3)..(3)
<223> OTHER INFORMATION: Ala is 2-aminoisobutyric acid
```

<400> SEQUENCE: 41

Ala Val Ala Glu Ile Gln Leu Met His Asn Leu Gly Lys His
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 42

Ala Val Ala Glu Ile Gln Leu Met His Asn Leu
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 43

Ala Val Ala Glu Ile Gln Leu Met His Asn
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 44

Ala Val Ala Glu Ile Gln Leu Met His
1               5

<210> SEQ ID NO 45
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid

```
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 45

Ala Val Ala Glu Ile Gln Leu Met His Gln Ala Lys Trp Cys
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 46

Ala Val Ala Glu Ile Gln Leu Met His Gln Arg
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 47

Ala Val Ala Glu Ile Gln Leu Met His Gln
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Ala Val Ser Glu Ile Gln Cys Met His
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid
```

<400> SEQUENCE: 49

Ala Val Ala Glu Ile Gln Cys Met His
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid

<400> SEQUENCE: 50

Ala Val Ser Glu Ile Gln Cys Met His
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 51

Ala Val Ala Glu Ile Gln Cys Met His
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic

<400> SEQUENCE: 52

Ser Ala Lys Glu Leu Arg Cys
1               5

<210> SEQ ID NO 53
<211> LENGTH: 14
<212> TYPE: PRT
<213> ORGANISM: Artificial Sequence
<220> FEATURE:
<223> OTHER INFORMATION: Synthetic

<400> SEQUENCE: 53

Gln Ala Asp Gln Glu Ala Lys Glu Leu Ala Arg Gln Ile Ser
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic

```
<400> SEQUENCE: 54

Gln Ala Asp Glu Ala Lys Glu Leu Ala Arg Gln Ile
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic

<400> SEQUENCE: 55

Gln Ala Asp Glu Ala Lys Glu Leu Ala Arg Gln
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic

<400> SEQUENCE: 56

Pro Asp Arg Lys Ala Ala Val Ser His Trp Gln Gln
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic

<400> SEQUENCE: 57

Pro Asp Arg Val Arg Ala Val Ser His Trp Ser Ser
1               5                   10

<210> SEQ ID NO 58
<211> LENGTH: 240
<212> TYPE: PRT
<213> ORGANISM: Artificial Sequence
<220> FEATURE:
<223> OTHER INFORMATION: Synthetic

<400> SEQUENCE: 58

Thr Met Val Ser Lys Gly Glu Glu Leu Phe Thr Gly Val Val Pro Ile
1               5                   10                  15

Leu Val Glu Leu Asp Gly Asp Val Asn Gly His Lys Phe Ser Val Ser
                20                  25                  30

Gly Glu Gly Glu Gly Asp Ala Thr Tyr Gly Lys Leu Thr Leu Lys Leu
            35                  40                  45

Ile Cys Thr Thr Gly Lys Leu Pro Val Pro Trp Pro Thr Leu Val Thr
        50                  55                  60

Thr Leu Gly Tyr Gly Val Gln Cys Phe Ala Arg Tyr Pro Asp His Met
65                  70                  75                  80

Lys Gln His Asp Phe Phe Lys Ser Ala Met Pro Glu Gly Tyr Val Gln
                85                  90                  95

Glu Arg Thr Ile Phe Phe Lys Asp Asp Gly Asn Tyr Lys Thr Arg Ala
            100                 105                 110

Glu Val Lys Phe Glu Gly Asp Thr Leu Val Asn Arg Ile Glu Leu Lys
        115                 120                 125
```

```
Gly Ile Asp Phe Lys Glu Asp Gly Asn Ile Leu Gly His Lys Leu Glu
        130                 135                 140

Tyr Asn Tyr Asn Ser His Asn Val Tyr Ile Thr Ala Asp Lys Gln Lys
145                 150                 155                 160

Asn Gly Ile Lys Ala Asn Phe Lys Ile Arg His Asn Ile Glu Asp Gly
                165                 170                 175

Gly Val Gln Leu Ala Asp His Tyr Gln Gln Asn Thr Pro Ile Gly Asp
            180                 185                 190

Gly Pro Val Leu Leu Pro Asp Asn His Tyr Leu Ser Tyr Gln Ser Lys
        195                 200                 205

Leu Ser Lys Asp Pro Asn Glu Lys Arg Asp His Met Val Leu Leu Glu
    210                 215                 220

Phe Val Thr Ala Ala Gly Ile Thr Leu Gly Met Asp Glu Leu Tyr Lys
225                 230                 235                 240

<210> SEQ ID NO 59
<211> LENGTH: 14
<212> TYPE: PRT
<213> ORGANISM: Artificial Sequence
<220> FEATURE:
<223> OTHER INFORMATION: Synthetic

<400> SEQUENCE: 59

Gln Ala Asp Gln Glu Ala Lys Glu Leu Ala Arg Gln Ile Ser
1               5                   10

<210> SEQ ID NO 60
<211> LENGTH: 26
<212> TYPE: PRT
<213> ORGANISM: Artificial Sequence
<220> FEATURE:
<223> OTHER INFORMATION: Synthetic

<400> SEQUENCE: 60

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 61
<211> LENGTH: 7
<212> TYPE: PRT
<213> ORGANISM: Artificial Sequence
<220> FEATURE:
<223> OTHER INFORMATION: Synthetic

<400> SEQUENCE: 61

Asp Tyr Lys Asp Asp Asp Asp
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic

<400> SEQUENCE: 62

Asp Tyr Lys Asp Asp Asp Asp Lys
1               5
```

```
<210> SEQ ID NO 63
<211> LENGTH: 7
<212> TYPE: PRT
<213> ORGANISM: Artificial Sequence
<220> FEATURE:
<223> OTHER INFORMATION: Synthetic

<400> SEQUENCE: 63

Asp Tyr Lys Asp Asp Asp Lys
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Tyr Pro Tyr Asp Val Pro Asp Tyr Ala
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Tyr Ala Tyr Asp Val Pro Asp Tyr Ala
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic

<400> SEQUENCE: 66

Tyr Asp Val Pro Asp Tyr Ala Ser Leu
1               5

<210> SEQ ID NO 67
<211> LENGTH: 10
<212> TYPE: PRT
<213> ORGANISM: Artificial Sequence
<220> FEATURE:
<223> OTHER INFORMATION: Synthetic

<400> SEQUENCE: 67

Glu Gln Lys Leu Ile Ser Glu Glu Asp Leu
1               5                   10

<210> SEQ ID NO 68
<211> LENGTH: 6
<212> TYPE: PRT
<213> ORGANISM: Artificial Sequence
<220> FEATURE:
<223> OTHER INFORMATION: Synthetic

<400> SEQUENCE: 68

His His His His His His
1               5
```

<210> SEQ ID NO 69
<211> LENGTH: 15
<212> TYPE: PRT
<213> ORGANISM: Artificial Sequence
<220> FEATURE:
<223> OTHER INFORMATION: Synthetic

<400> SEQUENCE: 69

```
Lys Glu Thr Ala Ala Ala Lys Phe Glu Arg Gln His Met Asp Ser
1               5                   10                  15
```

<210> SEQ ID NO 70
<211> LENGTH: 14
<212> TYPE: PRT
<213> ORGANISM: Artificial Sequence
<220> FEATURE:
<223> OTHER INFORMATION: Synthetic

<400> SEQUENCE: 70

```
Gly Lys Pro Ile Pro Asn Pro Leu Leu Gly Leu Asp Ser Thr
1               5                   10
```

<210> SEQ ID NO 71
<211> LENGTH: 111
<212> TYPE: PRT
<213> ORGANISM: Artificial Sequence
<220> FEATURE:
<223> OTHER INFORMATION: Synthetic

<400> SEQUENCE: 71

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Val Phe Glu Asn Ser
            20                  25                  30

Ala Met Ala Trp Tyr Arg Gln Ala Pro Gly Lys Glu Arg Glu Leu Ile
        35                  40                  45

Ala Val Ile Gly Thr Thr Phe Ile Lys Leu Ala Glu Ser Val Lys Gly
    50                  55                  60

Arg Phe Thr Ile Ser Arg Asp Asn Ala Lys Ser Thr Val Tyr Leu Gln
65                  70                  75                  80

Met Asn Asn Leu Lys Pro Glu Asp Thr Ala Val Tyr Tyr Cys Ser Lys
                85                  90                  95

Ser Gly Ala Tyr Trp Gly Gln Gly Thr Gln Val Thr Val Ser Ser
            100                 105                 110
```

<210> SEQ ID NO 72
<211> LENGTH: 122
<212> TYPE: PRT
<213> ORGANISM: Artificial Sequence
<220> FEATURE:
<223> OTHER INFORMATION: Synthetic

<400> SEQUENCE: 72

```
Gln Val Gln Leu Val Glu Ser Gly Gly Gly Leu Val Gln Pro Gly Gly
1               5                   10                  15

Ser Leu Thr Leu Ser Cys Thr Ala Ser Gly Phe Thr Leu Asp His Tyr
            20                  25                  30

Asp Ile Gly Trp Phe Arg Gln Ala Pro Gly Lys Glu Arg Glu Gly Val
        35                  40                  45

Ser Cys Ile Asn Asn Ser Asp Asp Thr Tyr Tyr Ala Asp Ser Val
    50                  55                  60
```

-continued

Lys Gly Arg Phe Thr Ile Phe Met Asn Asn Ala Lys Asp Thr Val Tyr
 65                  70                  75                  80

Leu Gln Met Asn Ser Leu Lys Pro Glu Asp Thr Ala Ile Tyr Tyr Cys
                 85                  90                  95

Ala Glu Ala Arg Gly Cys Lys Arg Gly Arg Tyr Glu Tyr Asp Phe Trp
            100                 105                 110

Gly Gln Gly Thr Gln Val Thr Val Ser Ser
        115                 120

<210> SEQ ID NO 73
<211> LENGTH: 115
<212> TYPE: PRT
<213> ORGANISM: Artificial Sequence
<220> FEATURE:
<223> OTHER INFORMATION: Synthetic

<400> SEQUENCE: 73

Gln Val Gln Leu Gln Glu Ser Gly Gly Ala Leu Val Gln Pro Gly Gly
 1               5                  10                  15

Ser Leu Arg Leu Ser Cys Ala Ala Ser Gly Phe Pro Val Asn Arg Tyr
             20                  25                  30

Ser Met Arg Trp Tyr Arg Gln Ala Pro Gly Lys Glu Arg Glu Trp Val
         35                  40                  45

Ala Gly Met Ser Ser Ala Gly Asp Arg Ser Ser Tyr Glu Asp Ser Val
     50                  55                  60

Lys Gly Arg Phe Thr Ile Ser Arg Asp Asp Ala Arg Asn Thr Val Tyr
 65                  70                  75                  80

Leu Gln Met Asn Ser Leu Lys Pro Glu Asp Thr Ala Val Tyr Tyr Cys
                 85                  90                  95

Asn Val Asn Val Gly Phe Glu Tyr Trp Gly Gln Gly Thr Gln Val Thr
            100                 105                 110

Val Ser Ser
        115

<210> SEQ ID NO 74
<211> LENGTH: 119
<212> TYPE: PRT
<213> ORGANISM: Artificial Sequence
<220> FEATURE:
<223> OTHER INFORMATION: Synthetic

<400> SEQUENCE: 74

Glu Val Gln Leu Val Glu Ser Gly Gly Gly Leu Val Gln Ala Gly Gly
 1               5                  10                  15

Ser Leu Arg Leu Ser Cys Ala Ala Ser Gly Asn Ile Phe Ala Asn Asn
             20                  25                  30

Ile Met Gly Trp Tyr Arg Gln Pro Pro Gly Lys Glu Arg Glu Phe Val
         35                  40                  45

Ala His Val Ser His Asp Gly Asp Ser Met Tyr Ala Val Ser Val Lys
     50                  55                  60

Gly Arg Phe Ala Ile Ser Arg Lys Asp Ala Thr Asn Leu Tyr Leu Gln
 65                  70                  75                  80

Met Asn Ser Leu Lys Pro Glu Asp Thr Ala Ile Tyr Phe Cys Arg Leu
                 85                  90                  95

Leu Asn Ile Pro Thr Gln Gly Arg Met Glu Gly Phe Trp Gly Gln Gly
            100                 105                 110

Thr Gln Val Thr Val Ser Ser
        115

```
<210> SEQ ID NO 75
<211> LENGTH: 118
<212> TYPE: PRT
<213> ORGANISM: Artificial Sequence
<220> FEATURE:
<223> OTHER INFORMATION: Synthetic

<400> SEQUENCE: 75

Glu Val Gln Leu Val Glu Ser Gly Gly Gly Leu Val Gln Ala Gly Glu
  1               5                  10                  15

Ser Leu Arg Leu Ser Cys Ala Ala Ser Gly Ser Thr Phe Asp Phe Lys
             20                  25                  30

Val Met Gly Trp Tyr Arg Gln Pro Pro Gly Lys Gln Arg Glu Gly Val
         35                  40                  45

Ala Ala Ile Arg Leu Ser Gly Asn Met His Tyr Ala Glu Ser Val Lys
     50                  55                  60

Gly Arg Phe Ala Ile Ser Lys Ala Asn Ala Lys Asn Thr Val Tyr Leu
 65                  70                  75                  80

Gln Met Asn Ser Leu Arg Pro Glu Asp Thr Ala Val Tyr Tyr Cys Lys
                 85                  90                  95

Val Asn Ile Arg Gly Gln Asp Tyr Trp Gly Gln Gly Thr Gln Val Thr
            100                 105                 110

Val Ser Ser Val Ser Ser
        115

<210> SEQ ID NO 76
<211> LENGTH: 593
<212> TYPE: PRT
<213> ORGANISM: Artificial Sequence
<220> FEATURE:
<223> OTHER INFORMATION: Synthetic

<400> SEQUENCE: 76

Met Gly Thr Ala Arg Ile Ala Pro Gly Leu Ala Leu Leu Leu Cys Cys
  1               5                  10                  15

Pro Val Leu Ser Ser Ala Tyr Ala Leu Val Asp Ala Asp Asp Val Met
             20                  25                  30

Thr Lys Glu Glu Gln Ile Phe Leu Leu His Arg Ala Gln Ala Gln Cys
         35                  40                  45

Glu Lys Arg Leu Lys Glu Val Leu Gln Arg Pro Ala Ser Ile Met Glu
     50                  55                  60

Ser Asp Lys Gly Trp Thr Ser Ala Ser Thr Ser Gly Lys Pro Arg Lys
 65                  70                  75                  80

Asp Lys Ala Ser Gly Lys Leu Tyr Pro Glu Ser Glu Glu Asp Lys Glu
                 85                  90                  95

Ala Pro Thr Gly Ser Arg Tyr Arg Gly Arg Pro Cys Leu Pro Glu Trp
            100                 105                 110

Asp His Ile Leu Cys Trp Pro Leu Gly Ala Pro Gly Glu Val Val Ala
            115                 120                 125

Val Pro Cys Pro Asp Tyr Ile Tyr Asp Phe Asn His Lys Gly His Ala
        130                 135                 140

Tyr Arg Arg Cys Asp Arg Asn Gly Ser Trp Glu Leu Val Pro Gly His
145                 150                 155                 160

Asn Arg Thr Trp Ala Asn Tyr Ser Glu Cys Val Lys Phe Leu Thr Asn
                165                 170                 175

Glu Thr Arg Glu Arg Glu Val Phe Asp Arg Leu Gly Met Ile Tyr Thr
            180                 185                 190
```

```
Val Gly Tyr Ser Val Ser Leu Ala Ser Leu Thr Val Ala Val Leu Ile
            195                 200                 205
Leu Ala Tyr Phe Arg Arg Leu His Cys Thr Arg Asn Tyr Ile His Met
210                 215                 220
His Leu Phe Leu Ser Phe Met Leu Arg Ala Val Ser Ile Phe Val Lys
225                 230                 235                 240
Asp Ala Val Leu Tyr Ser Gly Ala Thr Leu Asp Glu Ala Glu Arg Leu
            245                 250                 255
Thr Glu Glu Leu Arg Ala Ile Ala Gln Ala Pro Pro Pro Ala
            260                 265                 270
Thr Ala Ala Gly Tyr Ala Gly Cys Arg Val Ala Val Thr Phe Phe
            275                 280                 285
Leu Tyr Phe Leu Ala Thr Asn Tyr Tyr Trp Ile Leu Val Glu Gly Leu
290                 295                 300
Tyr Leu His Ser Leu Ile Phe Met Ala Phe Phe Ser Glu Lys Lys Tyr
305                 310                 315                 320
Leu Trp Gly Phe Thr Val Phe Gly Trp Gly Leu Pro Ala Val Phe Val
            325                 330                 335
Ala Val Trp Val Ser Val Arg Ala Thr Leu Ala Asn Thr Gly Cys Trp
            340                 345                 350
Asp Leu Ser Ser Gly Asn Lys Lys Trp Ile Ile Gln Val Pro Ile Leu
            355                 360                 365
Ala Ser Ile Val Leu Asn Phe Ile Leu Phe Ile Asn Ile Val Arg Val
            370                 375                 380
Leu Ala Thr Lys Leu Arg Glu Thr Asn Ala Gly Arg Cys Asp Thr Arg
385                 390                 395                 400
Gln Gln Tyr Arg Lys Leu Leu Lys Ser Thr Leu Val Leu Met Pro Leu
            405                 410                 415
Phe Gly Val His Tyr Ile Val Phe Met Ala Thr Pro Tyr Thr Glu Val
            420                 425                 430
Ser Gly Thr Leu Trp Gln Val Gln Met His Tyr Glu Met Leu Phe Asn
            435                 440                 445
Ser Phe Gln Gly Phe Phe Val Ala Ile Ile Tyr Cys Phe Cys Asn Gly
            450                 455                 460
Glu Val Gln Ala Glu Ile Lys Lys Ser Trp Ser Arg Trp Thr Leu Ala
465                 470                 475                 480
Leu Asp Phe Lys Arg Lys Ala Arg Ser Gly Ser Ser Tyr Ser Tyr
            485                 490                 495
Gly Pro Met Val Ser His Thr Ser Val Thr Asn Val Gly Pro Arg Val
            500                 505                 510
Gly Leu Gly Leu Pro Leu Ser Pro Arg Leu Leu Pro Thr Ala Thr Thr
            515                 520                 525
Asn Gly His Pro Gln Leu Pro Gly His Ala Lys Pro Gly Thr Pro Ala
            530                 535                 540
Leu Glu Thr Leu Glu Thr Thr Pro Pro Ala Met Ala Ala Pro Lys Asp
545                 550                 555                 560
Asp Gly Phe Leu Asn Gly Ser Cys Ser Gly Leu Asp Glu Glu Ala Ser
            565                 570                 575
Gly Pro Glu Arg Pro Pro Ala Leu Leu Gln Glu Glu Trp Glu Thr Val
            580                 585                 590
Met
```

<210> SEQ ID NO 77
<211> LENGTH: 680
<212> TYPE: PRT
<213> ORGANISM: Artificial Sequence
<220> FEATURE:
<223> OTHER INFORMATION: Synthetic

<400> SEQUENCE: 77

```
Met Gly Thr Ala Arg Ile Ala Pro Gly Leu Ala Leu Leu Cys Cys
1               5                   10                  15

Pro Val Leu Ser Ser Ala Tyr Ala Leu Ala Thr Met Val Ser Lys Gly
                20                  25                  30

Glu Glu Leu Phe Thr Gly Val Val Pro Ile Leu Val Glu Leu Asp Gly
            35                  40                  45

Asp Val Asn Gly His Lys Phe Ser Val Ser Gly Glu Gly Glu Gly Asp
        50                  55                  60

Ala Thr Tyr Gly Lys Leu Thr Leu Lys Leu Ile Cys Thr Thr Gly Lys
65                  70                  75                  80

Leu Pro Val Pro Trp Pro Thr Leu Val Thr Thr Leu Gly Tyr Gly Val
                85                  90                  95

Gln Cys Phe Ala Arg Tyr Pro Asp His Met Lys Gln His Asp Phe Phe
            100                 105                 110

Lys Ser Ala Met Pro Glu Gly Tyr Val Gln Glu Arg Thr Ile Phe Phe
        115                 120                 125

Lys Asp Asp Gly Asn Tyr Lys Thr Arg Ala Glu Val Lys Phe Glu Gly
    130                 135                 140

Asp Thr Leu Val Asn Arg Ile Glu Leu Lys Gly Ile Asp Phe Lys Glu
145                 150                 155                 160

Asp Gly Asn Ile Leu Gly His Lys Leu Glu Tyr Asn Tyr Asn Ser His
                165                 170                 175

Asn Val Tyr Ile Thr Ala Asp Lys Gln Lys Asn Gly Ile Lys Ala Asn
            180                 185                 190

Phe Lys Ile Arg His Asn Ile Glu Asp Gly Gly Val Gln Leu Ala Asp
        195                 200                 205

His Tyr Gln Gln Asn Thr Pro Ile Gly Asp Gly Pro Val Leu Leu Pro
    210                 215                 220

Asp Asn His Tyr Leu Ser Tyr Gln Ser Lys Leu Ser Lys Asp Pro Asn
225                 230                 235                 240

Glu Lys Arg Asp His Met Val Leu Leu Glu Phe Val Thr Ala Ala Gly
                245                 250                 255

Ile Thr Leu Gly Met Asp Glu Leu Tyr Lys Gly Ser Gly Glu Val Phe
            260                 265                 270

Asp Arg Leu Gly Met Ile Tyr Thr Val Gly Tyr Ser Val Ser Leu Ala
        275                 280                 285

Ser Leu Thr Val Ala Val Leu Ile Leu Ala Tyr Phe Arg Arg Leu His
    290                 295                 300

Cys Thr Arg Asn Tyr Ile His Met His Leu Phe Leu Ser Phe Met Leu
305                 310                 315                 320

Arg Ala Val Ser Ile Phe Val Lys Asp Ala Val Leu Tyr Ser Gly Ala
                325                 330                 335

Thr Leu Asp Glu Ala Glu Arg Leu Thr Glu Glu Leu Arg Ala Ile
            340                 345                 350

Ala Gln Ala Pro Pro Pro Ala Thr Ala Ala Gly Tyr Ala Gly
        355                 360                 365
```

Cys Arg Val Ala Val Thr Phe Phe Leu Tyr Phe Leu Ala Thr Asn Tyr
    370                 375                 380

Tyr Trp Ile Leu Val Glu Gly Leu Tyr Leu His Ser Leu Ile Phe Met
385                 390                 395                 400

Ala Phe Phe Ser Glu Lys Lys Tyr Leu Trp Gly Phe Thr Val Phe Gly
                405                 410                 415

Trp Gly Leu Pro Ala Val Phe Val Ala Val Trp Val Ser Val Arg Ala
                420                 425                 430

Thr Leu Ala Asn Thr Gly Cys Trp Asp Leu Ser Ser Gly Asn Lys Lys
                435                 440                 445

Trp Ile Ile Gln Val Pro Ile Leu Ala Ser Ile Val Leu Asn Phe Ile
450                 455                 460

Leu Phe Ile Asn Ile Val Arg Val Leu Ala Thr Lys Leu Arg Glu Thr
465                 470                 475                 480

Asn Ala Gly Arg Cys Asp Thr Arg Gln Gln Tyr Arg Lys Leu Leu Lys
                485                 490                 495

Ser Thr Leu Val Leu Met Pro Leu Phe Gly Val His Tyr Ile Val Phe
                500                 505                 510

Met Ala Thr Pro Tyr Thr Glu Val Ser Gly Thr Leu Trp Gln Val Gln
                515                 520                 525

Met His Tyr Glu Met Leu Phe Asn Ser Phe Gln Gly Phe Phe Val Ala
                530                 535                 540

Ile Ile Tyr Cys Phe Cys Asn Gly Glu Val Gln Ala Glu Ile Lys Lys
545                 550                 555                 560

Ser Trp Ser Arg Trp Thr Leu Ala Leu Asp Phe Lys Arg Lys Ala Arg
                565                 570                 575

Ser Gly Ser Ser Ser Tyr Ser Tyr Gly Pro Met Val Ser His Thr Ser
                580                 585                 590

Val Thr Asn Val Gly Pro Arg Val Gly Leu Gly Leu Pro Leu Ser Pro
                595                 600                 605

Arg Leu Leu Pro Thr Ala Thr Thr Asn Gly His Pro Gln Leu Pro Gly
                610                 615                 620

His Ala Lys Pro Gly Thr Pro Ala Leu Glu Thr Leu Glu Thr Thr Pro
625                 630                 635                 640

Pro Ala Met Ala Ala Pro Lys Asp Asp Gly Phe Leu Asn Gly Ser Cys
                645                 650                 655

Ser Gly Leu Asp Glu Glu Ala Ser Gly Pro Glu Arg Pro Pro Ala Leu
                660                 665                 670

Leu Gln Glu Glu Trp Glu Thr Val
                675                 680

<210> SEQ ID NO 78
<211> LENGTH: 593
<212> TYPE: PRT
<213> ORGANISM: Artificial Sequence
<220> FEATURE:
<223> OTHER INFORMATION: Synthetic

<400> SEQUENCE: 78

Met Gly Thr Ala Arg Ile Ala Pro Gly Leu Ala Leu Leu Leu Cys Cys
1               5                   10                  15

Pro Val Leu Ser Ser Ala Tyr Ala Leu Val Asp Ala Asp Asp Val Met
                20                  25                  30

Thr Lys Glu Glu Gln Ile Phe Leu Leu His Arg Ala Gln Ala Gln Cys
            35                  40                  45

```
Glu Lys Arg Leu Lys Glu Val Leu Gln Arg Pro Ala Ser Ile Met Glu
 50                  55                  60

Ser Asp Lys Gly Trp Thr Gln Ala Asp Gln Glu Ala Lys Glu Leu Ala
 65                  70                  75                  80

Arg Gln Ile Ser Gly Lys Leu Tyr Pro Glu Ser Glu Asp Lys Glu
                 85                  90                  95

Ala Pro Thr Gly Ser Arg Tyr Arg Gly Arg Pro Cys Leu Pro Glu Trp
                100                 105                 110

Asp His Ile Leu Cys Trp Pro Leu Gly Ala Pro Gly Glu Val Val Ala
                115                 120                 125

Val Pro Cys Pro Asp Tyr Ile Tyr Asp Phe Asn His Lys Gly His Ala
130                 135                 140

Tyr Arg Arg Cys Asp Arg Asn Gly Ser Trp Glu Leu Val Pro Gly His
145                 150                 155                 160

Asn Arg Thr Trp Ala Asn Tyr Ser Glu Cys Val Lys Phe Leu Thr Asn
                165                 170                 175

Glu Thr Arg Glu Arg Glu Val Phe Asp Arg Leu Gly Met Ile Tyr Thr
                180                 185                 190

Val Gly Tyr Ser Val Ser Leu Ala Ser Leu Thr Val Ala Val Leu Ile
    195                 200                 205

Leu Ala Tyr Phe Arg Arg Leu His Cys Thr Arg Asn Tyr Ile His Met
210                 215                 220

His Leu Phe Leu Ser Phe Met Leu Arg Ala Val Ser Ile Phe Val Lys
225                 230                 235                 240

Asp Ala Val Leu Tyr Ser Gly Ala Thr Leu Asp Glu Ala Glu Arg Leu
                245                 250                 255

Thr Glu Glu Glu Leu Arg Ala Ile Ala Gln Ala Pro Pro Pro Pro Ala
                260                 265                 270

Thr Ala Ala Ala Gly Tyr Ala Gly Cys Arg Val Ala Val Thr Phe Phe
    275                 280                 285

Leu Tyr Phe Leu Ala Thr Asn Tyr Tyr Trp Ile Leu Val Glu Gly Leu
    290                 295                 300

Tyr Leu His Ser Leu Ile Phe Met Ala Phe Phe Ser Glu Lys Lys Tyr
305                 310                 315                 320

Leu Trp Gly Phe Thr Val Phe Gly Trp Gly Leu Pro Ala Val Phe Val
                325                 330                 335

Ala Val Trp Val Ser Val Arg Ala Thr Leu Ala Asn Thr Gly Cys Trp
                340                 345                 350

Asp Leu Ser Ser Gly Asn Lys Lys Trp Ile Ile Gln Val Pro Ile Leu
                355                 360                 365

Ala Ser Ile Val Leu Asn Phe Ile Leu Phe Ile Asn Ile Val Arg Val
                370                 375                 380

Leu Ala Thr Lys Leu Arg Glu Thr Asn Ala Gly Arg Cys Asp Thr Arg
385                 390                 395                 400

Gln Gln Tyr Arg Lys Leu Leu Lys Ser Thr Leu Val Leu Met Pro Leu
                405                 410                 415

Phe Gly Val His Tyr Ile Val Phe Met Ala Thr Pro Tyr Thr Glu Val
                420                 425                 430

Ser Gly Thr Leu Trp Gln Val Gln Met His Tyr Glu Met Leu Phe Asn
                435                 440                 445

Ser Phe Gln Gly Phe Phe Val Ala Ile Ile Tyr Cys Phe Cys Asn Gly
450                 455                 460
```

```
Glu Val Gln Ala Glu Ile Lys Lys Ser Trp Ser Arg Trp Thr Leu Ala
465                 470                 475                 480

Leu Asp Phe Lys Arg Lys Ala Arg Ser Gly Ser Ser Tyr Ser Tyr
            485                 490                 495

Gly Pro Met Val Ser His Thr Ser Val Thr Asn Val Gly Pro Arg Val
            500                 505                 510

Gly Leu Gly Leu Pro Leu Ser Pro Arg Leu Leu Pro Thr Ala Thr Thr
            515                 520                 525

Asn Gly His Pro Gln Leu Pro Gly His Ala Lys Pro Gly Thr Pro Ala
            530                 535                 540

Leu Glu Thr Leu Glu Thr Thr Pro Pro Ala Met Ala Ala Pro Lys Asp
545                 550                 555                 560

Asp Gly Phe Leu Asn Gly Ser Cys Ser Gly Leu Asp Glu Glu Ala Ser
                565                 570                 575

Gly Pro Glu Arg Pro Pro Ala Leu Leu Gln Glu Glu Trp Glu Thr Val
                580                 585                 590

Met

<210> SEQ ID NO 79
<211> LENGTH: 39
<212> TYPE: PRT
<213> ORGANISM: Artificial Sequence
<220> FEATURE:
<223> OTHER INFORMATION: Synthetic

<400> SEQUENCE: 79

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His Lys
            20                  25                  30

Leu Leu Val Leu Asp Ala Pro
        35

<210> SEQ ID NO 80
<211> LENGTH: 126
<212> TYPE: PRT
<213> ORGANISM: Artificial Sequence
<220> FEATURE:
<223> OTHER INFORMATION: Synthetic

<400> SEQUENCE: 80

Gln Val Gln Leu Val Glu Ser Gly Gly Gly Trp Val Gln Pro Gly Gly
1               5                   10                  15

Ser Leu Arg Leu Ser Cys Ala Ala Ser Gly Phe Thr Phe Ser Asp Thr
            20                  25                  30

Ala Met Met Trp Val Arg Gln Ala Pro Gly Lys Gly Arg Glu Trp Val
            35                  40                  45

Ala Ala Ile Asp Thr Gly Gly Gly Tyr Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Arg Tyr Tyr Cys
                85                  90                  95

Ala Lys Thr Tyr Ser Gly Asn Tyr Tyr Ser Asn Tyr Thr Val Ala Asn
            100                 105                 110

Tyr Gly Thr Thr Gly Arg Gly Thr Leu Val Thr Val Ser Ser
        115                 120                 125
```

```
<210> SEQ ID NO 81
<211> LENGTH: 8
<212> TYPE: PRT
<213> ORGANISM: Artificial Sequence
<220> FEATURE:
<223> OTHER INFORMATION: Synthetic

<400> SEQUENCE: 81

Gly Gly Leu Pro Glu Thr Gly Gly
1               5

<210> SEQ ID NO 82
<211> LENGTH: 831
<212> TYPE: PRT
<213> ORGANISM: Artificial Sequence
<220> FEATURE:
<223> OTHER INFORMATION: Synthetic

<400> SEQUENCE: 82

Met Gly Thr Ala Arg Ile Ala Pro Gly Leu Ala Leu Leu Cys Cys
1               5                   10                  15

Pro Val Leu Ser Ser Ala Tyr Ala Leu Val Asp Ala Asp Val Met
                20                  25                  30

Thr Lys Glu Glu Gln Ile Phe Leu Leu His Arg Ala Gln Ala Gln Cys
            35                  40                  45

Glu Lys Arg Leu Lys Glu Val Leu Gln Arg Pro Ala Ser Ile Met Glu
        50                  55                  60

Ser Asp Lys Gly Trp Thr Ser Ala Ser Thr Ser Gly Lys Pro Arg Lys
65                  70                  75                  80

Asp Lys Ala Ser Gly Lys Leu Tyr Pro Glu Ser Glu Asp Lys Met
                85                  90                  95

Ser Lys Gly Glu Glu Leu Phe Thr Gly Val Val Pro Ile Leu Val Glu
            100                 105                 110

Leu Asp Gly Asp Val Asn Gly His Lys Phe Ser Val Ser Gly Glu Gly
        115                 120                 125

Glu Gly Asp Ala Thr Tyr Gly Lys Leu Thr Leu Lys Phe Ile Cys Thr
    130                 135                 140

Thr Gly Lys Leu Pro Val Pro Trp Pro Thr Leu Val Thr Thr Leu Ser
145                 150                 155                 160

Tyr Gly Val Gln Cys Phe Ser Arg Tyr Pro Asp His Met Lys Gln His
                165                 170                 175

Asp Phe Phe Lys Ser Ala Met Pro Glu Gly Tyr Val Gln Glu Arg Thr
            180                 185                 190

Ile Phe Phe Lys Asp Asp Gly Asn Tyr Lys Thr Arg Ala Glu Val Lys
        195                 200                 205

Phe Glu Gly Asp Thr Leu Val Asn Arg Ile Glu Leu Lys Gly Ile Asp
    210                 215                 220

Phe Lys Glu Asp Gly Asn Ile Leu Gly His Lys Leu Glu Tyr Asn Tyr
225                 230                 235                 240

Asn Glu His Leu Val Tyr Ile Met Ala Asp Lys Gln Lys Asn Gly Thr
                245                 250                 255

Lys Ala Ile Phe Gln Val His His Asn Ile Glu Asp Gly Ser Val Gln
            260                 265                 270

Leu Ala Asp His Tyr Gln Gln Asn Thr Pro Ile Gly Asp Gly Pro Val
        275                 280                 285

Leu Leu Pro Asp Asn His Tyr Leu His Thr Gln Ser Ala Leu Ser Lys
    290                 295                 300
```

-continued

```
Asp Pro Asn Glu Lys Arg Asp His Met Val Leu Leu Glu Phe Val Thr
305                 310                 315                 320

Ala Ala Gly Ile Thr His Gly Met Asp Glu Leu Tyr Lys Glu Ala Pro
            325                 330                 335

Thr Gly Ser Arg Tyr Arg Gly Arg Pro Cys Leu Pro Glu Trp Asp His
        340                 345                 350

Ile Leu Cys Trp Pro Leu Gly Ala Pro Gly Glu Val Ala Val Pro
    355                 360                 365

Cys Pro Asp Tyr Ile Tyr Asp Phe Asn His Lys Gly His Ala Tyr Arg
370                 375                 380

Arg Cys Asp Arg Asn Gly Ser Trp Glu Leu Val Pro Gly His Asn Arg
385                 390                 395                 400

Thr Trp Ala Asn Tyr Ser Glu Cys Val Lys Phe Leu Thr Asn Glu Thr
                405                 410                 415

Arg Glu Arg Glu Val Phe Asp Arg Leu Gly Met Ile Tyr Thr Val Gly
            420                 425                 430

Tyr Ser Val Ser Leu Ala Ser Leu Thr Val Ala Val Leu Ile Leu Ala
        435                 440                 445

Tyr Phe Arg Arg Leu His Cys Thr Arg Asn Tyr Ile His Met His Leu
450                 455                 460

Phe Leu Ser Phe Met Leu Arg Ala Val Ser Ile Phe Val Lys Asp Ala
465                 470                 475                 480

Val Leu Tyr Ser Gly Ala Thr Leu Asp Glu Ala Glu Arg Leu Thr Glu
                485                 490                 495

Glu Glu Leu Arg Ala Ile Ala Gln Ala Pro Pro Pro Ala Thr Ala
            500                 505                 510

Ala Ala Gly Tyr Ala Gly Cys Arg Val Ala Val Thr Phe Phe Leu Tyr
        515                 520                 525

Phe Leu Ala Thr Asn Tyr Tyr Trp Ile Leu Val Glu Gly Leu Tyr Leu
530                 535                 540

His Ser Leu Ile Phe Met Ala Phe Phe Ser Glu Lys Lys Tyr Leu Trp
545                 550                 555                 560

Gly Phe Thr Val Phe Gly Trp Gly Leu Pro Ala Val Phe Val Ala Val
                565                 570                 575

Trp Val Ser Val Arg Ala Thr Leu Ala Asn Thr Gly Cys Trp Asp Leu
            580                 585                 590

Ser Ser Gly Asn Lys Lys Trp Ile Ile Gln Val Pro Ile Leu Ala Ser
        595                 600                 605

Ile Val Leu Asn Phe Ile Leu Phe Ile Asn Ile Val Arg Val Leu Ala
610                 615                 620

Thr Lys Leu Arg Glu Thr Asn Ala Gly Arg Cys Asp Thr Arg Gln Gln
625                 630                 635                 640

Tyr Arg Lys Leu Leu Lys Ser Thr Leu Val Leu Met Pro Leu Phe Gly
                645                 650                 655

Val His Tyr Ile Val Phe Met Ala Thr Pro Tyr Thr Glu Val Ser Gly
            660                 665                 670

Thr Leu Trp Gln Val Gln Met His Tyr Glu Met Leu Phe Asn Ser Phe
        675                 680                 685

Gln Gly Phe Phe Val Ala Ile Ile Tyr Cys Phe Cys Asn Gly Glu Val
690                 695                 700

Gln Ala Glu Ile Lys Lys Ser Trp Ser Arg Trp Thr Leu Ala Leu Asp
705                 710                 715                 720
```

```
Phe Lys Arg Lys Ala Arg Ser Gly Ser Ser Ser Tyr Ser Tyr Gly Pro
                725                 730                 735

Met Val Ser His Thr Ser Val Thr Asn Val Gly Pro Arg Val Gly Leu
            740                 745                 750

Gly Leu Pro Leu Ser Pro Arg Leu Leu Pro Thr Ala Thr Thr Asn Gly
            755                 760                 765

His Pro Gln Leu Pro Gly His Ala Lys Pro Gly Thr Pro Ala Leu Glu
    770                 775                 780

Thr Leu Glu Thr Thr Pro Ala Met Ala Ala Pro Lys Asp Asp Gly
785                 790                 795                 800

Phe Leu Asn Gly Ser Cys Ser Gly Leu Asp Glu Glu Ala Ser Gly Pro
                805                 810                 815

Glu Arg Pro Pro Ala Leu Leu Gln Glu Glu Trp Glu Thr Val Met
            820                 825                 830

<210> SEQ ID NO 83
<211> LENGTH: 435
<212> TYPE: PRT
<213> ORGANISM: Artificial Sequence
<220> FEATURE:
<223> OTHER INFORMATION: Synthetic

<400> SEQUENCE: 83

Met Gly Ala Ala Arg Ile Ala Pro Ser Leu Ala Leu Leu Leu Cys Cys
1               5                   10                  15

Pro Val Leu Ser Ser Ala Tyr Ala Leu Glu Val Phe Asp Arg Leu Gly
            20                  25                  30

Met Ile Tyr Thr Val Gly Tyr Ser Met Ser Leu Ala Ser Leu Thr Val
            35                  40                  45

Ala Val Leu Ile Leu Ala Tyr Phe Arg Arg Leu His Cys Thr Arg Asn
50                  55                  60

Tyr Ile His Met His Met Phe Leu Ser Phe Met Leu Arg Ala Ala Ser
65                  70                  75                  80

Ile Phe Val Lys Asp Ala Val Leu Tyr Ser Gly Phe Thr Leu Asp Glu
                85                  90                  95

Ala Glu Arg Leu Thr Glu Glu Leu His Ile Ile Ala Gln Val Pro
            100                 105                 110

Pro Pro Pro Ala Ala Ala Ala Val Gly Tyr Ala Gly Cys Arg Val Ala
            115                 120                 125

Val Thr Phe Phe Leu Tyr Phe Leu Ala Thr Asn Tyr Tyr Trp Ile Leu
            130                 135                 140

Val Glu Gly Leu Tyr Leu His Ser Leu Ile Phe Met Ala Phe Phe Ser
145                 150                 155                 160

Glu Lys Lys Tyr Leu Trp Gly Phe Thr Ile Phe Gly Trp Gly Leu Pro
                165                 170                 175

Ala Val Phe Val Ala Val Trp Val Gly Val Arg Ala Thr Leu Ala Asn
            180                 185                 190

Thr Gly Cys Trp Asp Leu Ser Ser Gly His Lys Lys Trp Ile Ile Gln
            195                 200                 205

Val Pro Ile Leu Ala Ser Val Val Leu Asn Phe Ile Leu Phe Ile Asn
            210                 215                 220

Ile Ile Arg Val Leu Ala Thr Lys Leu Arg Glu Thr Asn Ala Gly Arg
225                 230                 235                 240

Cys Asp Thr Arg Gln Gln Tyr Arg Lys Leu Leu Arg Ser Thr Leu Val
                245                 250                 255
```

```
Leu Val Pro Leu Phe Gly Val His Tyr Thr Val Phe Met Ala Leu Pro
            260                 265                 270

Tyr Thr Glu Val Ser Gly Thr Leu Trp Gln Ile Gln Met His Tyr Glu
            275                 280                 285

Met Leu Phe Asn Ser Phe Gln Gly Phe Val Ala Ile Ile Tyr Cys
290                 295                 300

Phe Cys Asn Gly Glu Val Gln Ala Glu Ile Arg Lys Ser Trp Ser Arg
305                 310                 315                 320

Trp Thr Leu Ala Leu Asp Phe Lys Arg Lys Ala Arg Ser Gly Ser Ser
            325                 330                 335

Ser Tyr Ser Tyr Gly Pro Met Val Ser His Thr Ser Val Thr Asn Val
            340                 345                 350

Gly Pro Arg Ala Gly Leu Ser Leu Pro Leu Ser Pro Arg Leu Pro Pro
            355                 360                 365

Ala Thr Thr Asn Gly His Ser Gln Leu Pro Gly His Ala Lys Pro Gly
            370                 375                 380

Ala Pro Ala Thr Glu Thr Glu Thr Leu Pro Val Thr Met Ala Val Pro
385                 390                 395                 400

Lys Asp Asp Gly Phe Leu Asn Gly Ser Cys Ser Gly Leu Asp Glu Glu
            405                 410                 415

Ala Ser Gly Ser Ala Arg Pro Pro Pro Leu Leu Gln Glu Gly Trp Glu
            420                 425                 430

Thr Val Met
    435

<210> SEQ ID NO 84
<211> LENGTH: 445
<212> TYPE: PRT
<213> ORGANISM: Artificial Sequence
<220> FEATURE:
<223> OTHER INFORMATION: Synthetic

<400> SEQUENCE: 84

Met Gly Ala Ala Arg Ile Ala Pro Ser Leu Ala Leu Leu Leu Cys Cys
1               5                   10                  15

Pro Val Leu Ser Ser Ala Tyr Pro Tyr Asp Val Pro Asp Tyr Ala Gly
            20                  25                  30

Gly Gly Gly Glu Val Phe Asp Arg Leu Gly Met Ile Tyr Thr Val Gly
            35                  40                  45

Tyr Ser Met Ser Leu Ala Ser Leu Thr Val Ala Val Leu Ile Leu Ala
    50                  55                  60

Tyr Phe Arg Arg Leu His Cys Thr Arg Asn Tyr Ile His Met His Met
65                  70                  75                  80

Phe Leu Ser Phe Met Leu Arg Ala Ala Ser Ile Phe Val Lys Asp Ala
            85                  90                  95

Val Leu Tyr Ser Gly Phe Thr Leu Asp Glu Ala Glu Arg Leu Thr Glu
            100                 105                 110

Glu Glu Leu His Ile Ile Ala Gln Val Pro Pro Pro Ala Ala Ala
            115                 120                 125

Ala Val Gly Tyr Ala Gly Cys Arg Val Ala Val Thr Phe Phe Leu Tyr
            130                 135                 140

Phe Leu Ala Thr Asn Tyr Tyr Trp Ile Leu Val Glu Gly Leu Tyr Leu
145                 150                 155                 160

His Ser Leu Ile Phe Met Ala Phe Phe Ser Glu Lys Lys Tyr Leu Trp
            165                 170                 175
```

```
Gly Phe Thr Ile Phe Gly Trp Gly Leu Pro Ala Val Phe Ala Val
            180                 185                 190

Trp Val Gly Val Arg Ala Thr Leu Ala Asn Thr Gly Cys Trp Asp Leu
        195                 200                 205

Ser Ser Gly His Lys Lys Trp Ile Ile Gln Val Pro Ile Leu Ala Ser
    210                 215                 220

Val Val Leu Asn Phe Ile Leu Phe Ile Asn Ile Ile Arg Val Leu Ala
225                 230                 235                 240

Thr Lys Leu Arg Glu Thr Asn Ala Gly Arg Cys Asp Thr Arg Gln Gln
                245                 250                 255

Tyr Arg Lys Leu Leu Arg Ser Thr Leu Val Leu Val Pro Leu Phe Gly
                260                 265                 270

Val His Tyr Thr Val Phe Met Ala Leu Pro Tyr Thr Glu Val Ser Gly
            275                 280                 285

Thr Leu Trp Gln Ile Gln Met His Tyr Glu Met Leu Phe Asn Ser Phe
        290                 295                 300

Gln Gly Phe Phe Val Ala Ile Ile Tyr Cys Phe Cys Asn Gly Glu Val
305                 310                 315                 320

Gln Ala Glu Ile Arg Lys Ser Trp Ser Arg Trp Thr Leu Ala Leu Asp
                325                 330                 335

Phe Lys Arg Lys Ala Arg Ser Gly Ser Ser Ser Tyr Ser Tyr Gly Pro
                340                 345                 350

Met Val Ser His Thr Ser Val Thr Asn Val Gly Pro Arg Ala Gly Leu
            355                 360                 365

Ser Leu Pro Leu Ser Pro Arg Leu Pro Pro Ala Thr Thr Asn Gly His
        370                 375                 380

Ser Gln Leu Pro Gly His Ala Lys Pro Gly Ala Pro Ala Thr Glu Thr
385                 390                 395                 400

Glu Thr Leu Pro Val Thr Met Ala Val Pro Lys Asp Asp Gly Phe Leu
                405                 410                 415

Asn Gly Ser Cys Ser Gly Leu Asp Glu Glu Ala Ser Gly Ser Ala Arg
                420                 425                 430

Pro Pro Pro Leu Leu Gln Glu Gly Trp Glu Thr Val Met
            435                 440                 445

<210> SEQ ID NO 85
<211> LENGTH: 11
<212> TYPE: PRT
<213> ORGANISM: Artificial Sequence
<220> FEATURE:
<223> OTHER INFORMATION: Synthetic

<400> SEQUENCE: 85

Ala Val Ser Glu Leu Gln Leu Met His Gln Arg
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid
```

```
<400> SEQUENCE: 86

Ala Val Ala Glu Ile Gln Leu Met His
1               5

<210> SEQ ID NO 87
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 87

Ala Val Ala Glu Ile Gln Leu Met His Gln
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 88

Ala Val Ala Glu Ile Gln Leu Met His Gln Arg
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 89

Ala Val Ala Glu Ile Gln Leu Met His Gln Arg Ala Lys Trp
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala is 2-aminoisobutyric acid
<220> FEATURE:
<221> NAME/KEY: MOD_RES
<222> LOCATION: (3)..(3)
<223> OTHER INFORMATION: Ala is 2-aminoisobutyric acid
<220> FEATURE:
<221> NAME/KEY: SITE
<222> LOCATION: (11)..(11)
<223> OTHER INFORMATION: Xaa is homoarginine
```

```
<400> SEQUENCE: 90

Ala Val Ala Glu Ile Gln Leu Met His Gln Xaa Ala Lys Trp
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
<223> OTHER INFORMATION: Xaa is 1-aminocyclopentane-1-carboxylic acid
<220> FEATURE:
<221> NAME/KEY: MOD_RES
<222> LOCATION: (3)..(3)
<223> OTHER INFORMATION: Ala is 2-aminoisobutyric acid
<220> FEATURE:
<221> NAME/KEY: SITE
<222> LOCATION: (11)..(11)
<223> OTHER INFORMATION: Xaa is homoarginine

<400> SEQUENCE: 91

Xaa Val Ala Glu Leu Gln Leu Met His Gln Xaa
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 92

Ala Val Ala Glu Ile Gln Leu Met His Cys
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 93

Ala Val Ala Glu Ile Gln Leu Met His Gln Cys
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid
```

```
<400> SEQUENCE: 94

Ala Val Ala Glu Ile Gln Leu Met His Gln Arg Cys
1               5                   10

<210> SEQ ID NO 95
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ala is 2-aminoisobutyric acid

<400> SEQUENCE: 95

Ala Val Ala Glu Ile Gln Leu Met His Gln Arg Ala Lys Trp Cys
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Synthetic

<400> SEQUENCE: 96

Ser Val Ser Glu Ile Gln Leu Met His Asn Leu Gly Lys His Cys
1               5                   10                  15

<210> SEQ ID NO 97
<211> LENGTH: 12
<212> TYPE: PRT
<213> ORGANISM: Artificial Sequence
<220> FEATURE:
<223> OTHER INFORMATION: Synthetic

<400> SEQUENCE: 97

Pro Tyr Asp Val Pro Asp Tyr Ala Gly Gly Gly Gly
1               5                   10
```